United States Patent
Sasaki et al.

(10) Patent No.: US 7,709,234 B2
(45) Date of Patent: *May 4, 2010

(54) α-1,3-FUCOSYLTRANSFERASE

(75) Inventors: Katsutoshi Sasaki, Tokyo (JP); Kazumi Miura, Kanagawa (JP); Nobuo Hanai, Kanagawa (JP); Tatsunari Nishi, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 950 days.

This patent is subject to a terminal disclaimer.

(21) Appl. No.: 11/276,029

(22) Filed: Feb. 10, 2006

(65) Prior Publication Data

US 2006/0246468 A1 Nov. 2, 2006

Related U.S. Application Data

(60) Division of application No. 08/361,306, filed on Nov. 29, 1994, now Pat. No. 7,094,530, which is a continuation-in-part of application No. PCT/JP94/00496, filed on Mar. 28, 1994.

(30) Foreign Application Priority Data

Mar. 29, 1993 (JP) ................... 5-69016

(51) Int. Cl.
*C12N 9/10* (2006.01)
*C12N 15/54* (2006.01)
*C12P 19/18* (2006.01)

(52) U.S. Cl. .................... 435/97; 435/193; 435/320.1; 435/252.3; 435/252.33; 435/325; 536/23.2

(58) Field of Classification Search ................ None
See application file for complete search history.

(56) References Cited

OTHER PUBLICATIONS

Muramatsu et al, "Purification and propertises of N-acetylglucosaminide α1→3-fucosyltransferase from embryonal carcinoma cells", European Journal Biochem (1986) 157:71-75.

Lowe et al, "ELAM-1-Dependent Cell Adhesion to Vascular Endothelium Determined by a Transfected Human Fucosyltransferase cDNA" Cell, vol. 63, 475-484, Nov. 2, 1990.

*Primary Examiner*—Rebecca Prouty
(74) *Attorney, Agent, or Firm*—Nixon & Vanderhye P.C.

(57) ABSTRACT

The invention provides a novel species of α-1,3-fucosyltransferase expressed by a gene cloned from animal cells, a cDNA coding for the α-1,3-fucosyltransferase, a method of detecting, or inhibiting the production of, the α-1,3-fucosyltransferase which involves the use of the cDNA, a recombinant vector containing the DNA as an insert, a cell harboring the recombinant vector, and a method of producing same. The α-1,3-fucosyltransferase of the invention is useful in the production of carbohydrate chains having useful physiological activity, for example sialyl Lewis x, and modifications thereof.

7 Claims, 32 Drawing Sheets

SYNTHETIC LINKER

```
    Sall    HindIII   EcoRV         Sfil  Stul    Sfil     Notl       Kpnl
5' TCGACA AGCTTGAT ATCGGCCTGTG AGG CCTCAC TGGCCGC GGCCGCGGTAC 3'  (52 mer)
3'    GTTCGA ACTATAGCCGGA CACTCC GGAGTGA CCGGCGCCGG CGC 5'        (44 mer)
```

StuI PARTIAL DIGESTION

BamHI linker
(5' pCCGGATCCGG 3')

BamHI

T4-DNA LIGASE

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1701
      (B) TYPE: nucleic acid -continued

```
        (C) STRANDEDNESS: double
        (D) TOPOLOGY: linear (ii) MOLECULE TYPE: cDNA to mRNA
            ORIGINAL SOURCE:
            ORGANISM: Homo sapiens
            STRAIN: THP-1 cell
            CELL TYPE: monocytic cell (xi) SEQUENCE DESCRIPTION: SEQ ID NO:1:

AAGGAGCACA GTTCCAGGCG GGGCTGAGCT AGGGCGTAGC TGTGATTTCA GGGGCACCTC      60

TGGCGGCTGC CGTGATTTGA GAATCTCGGG TCTCTTGGCT GACTGATCCT GGGAGACTGT     120

GG ATG AAT AAT GCT GGG CAC GGC CCC ACC CGG AGG CTG CGA GGC TTG        167
   Met Asn Asn Ala Gly His Gly Pro Thr Arg Arg Leu Arg Gly Leu
   1               5                   10                  15

GGG GTC CTG GCC GGG GTG GCT CTG CTC GCT GCC CTC TGG CTC CTG TGG       215
Gly Val Leu Ala Gly Val Ala Leu Leu Ala Ala Leu Trp Leu Leu Trp
                20                  25                  30

CTG CTG GGG TCA GCC CCT CGG GGT ACC CCG GCA CCC CAG CCC ACG ATC       263
Leu Leu Gly Ser Ala Pro Arg Gly Thr Pro Ala Pro Gln Pro Thr Ile
                35                  40                  45

ACC ATC CTT GTC TGG CAC TGG CCC TTC ACT GAC CAG CCC CCA GAG CTG       311
Thr Ile Leu Val Trp His Trp Pro Phe Thr Asp Gln Pro Pro Glu Leu
            50                  55                  60

CCC AGC GAC ACC TGC ACC CGC TAC GGC ATC GCC CGC TGC CAC CTG AGT       359
Pro Ser Asp Thr Cys Thr Arg Tyr Gly Ile Ala Arg Cys His Leu Ser
65                  70                  75

GCC AAC CGA AGC CTG CTG GCC AGC GCC GAC GCC GTG GTC TTC CAC CAC       407
Ala Asn Arg Ser Leu Leu Ala Ser Ala Asp Ala Val Val Phe His His
80                  85                  90                  95

CGC GAG CTG CAG ACC CGG CGG TCC CAC CTG CCC CTG GCC CAG CGG CCG       455
Arg Glu Leu Gln Thr Arg Arg Ser His Leu Pro Leu Ala Gln Arg Pro
                100                 105                 110

CGA GGG CAG CCC TGG GTG TGG GCC TCC ATG GAG TCT CCT AGC CAC ACC       503
Arg Gly Gln Pro Trp Val Trp Ala Ser Met Glu Ser Pro Ser His Thr
                115                 120                 125

CAC GGC CTC AGC CAC CTC CGA GGC ATC TTC AAC TGG GTG CTG AGC TAC       551
His Gly Leu Ser His Leu Arg Gly Ile Phe Asn Trp Val Leu Ser Tyr
            130                 135                 140

CGG CGC GAC TCG GAC ATC TTT GTG CCC TAT GGC CGC CTG GAG CCC CAC       599
Arg Arg Asp Ser Asp Ile Phe Val Pro Tyr Gly Arg Leu Glu Pro His
        145                 150                 155

TGG GGG CCC TCG CCA CCG CTG CCA GCC AAG AGC AGG GTG GCC GCC TGG       647
Trp Gly Pro Ser Pro Pro Leu Pro Ala Lys Ser Arg Val Ala Ala Trp
160                 165                 170                 175

GTG GTC AGC AAC TTC CAG GAG CGG CAG CTG CGT GCC AGG CTG TAC CGG       695
Val Val Ser Asn Phe Gln Glu Arg Gln Leu Arg Ala Arg Leu Tyr Arg
                180                 185                 190

CAG CTG GCG CCT CAT CTG CGG GTG GAT GTC TTT GGC CGT GCC AAT GGA       743
Gln Leu Ala Pro His Leu Arg Val Asp Val Phe Gly Arg Ala Asn Gly
                195                 200                 205

CGG CCA CTG TGC GCC AGC TGC CTG GTG CCC ACC GTG GCC CAG TAC CGC       791
Arg Pro Leu Cys Ala Ser Cys Leu Val Pro Thr Val Ala Gln Tyr Arg
            210                 215                 220

TTC TAC CTG TCC TTT GAG AAC TCT CAG CAC CGC GAC TAC ATT ACG GAG       839
Phe Tyr Leu Ser Phe Glu Asn Ser Gln His Arg Asp Tyr Ile Thr Glu
        225                 230                 235

AAA TTC TGG CGC AAC GCA CTG GTG GCT GGC ACT GTG CCA GTG GTG CTG       887
Lys Phe Trp Arg Asn Ala Leu Val Ala Gly Thr Val Pro Val Val Leu
240                 245                 250                 255
```

```
GGG CCC CCA CGG GCC ACC TAT GAG GCC TTC GTG CCG GCT GAC GCC TTC      935
Gly Pro Pro Arg Ala Thr Tyr Glu Ala Phe Val Pro Ala Asp Ala Phe
            260                 265                 270

GTG CAT GTG GAT GAC TTT GGC TCA GCC CGA GAG CTG GCG GCT TTC CTC      983
Val His Val Asp Asp Phe Gly Ser Ala Arg Glu Leu Ala Ala Phe Leu
        275                 280                 285

ACT GGC ATG AAT GAG AGC CGA TAC CAA CGC TTC TTT GCC TGG CGT GAC     1031
Thr Gly Met Asn Glu Ser Arg Tyr Gln Arg Phe Phe Ala Trp Arg Asp
            290                 295                 300

AGG CTC CGC GTG CGA CTG TTC ACC GAC TGG CGG GAA CGT TTC TGT GCC     1079
Arg Leu Arg Val Arg Leu Phe Thr Asp Trp Arg Glu Arg Phe Cys Ala
        305                 310                 315

ATC TGT GAC CGC TAC CCA CAC CTA CCC CGC AGC CAA GTC TAT GAG GAC     1127
Ile Cys Asp Arg Tyr Pro His Leu Pro Arg Ser Gln Val Tyr Glu Asp
320                 325                 330                 335

CTT GAG GGT TGG TTT CAG GCC TGA GATCCGCTGG CCGGGGGAGG TGGGTGTGGG    1181
Leu Glu Gly Trp Phe Gln Ala TER
            340     342

TGGAAGGGCT GGGTGTCGAA ATCAAACCAC CAGGCATCCG GCCCTTACCG GCAAGCAGCG   1241

GGCTAACGGG AGGCTGGGCA CAGAGGTCAG GAAGCAGGGG TGGGGGGTGC AGGTGGGCAC   1301

TGGAGCATGC AGAGGAGGTG AGAGTGGGAG GGAGGTAACG GGTGCCTGCT GCGGCAGACG   1361

GGAGGGGAAA GGCTGCCGAG GACCCTCCCC ACCCTGAACA ATCTTGGGT GGGTGAAGGC    1421

CTGGCTGGAA GAGGGTGAAA GGCAGGGCCC TTGGGGCTGG GGGGCACCCC AGCCTGAAGT   1481

TTGTGGGGGC CAAACCTGGG ACCCCGAGCT TCCTCGGTAG CAGAGGCCCT GTGGTCCCCG   1541

AGACACAGGC ACGGGTCCCT GCCACGTCCA TAGTTCTGAG GTCCCTGTGT GTAGGCTGGG   1601

GCGGGGCCCA GGAGACCACG GGGAGCAAAC CAGCTTGTTC TGGGCTCAGG GAGGGAGGGC   1661

GGTGGACAAT AAACGTCTGA GCAGTGAAAA AAAAAAAAA                          1701

(2) INFORMATION FOR SEQ ID NO:2:

(i) SEQUENCE CHARACTERISTICS:
            (A) LENGTH: 342
            (B) TYPE: amino acid
            (D) TOPOLOGY: linear (ii) MOLECULE TYPE: protein
             ORIGINAL SOURCE:
                ORGANISM: Homo sapiens
                STRAIN: THP-1 cell
                CELL TYPE: monocytic cell (xi) SEQUENCE DESCRIPTION:  SEQ ID NO:2:

Met Asn Asn Ala Gly His Gly Pro Thr Arg Arg Leu Arg Gly Leu
1               5                  10                  15

Gly Val Leu Ala Gly Val Ala Leu Leu Ala Leu Trp Leu Leu
                20                  25                  30

Trp Leu Leu Gly Ser Ala Pro Arg Gly Thr Pro Ala Pro Gln Pro
                35                  40                  45

Thr Ile Thr Ile Leu Val Trp His Trp Pro Phe Thr Asp Gln Pro
                50                  55                  60

Pro Glu Leu Pro Ser Asp Thr Cys Thr Arg Tyr Gly Ile Ala Arg
                65                  70                  75

Cys His Leu Ser Ala Asn Arg Ser Leu Leu Ala Ser Ala Asp Ala
                80                  85                  90

Val Val Phe His His Arg Glu Leu Gln Thr Arg Arg Ser His Leu
                95                  100                 105
```

-continued

```
Pro Leu Ala Gln Arg Pro Arg Gly Gln Pro Trp Val Trp Ala Ser
                110                 115                 120

Met Glu Ser Pro Ser His Thr His Gly Leu Ser His Leu Arg Gly
            125                 130                 135

Ile Phe Asn Trp Val Leu Ser Tyr Arg Arg Asp Ser Asp Ile Phe
            140                 145                 150

Val Pro Tyr Gly Arg Leu Glu Pro His Trp Gly Pro Ser Pro Pro
            155                 160                 165

Leu Pro Ala Lys Ser Arg Val Ala Ala Trp Val Ser Asn Phe
            170                 175                 180

Gln Glu Arg Gln Leu Arg Ala Arg Leu Tyr Arg Gln Leu Ala Pro
            185                 190                 195

His Leu Arg Val Asp Val Phe Gly Arg Ala Asn Gly Arg Pro Leu
            200                 205                 210

Cys Ala Ser Cys Leu Val Pro Thr Val Ala Gln Tyr Arg Phe Tyr
            215                 220                 225

Leu Ser Phe Glu Asn Ser Gln His Arg Asp Tyr Ile Thr Glu Lys
            230                 235                 240

Phe Trp Arg Asn Ala Leu Val Ala Gly Thr Val Pro Val Val Leu
            245                 250                 255

Gly Pro Pro Arg Ala Thr Tyr Glu Ala Phe Val Pro Ala Asp Ala
            260                 265                 270

Phe Val His Val Asp Asp Phe Gly Ser Ala Arg Glu Leu Ala Ala
            275                 280                 285

Phe Leu Thr Gly Met Asn Glu Ser Arg Tyr Gln Arg Phe Phe Ala
            290                 295                 300

Trp Arg Asp Arg Leu Arg Val Arg Leu Phe Thr Asp Trp Arg Glu
            305                 310                 315

Arg Phe Cys Ala Ile Cys Asp Arg Tyr Pro His Leu Pro Arg Ser
            320                 325                 330

Gln Val Tyr Glu Asp Leu Glu Gly Trp Phe Gln Ala
            335                 340     342

(2) INFORMATION FOR SEQ ID NO:3:

(i) SEQUENCE CHARACTERISTICS:
        (A) LENGTH: 52
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:3:

TCGACAAGCT TGATATCGGC CTGTGAGGCC TCACTGGCCG CGGCCGCGGT AC          52

(2) INFORMATION FOR SEQ ID NO:4:

(i) SEQUENCE CHARACTERISTICS:
        (A) LENGTH: 44
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:4:

GTTCGAACTA TAGCCGGACA CTCCGGAGTG ACCGGCGCCG GCGC                  44
```

(2) INFORMATION FOR SEQ ID NO:5:

(i) SEQUENCE CHARACTERISTICS:
        (A) LENGTH: 11
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:5:

```
CTTTAGAGCA C                                                          11
```

(2) INFORMATION FOR SEQ ID NO:6:

(i) SEQUENCE CHARACTERISTICS:
        (A) LENGTH: 1766
        (B) TYPE: nucleic acid
        (C) STRANDEDNESS: double
        (D) TOPOLOGY: linear (ii) MOLECULE TYPE: cDNA to mRNA
        ORIGINAL SOURCE:
            ORGANISM: Homo sapiens
            STRAIN: WM266-4 cell
            CELL TYPE: melanoma (xi) SEQUENCE DESCRIPTION: SEQ ID NO:6:

```
CGGTCAGGTC CAGCACTTGG GAGCTGACTG TGCTGGAGGT GACAGGCTTT GCGGGGTCCG      60

CCTGTGTGCA GGAGTCGCAA GGTCGCTGAG CAGGACCCAA AGGTGGCCCG AGGCAGCCGG     120

GATGACAGCT CTCCCCAGGA ATCCTGCTGC TGCTGAGAA AC ATG GTC AGC AAG         174
                                              Met Val Ser Lys
                                                              1

TCC CGC TGG AAG CTC CTG GCC ATG TTG GCT CTG GTC CTG GTC GTC ATG       222
Ser Arg Trp Lys Leu Leu Ala Met Leu Ala Leu Val Leu Val Val Met
  5              10                  15                  20

GTG TGG TAT TCC ATC TCC CGG GAA GAC AGT TTT TAT TTT CCC ATC CCA       270
Val Trp Tyr Ser Ile Ser Arg Glu Asp Ser Phe Tyr Phe Pro Ile Pro
             25                  30                  35

GAG AAG AAG GAG CCG TGC CTC CAG GGT GAG GCA GAG AGC AAG GCC TCT       318
Glu Lys Lys Glu Pro Cys Leu Gln Gly Glu Ala Glu Ser Lys Ala Ser
         40                  45                  50

AAG CTC TTT GGC AAC TAC TCC CGG GAT CAG CCC ATC TTC CTG CGG CTT       366
Lys Leu Phe Gly Asn Tyr Ser Arg Asp Gln Pro Ile Phe Leu Arg Leu
             55                  60                  65

GAG GAT TAT TTC TGG GTC AAG ACG CCA TCT GCT TAC GAG CTG CCC TAT       414
Glu Asp Tyr Phe Trp Val Lys Thr Pro Ser Ala Tyr Glu Leu Pro Tyr
     70                  75                  80

GGG ACC AAG GGG AGT GAG GAT CTG CTC CTC CGG GTG CTA GCC ATC ACC       462
Gly Thr Lys Gly Ser Glu Asp Leu Leu Leu Arg Val Leu Ala Ile Thr
 85                  90                  95                 100

AGC TCC TCC ATC CCC AAG AAC ATC CAG AGC CTC AGG TGC CGC CGC TGT       510
Ser Ser Ser Ile Pro Lys Asn Ile Gln Ser Leu Arg Cys Arg Arg Cys
                105                 110                 115

GTG GTC GTG GGG AAC GGG CAC CGG CTG CGG AAC AGC TCA CTG GGA GAT       558
Val Val Val Gly Asn Gly His Arg Leu Arg Asn Ser Ser Leu Gly Asp
            120                 125                 130

GCC ATC AAC AAG TAC GAT GTG GTC ATC AGA TTG AAC AAT GCC CCA GTG       606
Ala Ile Asn Lys Tyr Asp Val Val Ile Arg Leu Asn Asn Ala Pro Val
        135                 140                 145

GCT GGC TAT GAG GGT GAC GTG GGC TCC AAG ACC ACC ATG CGT CTC TTC       654
Ala Gly Tyr Glu Gly Asp Val Gly Ser Lys Thr Thr Met Arg Leu Phe
    150                 155                 160
```

-continued

```
TAC CCT GAA TCT GCC CAC TTC GAC CCC AAA GTA GAA AAC AAC CCA GAC      702
Tyr Pro Glu Ser Ala His Phe Asp Pro Lys Val Glu Asn Asn Pro Asp
165             170                 175                 180

ACA CTC CTC GTC CTG GTA GCT TTC AAG GCA ATG GAC TTC CAC TGG ATT      750
Thr Leu Leu Val Leu Val Ala Phe Lys Ala Met Asp Phe His Trp Ile
                185                 190                 195

GAG ACC ATC CTG AGT GAT AAG AAG CGG GTG CGA AAG GGT TTC TGG AAA      798
Glu Thr Ile Leu Ser Asp Lys Lys Arg Val Arg Lys Gly Phe Trp Lys
            200                 205                 210

CAG CCT CCC CTC ATC TGG GAT GTC AAT CCT AAA CAG ATT CGG ATT CTC      846
Gln Pro Pro Leu Ile Trp Asp Val Asn Pro Lys Gln Ile Arg Ile Leu
        215                 220                 225

AAC CCC TTC TTC ATG GAG ATT GCA GCT GAC AAA CTG CTG AGC CTG CCA      894
Asn Pro Phe Phe Met Glu Ile Ala Ala Asp Lys Leu Leu Ser Leu Pro
    230                 235                 240

ATG CAA CAG CCA CGG AAG ATT AAG CAG AAG CCC ACC ACG GGC CTG TTG      942
Met Gln Gln Pro Arg Lys Ile Lys Gln Lys Pro Thr Thr Gly Leu Leu
245                 250                 255                 260

GCC ATC ACG CTG GCC CTC CAC CTC TGT GAC TTG GTG CAC ATT GCC GGC      990
Ala Ile Thr Leu Ala Leu His Leu Cys Asp Leu Val His Ile Ala Gly
                265                 270                 275

TTT GGC TAC CCA GAC GCC TAC AAC AAG AAG CAG ACC ATT CAC TAC TAT     1038
Phe Gly Tyr Pro Asp Ala Tyr Asn Lys Lys Gln Thr Ile His Tyr Tyr
            280                 285                 290

GAG CAG ATC ACG CTC AAG TCC ATG GCG GGG TCA GGC CAT AAT GTC TCC     1086
Glu Gln Ile Thr Leu Lys Ser Met Ala Gly Ser Gly His Asn Val Ser
        295                 300                 305

CAA GAG GCC CTG GCC ATT AAG CGG ATG CTG GAG ATG GGA GCT ATC AAG     1134
Gln Glu Ala Leu Ala Ile Lys Arg Met Leu Glu Met Gly Ala Ile Lys
    310                 315                 320

AAC CTC ACG TCC TTC TGA CCTGGGCAAG AGCTGTAGCC TGTCGGTTGC            1182
Asn Leu Thr Ser Phe TER
325             329

CTACTCTGCT GTCTGGGTGA CCCCCATGCG TGGCTGTGGG GGTGGCTGGT GCCAGTATGA   1242

CCCACTTGGA CTCACCCCCT CTTGGGGAGG GAGTTCTGGG CCTGGCCAGG TCTGAGATGA   1302

GGCCATGCCC CTGGCTGCTC TTATGGAGCC GAGATCCAGT CAGGGTGGGG GCGCTGGAGC   1362

CGTGGGAGCC CGGCCAGGGC AGGGGGCTCG TCGCTGTGGC ACCCCCTCTC TGCCAGCACC   1422

AAGAGATTAT TTAATGGGCT ATTTAATTAA GGGGTAGGAA GGTGCTGTGG GCTGGTCCCA   1482

CACATCCAGG AAAGAGGCCA GTAGAGAATT CTGCCCACTT TTTATAAAAA CTTACAGCGA   1542

TGGCCCCACC AAGGCCTAGA CACGGCACTG GCCTCCCAGG AGGGCAGGGG CATTGGGAAT   1602

GGGTGGGTGC CCTCCAGAGA GGGGCTGCTA CCTCCCAGCA GGCATGGGAA GAGCACTGGT   1662

GTGGGGGTTC CACCGAGAAG GGGACCTCAT CTAGAAAAGA GGTTACAAAC CTACCATTAA   1722

ACTATTTTTC CTAAAACGGA AAAAAAAAA AAAAAAAAA AAAA                     1766
```

(2) INFORMATION FOR SEQ ID NO:7:

(i) SEQUENCE CHARACTERISTICS:
        (A) LENGTH: 44
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:7:

```
CTCTCCGATA TCTGTTTTAT TTTCCCATCC CAGAGAAGAA GGAG                      44
```

(2) INFORMATION FOR SEQ ID NO:8:

(i) SEQUENCE CHARACTERISTICS:
        (A) LENGTH: 36
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:8:

```
GATTAAGGTA CCAGGTCAGA AGGACGTGAG GTTCTT                                36
```

(2) INFORMATION FOR SEQ ID NO:9:

(i) SEQUENCE CHARACTERISTICS:
        (A) LENGTH: 2232
        (B) TYPE: nucleic acid
        (C) STRANDEDNESS: double
        (D) TOPOLOGY: linear (ii) MOLECULE TYPE: cDNA to mRNA
        ORIGINAL SOURCE:
        ORGANISM: Homo sapiens
        STRAIN: WM266-4 cell
        CELL TYPE: melanoma (xi) SEQUENCE DESCRIPTION: SEQ ID NO:9:

```
CGCGTTGTGG GCTCCCGCCG GGGTCCCCCG CGGCTGTCGC CGCCGCCTAC GCCGCTGCCT       60

CCGCCTTCCT GCCCCGCGTC GGGCCGGGCG CCACCTCCCC CCTGCCTCCC TCTCCGCTGT      120

GGTCATTTAG GAAATCGTAA ATCATGTGAA G ATG GGA CTC TTG GTA TTT GTG        172
                                 Met Gly Leu Leu Val Phe Val
                                  1               5

CGC AAT CTG CTG CTA GCC CTC TGC CTC TTT CTG GTA CTG GGA TTT TTG       220
Arg Asn Leu Leu Leu Ala Leu Cys Leu Phe Leu Val Leu Gly Phe Leu
         10                  15                  20

TAT TAT TCT GCG TGG AAG CTA CAC TTA CTC CAG TGG GAG GAG GAC TCC       268
Tyr Tyr Ser Ala Trp Lys Leu His Leu Leu Gln Trp Glu Glu Asp Ser
     25                  30                  35

AAT TCA GTG GTT CTT TCC TTT GAC TCC GCT GGA CAA ACA CTA GGC TCA       316
Asn Ser Val Val Leu Ser Phe Asp Ser Ala Gly Gln Thr Leu Gly Ser
 40                  45                  50                  55

GAG TAT GAT CGG TTG GGC TTC CTC CTG AAT CTG GAC TCT AAA CTG CCT       364
Glu Tyr Asp Arg Leu Gly Phe Leu Leu Asn Leu Asp Ser Lys Leu Pro
                 60                  65                  70

GCT GAA TTA GCC ACC AAG TAC GCA AAC TTT TCA GAG GGA GCT TGC AAG       412
Ala Glu Leu Ala Thr Lys Tyr Ala Asn Phe Ser Glu Gly Ala Cys Lys
                 75                  80                  85

CCT GGC TAT GCT TCA GCC TTG ATG ACG GCC ATC TTC CCC CGG TTC TCC       460
Pro Gly Tyr Ala Ser Ala Leu Met Thr Ala Ile Phe Pro Arg Phe Ser
         90                  95                 100

AAG CCA GCA CCC ATG TTC CTG GAT GAC TCC TTT CGC AAG TGG GCT AGA       508
Lys Pro Ala Pro Met Phe Leu Asp Asp Ser Phe Arg Lys Trp Ala Arg
105                 110                 115

ATC CGG GAG TTC GTG CCG CCT TTT GGG ATC AAA GGT CAA GAC AAT CTG       556
Ile Arg Glu Phe Val Pro Pro Phe Gly Ile Lys Gly Gln Asp Asn Leu
120                 125                 130                 135

ATC AAA GCC ATC TTG TCA GTC ACC AAA GAG TAC CGC CTG ACC CCT GCC       604
Ile Lys Ala Ile Leu Ser Val Thr Lys Glu Tyr Arg Leu Thr Pro Ala
                140                 145                 150

TTG GAC AGC CTC CGC TGC CGC CGC TGC ATC ATC GTG GGC AAT GGA GGC       652
Leu Asp Ser Leu Arg Cys Arg Arg Cys Ile Ile Val Gly Asn Gly Gly
                155                 160                 165
```

```
GTT CTT GCC AAC AAG TCT CTG GGG TCA CGA ATT GAC GAC TAT GAC ATT      700
Val Leu Ala Asn Lys Ser Leu Gly Ser Arg Ile Asp Asp Tyr Asp Ile
            170                 175                 180

GTG GTG AGA CTG AAT TCA GCA CCA GTG AAA GGC TTT GAG AAG GAC GTG      748
Val Val Arg Leu Asn Ser Ala Pro Val Lys Gly Phe Glu Lys Asp Val
        185                 190                 195

GGC AGC AAA ACG ACA CTG CGC ATC ACC TAC CCC GAG GGC GCC ATG CAG      796
Gly Ser Lys Thr Thr Leu Arg Ile Thr Tyr Pro Glu Gly Ala Met Gln
200                 205                 210                 215

CGG CCT GAG CAG TAC GAG CGC GAT TCT CTC TTT GTC CTC GCC GGC TTC      844
Arg Pro Glu Gln Tyr Glu Arg Asp Ser Leu Phe Val Leu Ala Gly Phe
                220                 225                 230

AAG TGG CAG GAC TTT AAG TGG TTG AAA TAC ATC GTC TAC AAG GAG AGA      892
Lys Trp Gln Asp Phe Lys Trp Leu Lys Tyr Ile Val Tyr Lys Glu Arg
            235                 240                 245

GTG AGT GCA TCG GAT GGC TTC TGG AAA TCT GTG GCC ACT CGA GTG CCC      940
Val Ser Ala Ser Asp Gly Phe Trp Lys Ser Val Ala Thr Arg Val Pro
        250                 255                 260

AAG GAG CCC CCT GAG ATT CGA ATC CTC AAC CCA TAT TTC ATC CAG GAG      988
Lys Glu Pro Pro Glu Ile Arg Ile Leu Asn Pro Tyr Phe Ile Gln Glu
265                 270                 275

GCC GCC TTC ACC CTC ATT GGC CTG CCC TTC AAC AAT GGC CTC ATG GGC     1036
Ala Ala Phe Thr Leu Ile Gly Leu Pro Phe Asn Asn Gly Leu Met Gly
280                 285                 290                 295

CGG GGG AAC ATC CCT ACC CTT GGC AGT GTG GCA GTG ACC ATG GCA CTA     1084
Arg Gly Asn Ile Pro Thr Leu Gly Ser Val Ala Val Thr Met Ala Leu
                300                 305                 310

CAC GGC TGT GAC GAG GTG GCA GTC GCA GGA TTT GGC TAT GAC ATG AGC     1132
His Gly Cys Asp Glu Val Ala Val Ala Gly Phe Gly Tyr Asp Met Ser
            315                 320                 325

ACA CCC AAC GCA CCC CTG CAC TAC TAT GAG ACC GTT CGC ATG GCA GCC     1180
Thr Pro Asn Ala Pro Leu His Tyr Tyr Glu Thr Val Arg Met Ala Ala
        330                 335                 340

ATC AAA GAG TCC TGG ACG CAC AAT ATC CAG CGA GAG AAA GAG TTT CTG     1228
Ile Lys Glu Ser Trp Thr His Asn Ile Gln Arg Glu Lys Glu Phe Leu
345                 350                 355

CGG AAG CTG GTG AAA GCT CGC GTC ATC ACT GAT CTA AGC AGT GGC ATC     1276
Arg Lys Leu Val Lys Ala Arg Val Ile Thr Asp Leu Ser Ser Gly Ile
360                 365                 370                 375

TGA GTGGCCCAG CACATGGCCA TAGAGGCCCA GGCACCACCA GGAGCAGCAG           1329
TER

CCAGCACCAC CTACACAGGA GTCTTCAGAC CCAGAGAAGG ACGGTGCCAA GGGCCCCAGG   1389

GGCAGCAAGG CCTTGGTGGA GCAGCCAGAG CTGTGCCTGC TCAGCAGCCA GTCTCAGAGA   1449

CCAGCACTCA GCCTCATTCA GCATGGGTCC TTGATGCCAG AGGGCCAGCA GGCTCCTGGC   1509

TGTGCCCAGC AGGCCCAGCA TGCAGGTGGT GGGACACTGG GCAGCAAGGC TGCTGCCGGA   1569

ATCACTTCTC CAATCAGTGT TTGGTGTATT ATCATTTTGT GAATTTGGGT AGGGGGGAGG   1629

GTAGGGATAA TTTATTTTTA AATAAGGTTG GAGATGTCAA GTTGGGTTCA CTTGCCATGC   1689

AGGAAGAGGC CCACTAGAGG GCCCATCAGG CAGTGTTACC TGTTAGCTCC CTGTGGGGCA   1749

GGAGTGCCAG GACCAGCCTG TACCTTGCTG TGGGGCTACA GGATGGTGGG CAGGATCTCA   1809

AGCCAGCCCC CTCCAGCTCA TGACACTGTT TGGCCTTTCT TGGGGAGAAG GCGGGGTATT   1869

CCCACTCACC AGCCCTAGCT GTCCCATGGG GAAACCCTGG AGCCATCCCT TCGGAGCCAA   1929

CAAGACCGCC CCAGGGCTAT AGCAGAAAGA ACTTTAAAGC TCAGGAGGGT GACGCCCAGC   1989

TCCGCCTGCT GGGAAGAGCT CCCCTCCACA GCTGCAGCTG ATCCATAGGA CTACCGCAGG   2049
```

```
CCCGGACTCA CCAACTTGCC ACATGTTCTA GGTTTCAGCA ACAAGACTGC CAGGTGGTTG     2109

GGTTCTGCCT TTAGCCTGGA CCAAAGGGAA GTGAGGCCCA AGGAGCTTAC CCAAGCTGTG     2169

GCAGCCGTCC CAGGCCACCC CCATGGAAGC AATAAAGCTC TTCCCTGTAA AAAAAAAAA      2229

AAA                                                                  2232

(2) INFORMATION FOR SEQ ID NO:10:

(i) SEQUENCE CHARACTERISTICS:
         (A) LENGTH: 38
         (B) TYPE: nucleic acid
         (C) STRANDEDNESS: double
         (D) TOPOLOGY: linear (ii) MOLECULE TYPE: other nucleic acid, synthetic DNA (xi) SEQUENCE DESCRIPTION:  SEQ ID NO:10:

CTCTGTAGGC CTTACTCCAG TGGGAGGAGG ACTCCAAT                               38

(2) INFORMATION FOR SEQ ID NO:11:

(i) SEQUENCE CHARACTERISTICS:
         (A) LENGTH: 37
         (B) TYPE: nucleic acid
         (C) STRANDEDNESS: double
         (D) TOPOLOGY: linear (ii) MOLECULE TYPE: other nucleic acid, synthetic DNA (xi) SEQUENCE DESCRIPTION:  SEQ ID NO:11:

GACTCAGGTA CCACTCAGAT GCCACTGCTT AGATCAG                                37

(2) INFORMATION FOR SEQ ID NO:12:

(i) SEQUENCE CHARACTERISTICS:
         (A) LENGTH: 34
         (B) TYPE: nucleic acid
         (C) STRANDEDNESS: double
         (D) TOPOLOGY: linear (ii) MOLECULE TYPE: other nucleic acid, synthetic DNA (xi) SEQUENCE DESCRIPTION:  SEQ ID NO:12:

CTCTCGGATA TCCCACTGTG TACCCTAATG GGTC                                   34

(2) INFORMATION FOR SEQ ID NO:13:

(i) SEQUENCE CHARACTERISTICS:
         (A) LENGTH: 36
         (B) TYPE: nucleic acid
         (C) STRANDEDNESS: double
         (D) TOPOLOGY: linear (ii) MOLECULE TYPE: other nucleic acid, synthetic DNA (xi) SEQUENCE DESCRIPTION:  SEQ ID NO:13:

GTAGACGCGG CCGCTCAGGT GAACCAAGCC GCTATG                                 36

(2) INFORMATION FOR SEQ ID NO:14:

(i) SEQUENCE CHARACTERISTICS:
         (A) LENGTH: 24
         (B) TYPE: nucleic acid
         (C) STRANDEDNESS: double
         (D) TOPOLOGY: linear (ii) MOLECULE TYPE: other nucleic acid, synthetic DNA
```

(xi) SEQUENCE DESCRIPTION: SEQ ID NO:14:

CGCCAGTCCT CCGATTGACT GAGT                                                        24

(2) INFORMATION FOR SEQ ID NO:15:

(i) SEQUENCE CHARACTERISTICS:
        (A) LENGTH: 31
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:15:

CCATGGTACC TGTGCTGTCT GGGAAGCGGG A                                                31

(2) INFORMATION FOR SEQ ID NO:16:

(i) SEQUENCE CHARACTERISTICS:
        (A) LENGTH: 40
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:16:

AAGTATAAGC TTCCATGGAT GATGATATCG CCGCGCTCGT                                       40

(2) INFORMATION FOR SEQ ID NO:17:

(i) SEQUENCE CHARACTERISTICS:
        (A) LENGTH: 40
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:17:

ATTTAAGGTA CCGAAGCATT TGCGGTGGAC GATGGAGGGG                                       40

(2) INFORMATION FOR SEQ ID NO:18:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:18:

CACCTCCGAG GCATCTTCAA CTG                                                         23

(2) INFORMATION FOR SEQ ID NO:19:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:19:

CGTTGGTATC GGCTCTCATT CATG                                                        24

(2) INFORMATION FOR SEQ ID NO:20:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:20:

GATATCGCCG CGCTCGTCGT CGAC                                        24

(2) INFORMATION FOR SEQ ID NO:21:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:21:

CAGGAAGGAA GGCTGGAAGA GTGC                                        24

α-1,3-FUCOSYLTRANSFERASE

The present application is a divisional of application Ser. No. 08/361,306, filed Nov. 29, 1994 (now U.S. Pat. No. 7,094,530, issued Aug. 22, 2006), which is a CIP of International Application PCT/JP94/00496, filed Mar. 28, 1994, which designated the U.S. and claims benefit of JP Hei. 5-69016, filed Mar. 29, 1993, the entire content of each of which is hereby incorporated by reference in this application.

FIELD OF THE INVENTION

The present invention relates to a novel species of α-1,3-fucosyltransferase, a cDNA coding for the fucosyltransferase, a recombinant vector containing the cDNA as an insert and a cell harboring the recombinant vector as well as method of producing same. The invention further relates to a method of producing carbohydrate chains using the fucosyltransferase and to a method of producing carbohydrate chains through production of the fucosyltransferase in transformed cells. Still further, the invention relates to a method of detecting the fucosyltransferase and a method of inhibiting the production of the fucosyltransferase, both using DNA coding for the α-1,3-fucosyltransferase of the invention. The α-1,3-fucosyltransferase of the invention is useful, in particular, in the production of carbohydrate chains having a useful physiological activity, for example sialyl Lewis x, and modifications thereof.

BACKGROUND ART

While proteins produced in prokaryotes, for example *Escherichia coli*, have no carbohydrate chain, proteins and lipids produced in eukaryotes, such as yeast, fungi, plant cells and animal cells, have a carbohydrate chain bound thereto in many instances.

Carbohydrate chains bound to proteins in animal cells include N-glycoside bond type carbohydrate chains (also called N-glycans) bound to an asparagine (Asn) residue in the protein and O-glycoside bond type carbohydrate chains (also called O-glycans) bound to a serine (Ser) or threonine (Thr) residue. It has recently been revealed that a certain kind of lipid containing a carbohydrate chain is covalently bound to a number of proteins and that those proteins are attached to the cell membrane through the lipid. This carbohydrate chain-containing lipid is called glycosyl phosphatidylinositol anchor.

Other carbohydrate chains, including glycosaminoglycans, are also present in animal cells. Compounds comprising a protein covalently bound to a glycosaminoglycan are called proteoglycans. The glycosaminoglycans constituting the carbohydrate chains of proteoglycans are similar in structure to O-glycans, which are carbohydrate chains of glycoproteins, but differ chemically therefrom. Glycosaminoglycans comprise repeating disaccharide units composed of glucosamine or galactosamine and a uronic acid (except for keratan sulfate which has no uronic acid residue) having sulfate residues covalently bound thereto (except for hyaluronic acid which has no sulfate residue).

Further carbohydrate chains in animal cells are present in substances called glycolipids. Sphingoglycolipids are one type of glycolipid present in animal cells. Sphingoglycolipids are composed of a carbohydrate, a long-chain fatty acid and sphingosine, a long-chain base, covalently bound together. Glyceroglycolipids are composed of a carbohydrate chain and glycerol covalently bound together.

Recent advances in molecular biology and cellular biology have made it possible to clarify the functions of carbohydrate chains. To date, a variety of functions of carbohydrate chains have been elucidated. First, carbohydrate chains play an important role in the clearance of glycoproteins in blood. It is known that erythropoietin produced by introducing the relevant gene into *Escherichia coli* retains activity in vitro but undergoes rapid clearance in vivo [Dordal et al.: Endocrinology, 116, 2293 (1985) and Browne et al.: Cold Spring Harbor Symposia on Quantitative Biology, 51, 693 (1986)]. It is known that while native human granulocyte-macrophage colony stimulating factor (hGM-CSF) has two carbohydrate chains of the N-glycoside bond type, a reduction in the number of carbohydrate chains results in a proportional increase in the rate of clearance from rat plasma [Donahue et al.: Cold Spring Harbor Symposia on Quantitative Biology, 51, 685 (1986)]. The rate of clearance and the site of clearance may vary or differ depending on the structure of the carbohydrate chain in question. Thus, it is known that hGM-CSF having a sialic acid residue undergoes clearance in the kidney while hGM-CSF lacking sialic acid has an increased rate of clearance and undergoes clearance in the liver. Alpha1-acid glycoproteins differing in carbohydrate structure and biosynthesized in the presence of various N-glycoside type carbohydrate chain biosynthesis inhibitors using a rat liver primary culture system were studied with respect to their rate of clearance from rat plasma and their rate of clearance from rat perfusate. In both cases, the rate of clearance was reduced in the order: high mannose type, carbohydrate chain-deficient type, hybrid type and composite type (natural type). It is known that the clearance from blood of tissue-type plasminogen activator (t-PA), which is used as a thrombolytic agent, is greatly influenced by the structure of its carbohydrate chain.

It is known that carbohydrate chains give protease resistance to proteins. For example, when the carbohydrate formation on fibronectin is inhibited with tunicamycin, the rate of degradation of intracellular carbohydrate chain-deficient fibronectin increases. It is also known that addition of a carbohydrate chain may result in increased heat stability or freezing resistance. In the case of erythropoietin and β-interferon, among others, the carbohydrate chain is known to contribute to increased solubility of the protein.

Carbohydrate chains also serve to maintain protein tertiary structure. It is known that when the membrane binding protein of vesicular stomatitis virus is devoid of the two naturally-occurring N-glycoside bond type carbohydrate chains, transport of the protein to the cell surface is inhibited and that when new carbohydrate chains are added to the protein, it is transported. It was revealed that, in that case, intermolecular association of the protein through disulfide bonding is induced following the elimination of carbohydrate chains and, as a result, protein transport is inhibited. When carbohydrate chains are added, the association is inhibited and the proper tertiary protein structure is maintained and protein transport becomes possible. As regards the site of addition of the new carbohydrate, it has been shown that there is a considerable amount of flexibility. In contrast, it has also been shown in certain instances that, depending on the site of carbohydrate chain introduction, the transport of a protein having a natural carbohydrate chain or chains may be completely inhibited.

Examples are also known where a carbohydrate chain serves to mask an antigenic site of a polypeptide. In the case of hGM-CSF, prolactin, interferon-γ, Rauscher leukemia virus gp70 and influenza hemagglutinin, experiments using a polyclonal antibody or a monoclonal antibody directed to a specific site on the peptide suggest that carbohydrate chains of these proteins inhibit antibody binding. Cases are also known where carbohydrate chains themselves are directly involved in the expression of activity by a glycoprotein. For instance, carbohydrates are thought to be associated with the expression of activity of such glycoprotein hormones as luteinizing hormone, follicle stimulating hormone and chorionic gonadotropin.

Carbohydrate chains serve an important function in the phenomenon of recognition between cells, between proteins or between a cell and a protein. For example, it is known that structurally different carbohydrate chains undergo clearance in vivo at different sites. It has recently been revealed that the ligand of the protein ELAM-1 (also called E-selectin), which is expressed specifically on vascular endothelial cells during an inflammatory response and promotes adhesion to neutrophils, is a carbohydrate chain called sialyl Lewis x [NeuAcα2-3Galβ1-4(Fucα1-3)GlcNAc; where NeuAc: sialic acid; Gal: galactose; Fuc: fucose; GlcNAc: N-acetylglucosamine]. The possible use of carbohydrate chains themselves or modifications thereof as drugs or the like is thus suggested [Phillips et al.: Science, 250, 1130 (1990); Goelz et al.: Trends in Glyco-science and Glycotechnology, 4, 14-24 (1992)]. Like ELAM-1, L-selectin, expressed in some T lymphocytes or neutrophils, and GMP-140 (also called P-selectin), expressed in platelets or on the membrane surface of vascular endothelial cells upon inflammatory stimulation, are associated with inflammatory responses. It is suggested that their ligand may be a carbohydrate chain analogous to sialyl Lewis x, the ELAM-1 ligand [Rosen et al.: Trends in Glycoscience and Glycotechnology, 4, 1-13 (1992); Larsen et al.: Trends in Glycoscience and Glycotechnology, 4, 25-31 (1992); Aruffo et al.: Trends in Glycoscience and Glycotechnology, 4, 146-151 (1992)]. ELAM-1, GMP-140 and L-selectin are structurally similar to one another and are collectively called selectins.

It has been suggested that, in cancer metastasis, as in inflammatory responses, ELAM-1 and GMP-140 cause adhesion of cancer cells to the vascular endothelium or aggregation of cancer cells with platelets and thereby promote cancer metastatis [Goelz et al.: Trends in Glycoscience and Glycotechnology, 4, 14-24 (1992); Larsen et al.: Trends in Glycoscience and Glycotechnology, 4, 25-31 (1992)]. This is in agreement with the finding that the level of expression of the sialyl Lewis x carbohydrate chain is high in cancer cells that are highly metastatic [Irimura et al.: Jikken Igaku (Experimental Medicine), 6, 33-39 (1988)]. ELAM-1 binds not only to sialyl Lewis x but also to a carbohydrate chain called sialyl Lewis a [NeuAcα2-3Galβ1-3(Fucα1-4)GlcNAc]. The binding affinity for sialyl Lewis a is somewhat stronger [Berg et al.: Journal of Biological Chemistry, 266, 14869-14872 (1991); Takada et al.: Biochemical and Biophysical Research Communications, 179, 713-719 (1991); Larkin et al.: Journal of Biological Chemistry, 267, 13661-13668 (1992)]. The sialyl Lewis a carbohydrate chain is also a carbohydrate chain antigen expressed upon oncogenesis of cells and is reportedly correlated with cancer metastatis [Kannagi and Takada: Jikken Igaku (Experimental Medicine), 10, 96-107 (1992)].

Based on these findings, it is expected that the sialyl Lewis x carbohydrate chain and sialyl Lewis a carbohydrate chain or derivatives thereof might produce a strong anti-inflammatory effect through their binding to ELAM-1, L-selectin or GMP-140 and, further, might inhibit cancer metastatis.

In view of the above-mentioned mechanisms of inflammatory responses and cancer metastatis, it may be possible to suppress inflammatory responses or prevent cancer metastatis by suppressing the expression of glycosyltransferases which control the synthesis of ligand carbohydrate chains recognizable by ELAM-1, L-selectin or GMP-140. The antisense RNA/antisense DNA technique [Tokuhisa: Bioscience and Industry, 50, 322-326 (1992); Murakami: Kagaku (Chemistry), 46, 681-684 (1991)] and the triple helix technique [Chubb and Hogan: Trends in Biotechnology, 10, 132-136 (1992)] are useful in suppressing the expression of a certain specific gene. For suppressing the expression of a specific glycosyltransferase using the antisense RNA/DNA technique, information is necessary about the gene or the base sequence of the gene and therefore it is important to clone the gene encoding the specific glycosyltransferase and determine the base sequence of same.

It is possible to diagnose an inflammatory disease by detecting expression of a specific glycosyltransferase in inflammatory leukocytes. In addition, it is possible to determine the metastatic potential of a tumor by determining the expression of a specific glycosyltransferase in the tumor cells. Useful for examining the expression of a specific glycosyltransferase gene are the Northern hybridization technique [Sambrook, Fritsch and Maniatis; Molecular Cloning—A Laboratory Manual, 2nd Edition, Cold Spring Harbor Laboratory Press, 1989], which uses, as a probe, the gene radioactively labeled, for example, and the polymerase chain reaction (hereinafter, "PCR") technique [Innis et al.: PCR Protocols, Academic Press, 1990]. In applying these techniques, the specific glycosyltransferase gene or knowledge of the base sequence of the gene is required. From this viewpoint as well, it is important to clone the specific glycosyltransferase gene and determine its base sequence.

JP-A-2-227075 discloses the possibility of improving the properties of physiologically active proteins, such as granulocyte colony stimulating factor (G-CSF) and prourokinase (pro-UK), by artificially introducing a carbohydrate chain into the proteins using recombinant DNA technology.

As mentioned above, it is a very important problem from an industrial viewpoint to modify the structure of the carbohydrate chain of a glycoprotein or prepare a specific carbohydrate chain or a modification thereof in large quantities.

There have been marked advances in recent years in the means for modifying carbohydrate chain structures. In particular, it is now possible to structurally modify carbohydrate chains using highly specific enzymes (exoglucosidases) that are capable of releasing carbohydrate units one by one from the end of the carbohydrate chain, or glycopeptidases or endo-glycosidases that are capable of cleaving the site of binding to the peptide chain without causing any change in either the peptide or carbohydrate chains, and accordingly, to study biological roles of carbohydrate chains in detail. The recent discovery of endoglycoceramidases that are capable of cleaving the glycolipids at the site between the carbohydrate chain and the ceramide [Ito and Yamagata: Journal of Biological Chemistry, 262, 14278 (1986)] has not only made it easy to prepare carbohydrate chains of glycolipids but has also promoted investigations into functions of glycolipids, in particular glycolipids occurring in cell surface layers. Further, it has become possible to add new carbohydrate chains using glycosyltransferases. Thus, for instance, sialic acid can be added to a carbohydrate chain terminus using sialyltransferase [Sabesan and Paulson: Journal of the American Chemical Society, 108, 2068 (1986)]. It is also possible, using various glycosyltransferases or glycosidase inhibitors, to modify carbohydrate chains that are to be added [Allan et al.: Annual Review of Biochemistry, 56, 497 (1987)]. However, there is no means available for producing glycosyltransferases for use in synthesizing carbohydrate chains. It is desirable to produce glycosyltransferases in large quantities by cloning glycosyltransferases and causing efficient expression of glycosyltransferases in host cells utilizing recombinant DNA technology.

As regards α-1,3- or α-1,4-fucosyltransferase species possibly involved in the synthesis of the sialyl Lewis x or sialyl Lewis a carbohydrate chain, the occurrence of five enzyme activities has so far been suggested [Mollicone et al.: Carbohydrate Research, 228, 265-276 (1992); Weston et al. Journal of Biological Chemistry, 267, 24575-24584 (1992)]. Among genes coding for α-1,3- or α-1,4-fucosyltransferase, the following four have reportedly been isolated: α-1,3/1,4-fucosyltransferase gene (hereinafter referred to as "Fuc-TIII" for short) [Kukowska-Latallo et al.: Genes & Development, 4, 1288-1303 (1990)] directly involved in the synthesis of the Lewis blood type antigen carbohydrate chain; α-1,3-fucosyltransferase gene named EFLT (hereinafter, "Fuc-TIV") [Goelz et al.: Cell, 63, 1349-1356 (1990)]; α-1,3-fucosyltransferase gene isolated by Weston et al. using the hybridization technique (hereinafter, "Fuc-TV") [Weston et al.: Journal of Biological Chemistry, 267, 4152-4160 (1992)]; and α-1,3-fucosyltransferase gene isolated by Weston et al. using the hybridization technique (hereinafter, "Fuc-TVI") [Weston et al.: Journal of Biological Chemistry, 267, 24575-24584 (1992)].

For the medical field, it is important to identify an α-1,3-fucosyltransferase that is directly involved in the synthesis of carbohydrate chains related to sialyl Lewis x, the ligand of ELAM-1 or GMP-140, in inflammatory leucocytes such as granulocytes.

Among the above-mentioned four α-1,3-fucosyltransferase genes Fuc-TIV by itself is apparently incapable of synthesizing the sialyl Lewis x carbohydrate chain, which is the ligand of ELAM-1, or the sialyl Lewis a carbohydrate chain [Lowe et al.: Journal of Biological Chemistry, 266, 17467-17477 (1991); Kumar et al.: Journal of Biological Chemistry, 266, 21777-21783 (1991)] and an α-1,3-fucosyltransferase directly involved in ELAM-1 ligand synthesis has not yet been obtained from human granulocytic or monocytic cells, for example the human granulocytic cell line HL-60 reportedly adhering to ELAM-1 [Lobb et al.: Journal of Immunology, 147, 124-129 (1991)].

In view of the foregoing, it is important to identify and isolate an α-1,3-fucosyltransferase that is directly involved in ELAM-1 ligand synthesis from human granulocytic or monocytic cells so that efficient in vitro or in vivo production of carbohydrate ligands directly involved in in vivo adhesion to ELAM-1 can be carried out. It is also important from the standpoint of detection of α-1,3-fucosyltransferase or inhibition of its production in sites of inflammation by the polymerase chain reaction technique utilizing DNA coding for the fucosyltransferase.

It is an object of the present invention to provide a novel α-1,3-fucosyltransferase species, a cDNA coding for the fucosyltransferase and a vector containing the cDNA, with which glycoproteins or glycolipids containing ligand carbohydrate chains of selectins, such as ELAM-1, can be efficiently produced in animal cells, in particular Namalwa cells. Another object is to provide a DNA coding for the fucosyltransferase useful in the treatment of diseases, such as inflammation, by inhibiting the expression of the fucosyltransferase using, for example, the above-mentioned antisense RNA/DNA technique or in the diagnosis of such diseases using, for example, the Northern hybridization or PCR technique.

DISCLOSURE OF THE INVENTION

The present inventors constructed a cDNA library by inserting cDNA, synthesized using mRNA extracted from the monocytic cell line THP-1 as a template, into an expression cloning vector, introduced the cDNA library into cells, isolated, from among the cells obtained, cells strongly reactive with an antibody to the sialyl Lewis x carbohydrate chain which is the ligand of ELAM-1, utilizing a fluorescence activated cell sorter (hereinafter, "FACS") and thus cloned a gene coding for α-1,3-fucosyltransferase. Further, they introduced the fucosyltransferase-encoding gene into Namalwa cells and caused expression thereof. The inventors found that the gene expresses a novel α-1,3-fucosyltransferase species, further that the amount of the sialyl Lewis x carbohydrate chain on the cell surface increases and that the fucosyltransferase is localized in granulocytic cells or monocytic cells that are producing the sialyl Lewis x carbohydrate chain.

The present invention is described in detail as follows.

The present invention relates, in one embodiment, to a novel α-1,3-fucosyltransferase species comprising the amino acid sequence defined in SEQ ID NO:2. The invention further relates to a cDNA coding for the fucosyltransferase, to a recombinant vector harboring the DNA, and to a cell containing the recombinant vector. The α-1,3-fucosyltransferase of the present invention is a glycosyltransferase having N-acetyl-glucosaminide fucosyltransferase activity that is capable of adding fucose, in α1→3 linkage, to N-acetyl-glucosamine contained in acceptor carbohydrate chains. The α-1,3-fucosyltransferase of the present invention, when expressed in Namalwa cells, has activity such that it increases the amount of the sialyl Lewis x carbohydrate chain, which is the ligand of ELAM-1.

cDNA sequences coding for the α-1,3-fucosyltransferase of the present invention include (a) DNA comprising the base sequence defined in SEQ ID NO:1; (b) DNA containing a base sequence different from the base sequence defined in SEQ ID NO:1, the difference being due to the availability of a plurality of codons for one amino acid or to spontaneous mutation occurring in individual animals including human; and (c) a DNA derived from the DNA defined in (a) or (b) by mutation, such as substitution, deletion or insertion mutation, that does not cause loss of the α-1,3-fucosyltransferase activity, for example, DNA encoding a modified amino acid sequence derived from the sequence defined in SEQ ID NO:2 from which the first to 38th amino acid residues from the N-terminus are deleted as shown in the following Example or DNA homologous to the α-1,3-fucosyltransferase-encoding DNA defined in (a) or (b). Homologous DNA means a DNA obtainable by the colony hybridization or plaque hybridization technique using a DNA containing the base sequence defined in SEQ ID NO:1 as a probe and specifically means a DNA identifiable by performing hybridization at 65° C. in the presence of 0.7-1.0 M NaCl using a filter with a colony- or plaque-derived DNA fixed thereon and then washing the filter in a 0.1-fold to 2-fold concentrated SSC solution (1-fold concentrated SSC solution comprising 150 mM NaCl and 15 mM sodium citrate) at 65° C. The hybridization procedure is described in Molecular Cloning—A Laboratory Manual, 2nd Edition, edited by Sambrook, Fritsch and Maniatis, Cold Spring Harbor Laboratory Press, 1989. The invention also relates to α-1,3-fucosyltransferase species encoded by the DNAs defined above in (a), (b) and (c).

The following describes a method of producing cDNA coding for the α-1,3-fucosyltransferase of the present invention, taking the cDNA defined above in (a) as an example.

A cDNA library is constructed by inserting cDNA synthesized using mRNA extracted from the monocytic cell line THP-1 as a template into an expression cloning vector. This cDNA library is introduced into animal cells or insect cells, then cells strongly reacting with an antibody against the sialyl Lewis x carbohydrate chain (ligand of ELAM-1) are concentrated and isolated utilizing a FACS and the desired α-1,3-fucosyltransferase-encoding cDNA is isolated from the cells.

Animal cells suitable for use in the above process can be any cells provided that they are animal cells in which the α-1,3-fucosyltransferase of the present invention is expressed. Thus, for instance, the human monocytic cell line THP-1 (ATCC TIB 202), human monocytic cell line U-937 (ATCC CRL 1593) or human granulocytic cell line HL-60 (ATCC CCL 240) can be used. The vector into which the cDNA synthesized using the mRNA extracted from these cells as a template is to be inserted can be any vector provided that it allows insertion thereinto and expression of the cDNA. Thus, for instance, pAMoPRC3Sc or the like can be used. The animal or insect cells into which the cDNA library constructed using the vector are introduced can be any cells provided that they allow introduction therein and expression of the cDNA library. Thus, for instance, human Namalwa cells [Hosoi et al.: Cytotechnology, 1, 151 (1988)] or the like can be used. In particular, a direct expression cloning system using Namalwa cells as the host is advantageous in that the efficiency of introduction of a cDNA library into host Namalwa cells is very high and in that the plasmids (cDNA library) introduced can be maintained extrachromosomally in the system and can be readily recovered from the cells obtained by screening using a carbohydrate chain-specific antibody and a FACS. Therefore, this system is preferred. The anti-sialyl Lewis x carbohydrate chain antibody to be used in the practice of the invention can be any antibody provided that it reacts with the sialyl Lewis x carbohydrate chain. Thus, for instance, KM93, which is an anti-sialyl Lewis x antibody [Anticancer Research, 12, 27 (1992)] can be used. The animal cells, after introduction thereinto of the cDNA library, are fluorescence-labeled using the anti-sialyl Lewis x antibody and then cells showing increased binding to the antibody are separated and enriched using a FACS. From the cells thus obtained, a plasmid or DNA fragment containing the cDNA coding for the α-1,3-fucosyltransferase of the present invention is recovered using, for example, known methods, e.g. the Hart method [Robert F. Margolskee et al.: Molecular and Cellular Biology, 8, 2837 (1988)]. Plasmids of the invention containing a cDNA coding for the enzyme include pUC119-TH21R. *Escherichia coli* JM105/pUC119-TH21R, an *Escherichia coli* strain harboring pUC119-TH21R, was deposited on Feb. 18, 1993, at the National Institute for Bioscience and Human Technology, Agency of industrial Science and Technology, of 1-3, Higashi 1-chome, Tsukuba-shi, Ibiraki 305, JAPAN, under the deposit number FERM BP-4193 (Budapest Treaty deposit).

The DNA defined above in (b) or (c) can be produced using the well-known recombinant DNA technology [JP-A-2-227075; Molecular Cloning—A Laboratory Manual, 2nd Edition, Cold Spring Harbor Laboratory Press, 1989; etc.], such as hybridization techniques or methods of introducing mutations into DNA, based on the α-1,3-fucosyltransferase-encoding cDNA obtained by the method described above. The α-1,3-fucosyltransferase-encoding cDNA of the present invention can also be produced by chemical synthesis.

The α-1,3-fucosyltransferase of the present invention can be produced by constructing a recombinant vector by inserting DNA coding for the α-1,3-fucosyltransferase of the present invention as obtained, for example, by the method described above, into an appropriate vector and in operable linkage with a suitable promoter, introducing the recombinant vector into host cells and cultivating the cells obtained. The host cells to be used here can be any host cells suitable for use in recombinant DNA technology, for example prokaryotic cells, animal cells, yeasts, fungi and insect cells. An example of a suitable prokaryotic cell is *Escherichia coli*, CHO cells (Chinese hamster cells), COS cells (sminian cells) and Namalwa cells (human cells) are examples of suitable animal cells.

Vectors into which DNA coding for the α-1,3-fucosyltransferase of the present invention are inserted can be any vector provided that the vector allows insertion therein of the fucosyltransferase-encoding DNA and expression of the DNA in host cells. pAGE107 [JP-A-3-22979; Miyaji et al.: Cytotechnology, 3, 133 (1990)], pAS3-3 (JP-A-2-227075), pAMoERC3Sc, and CDM8 [Brian Seed et al.: Nature, 329, 840 (1987)] are examples. For the expression of the enzyme of the present invention in *Escherichia coli*, a plasmid is preferably used. The foreign DNA is inserted into the plasmid so that it is operably linked to a promoter with potent transcription activity, for example the trp promoter, and so that the distance between the Shine-Dalgarno sequence (hereinafter, "SD sequence") and the initiation codon is of an appropriate length (for example 6-18 bases). Plasmids pKYP10 (JP-A-58-110600), pLSA1 [Miyaji et al.: Agricultural and Biological Chemistry, 53, 277 (1989)] and pGEL1 [Sekine et al.: Proceedings of the National Academy of Sciences of the U.S.A., 82, 4306 (1985)] are specific examples.

Recombinant DNA techniques to be used in the practice of the invention include those described in JP-A-2-227075 or those described in Sambrook, Fritsch, Maniatis et al.: Molecular Cloning—A Laboratory Manual, 2nd Edition, Cold Spring Harbor Laboratory Press, 1989. A number of commercially available kits can be used for mRNA isolation and cDNA library construction. Known methods can be used for introducing the DNA into animal cells. The electroporation method [Miyaji et al.: Cytotechnology, 3, 133 (1990)], the calcium phosphate method (JP-A-2-227075) and the lipofection method [Philip L. Felgner et al.: Proceedings of the National Academy of Sciences of the U.S.A., 84, 7413 (1987)] are examples. Transformant isolation and cultivation can be performed essentially according to the method described in JP-A-2-227075 or JP-A-2-257891.

Suitable methods of producing the α-1,3-fucosyltransferase include the method of intracellular production in a host, the method of extracellular production or the method of production on a host cell membrane external layer. The site of production varies depending on the kind of host cell used and the form of the glycosyltransferase to be produced. In cases where animal cells are used as the host and a glycosyltransferase is produced in its native form, the enzyme is generally produced within the host cells or on the host cell membrane external layer and a portion of the enzyme produced is cleaved with protease and secreted extracellularly. The gene recombination technique of Paulson et al. [C. Paulson et al.: The Journal of Biological Chemistry, 264, 17619 (1989)] and Low et al. [John B. Lowe et al. Proceedings of the National Academy of Sciences of the U.S.A., 86, 8227 (1989); John B. Lowe et al.: Genes & Development, 4, 1288 (1990)] can be used to cause production of the enzyme in a form composed of a glycosyltransferase portion containing the active site and a signal peptide added thereto.

Production of the enzyme can be increased by utilizing a gene amplification system using the dihydrofolate reductase gene, for example, as described in JP-A-2-227075.

Alpha-1,3-fucosyltransferase produced in accordance with the present invention can be purified using ordinary methods of purifying glycosyltransferases [J. Evan. Sadler et al.: Methods of Enzymology, 83, 458]. When produced in *Escherichia coli*, the enzyme can be efficiently purified by a combination of the above method and the method described in JP-A-63-267292. It is also possible to produce the enzyme of the present invention in the form of a fusion protein and to purify the same by affinity chromatography using a substance having affinity for the fused protein. For example, the enzyme of the present invention can be produced fused with protein A. Such a protein can be purified by affinity chromatography using immunoglobulin G, essentially according to the method of Lowe et al. [John B. Lowe et a.: Proceedings of the National Academy of Sciences of the U.S.A., 86, 8227 (1989); John B. Lowe et al.: Genes & Development, 4, 1288 (1990). It is also possible to purify the enzyme by affinity chromatography using an antibody to the enzyme itself.

The fucosyltransferase activity can be determined according to the known methods [J. Evan. Sadler et al.: Methods in Enzymology, 83, 458; Naoyuki Taniguti et al.: Methods in Enzymology, 179, 397].

Carbohydrate chains can be synthesized in vitro using the α-1,3-fucosyltransferase of the present invention. For example, GlcNAc in the lactosamine structure (Galβ1→4GlcNAc structure) in glycoproteins, glycolipids or oligosaccharides can be provided with fucose in α1→3 linkage. Further, glycoproteins, glycolipids or oligosaccharides which serve as substrates, when treated with the α-1,3-fucosyltransferase of the present invention, can be modified for conversion of the carbohydrate chain structure at the nonreducing end to the sialyl Lewis x structure.

By using DNA coding for the α-1,3-fucosyltransferase of the present invention and causing simultaneous production of the fucosyltransferase and a glycoprotein, glycolipid or oligosaccharide having a useful physiological activity in animal or insect cells which are producing a carbohydrate chain to serve an acceptor substrate of said fucosyltransferase, it is possible to cause the α-1,3-fucosyltransferase produced to act on the glycoprotein, glycolipid or oligosaccharide in the cells to produce, in the cells, a glycoprotein, glycolipid or oligosaccharide having a modified carbohydrate chain structure.

Furthermore, it is also possible to excise, by known enzymatic or chemical techniques, a part of the oligosaccharide from the glycoprotein, glycolipid or oligosaccharide having a modified carbohydrate chain structure as produced in the above manner.

The DNA coding for the α-1,3-fucosyltransferase of the present invention can be used not only to effect modification of a carbohydrate chain of a protein or glycolipid or to effect efficient production of a specific carbohydrate chain, but also to treat diseases, such as inflammation and cancer metastasis utilizing, for example, antisense RNA/DNA techniques. Such DNA can also be used in the diagnosis of such diseases, for example, utilizing Northern hybridization or PCR techniques.

For instance, DNA coding for the α-1,3-fucosyltransferase of the present invention can be used to prevent expression of the fucosyltransferase by antisense RNA/DNA technology [Tokuhisa: Bioscience and Industry, 50, 322-326 (1992); Murakami: Kagaku (Chemistry), 46, 681-684 (1991); Miller: Biotechnology, 9, 358-362 (1992); Cohen: Trends in Biotechnology, LO, 87-91 (1992); Agrawal: Trends in Biotechnology, 10, 152-158 (1992)] or triple helix techniques [Chubb and Hogan: Trends in Biotechnology, 10, 132-136 (1992)]. More specifically, based on a part of the base sequence of the DNA coding for the α-1,3-fucosyltransferase of the present invention, preferably a base sequence of 10-50 bases in length as occurring in the translation initiation region, an oligonucleotide can be designed and prepared and administered in viva, under conditions such that production of the fucosyltransferase is suppressed. The base sequence of the synthetic oligonucleotide can be one that is in complete agreement with a part of the base sequence of the antisense strand of the sequence of the present invention or one that is modified without causing loss of its ability to inhibit the expression of the fucosyltransferase. When the triple helix technique is employed, the base sequence of the synthetic oligonucleotide can be designed based on the base sequence of both the sense and antisense strands.

It is also possible to detect the production of the α-1,3-fucosyltransferase of the present invention using the Northern hybridization or PCR technique. For detecting the production of the α-1,3-fucosyltransferase of the present invention using the Northern hybridization or PCR technique, the DNA coding for the α-1,3-fucosyltransferase of the present invention or a synthetic oligonucleotide synthesized based on the base sequence thereof can be used. Northern hybridization and PCR techniques can be carried out in a conventional manner [Sambrook, Fritsch and Maniatis: Molecular Cloning—A Laboratory Manual, 2nd Edition, Cold Spring Harbor Laboratory Press, 1989; Innis et al.: PCR protocols, Academic Press, 1990].

The symbols used in the figures respectively have the following meanings:
dhfr: Dihydrofolate reductase gene
hG-CSF: Human granulocyte colony stimulating factor gene
bp: Base pairs
kb: Kilobase pairs
G418/Km: Transposon 5 (Tn 5)-derived G418/kanamycin resistance gene
hyg: Hygromycin resistance gene
Ap: pER322-derived ampicillin resistance gene
Tc: pBR322-derived tetracycline resistance gene
P1: pER322-derived P1 promoter
Ptk: Herpes simplex virus (HSV) thymidine kinase (tk) gene promoter
Sp.βG: Rabbit β globin gene splicing signal
A.βG: Rabbit β globin gene poly(A) addition signal
A.SE: Simian virus 40 (SV40) early gene poly(A) addition signal
Atk: Herpes simplex virus (HSV) thymidine kinase (tk) gene poly(A) addition signal
Pse: Simian virus 40 (SV40) early gene promoter
Pmo: Moloney murine leukemia virus long terminal repeat (LTR) promoter
HTLV-1: Human T cell leukemia virus type-1 (HTLV-1) gene EBNA-1 Epstein-Barr virus EBNA-1 gene
oriP: Epstein-Barr virus replication origin
ori: pUC119 replication origin
Lac'Z: Part of *Escherichia coli* β galactosidase gene
IG: M13 phage DNA intergenic region
G-CSF der.: Human granulocyte colony stimulating factor derivative gene
S: Gene portion coding for human granulocyte colony stimulating factor signal peptide
A or ProA: Gene portion coding for binding region of *Staphylococcus aureus* protein A to IgG
TH21: α-1,3-Fucasyltransferase gene obtained from THP-1 cells (full-length gene or active region gene)

Certain aspects of the invention are described in greater detail in the nonlimiting Examples that follow.

EXAMPLE 1

Cloning of α-1,3-fucosyltransferase cDNA from Cells of Human Monocytic Cell Line THP-1

1. Construction of Direct Expression Cloning Vectors pAMoERC3Sc and pAMoPRC3Sc pAMOERC3Sc was constructed according to steps (1) to (14) described below.

Figure 1:
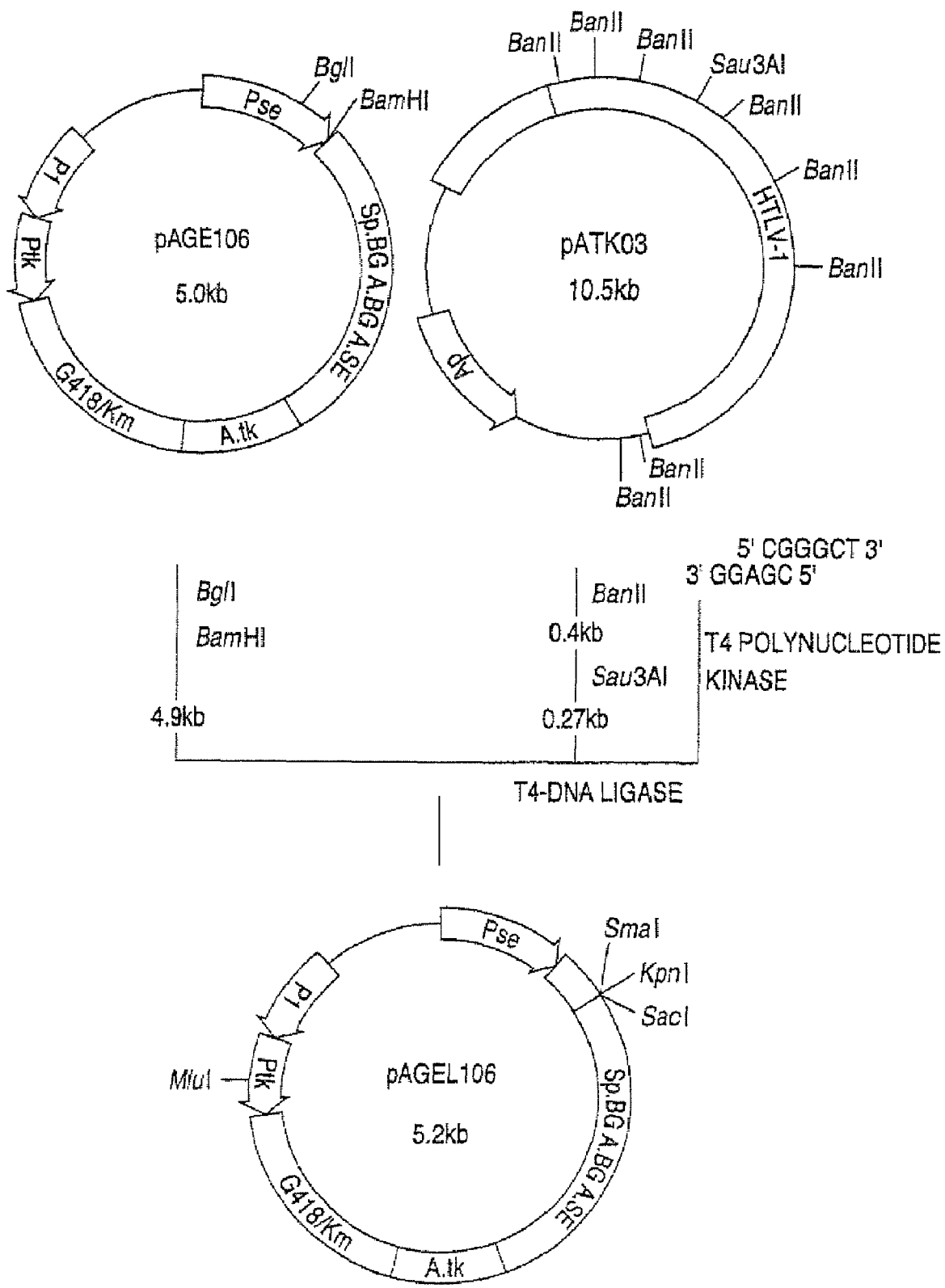
FIG. 1 shows a construction scheme for the plasmid pAGEL106.

(1) Construction of pAGEL106 (cf. FIG. 1)

A plasmid, pAGEL106, having a promoter resulting from fusion of the simian virus 40 (SV40) early gene promoter and parts of the R and U5 regions of the long terminal repeat (LTR) of the human T-cell leukemia virus type-1 (HTLV-1) was constructed. A DNA fragment [BanII-Sau3A fragment (0.27 kb)] containing parts of the R and U5 regions was excised from pATK03 and inserted into pAGE106 between BqlI-BamHI sites via a synthetic linker.

pAGE106 (JP-A-2-227075) (1 µg) was dissolved in 30 µl of a buffer comprising 10 mM Tris-HCl (pH 7.5), 6 mM MgCl$_2$, 100 mM NaCl and 6 mM 2-mercaptoethanol (hereinafter, "Y-100 buffer"), 10 units of BglI (Takara Shuzo; unless otherwise specified, the restriction enzymes mentioned hereinafter were products of Takara Shuzo) and 10 units of BamHI were added and the digestion reaction was carried out at 37° C. for 2 hours. The reaction mixture was subjected to agarose gel electrophoresis and a DNA fragment of about 4.9 kb was recovered.

Separately, 1 µg of pATK03 [Shimizu et al.: Proceedings of the National Academy of Sciences of the U.S.A., 80, 3618 (1983)] was dissolved in 30 µl of Y-100 buffer, 10 units of BanII was added and the digestion reaction was carried out at 37° C. for 2 hours. The reaction mixture was subjected to agarose gel electrophoresis and a DNA fragment of about 0.4 kb was recovered. The DNA fragment recovered was dissolved in 30 µl of Y-100 buffer, 10 units of Sau3AI was added and the digestion reaction was carried out at 37° C. for 2 hours. The reaction mixture was subjected to agarose gel electrophoresis and a DNA fragment of about 0.27 kb was recovered.

Further, separately, the following DNA linker was synthesized and used for linking the BglI and BanII cleavage sites together.

```
5'-CGGGCT-3'  (6 mer)

3'-GGAGC-5'   (5 mer)
```

The 5 mer and 6 mer single-stranded DNAs for preparing the DNA linker were synthesized using an Applied Biosystems model 380A DNA synthesizer. The DNA synthesized (0.2 μg each) were dissolved in 40 μl of a buffer comprising 50 mM Tris-HCl (pH 7.5), 10 mM MgCl$_2$, 5 mM dithiothreitol (hereinafter, DTT), 0.1 nM EDTA and 1 mM ATP (hereinafter, "T4 kinase buffer") 30 units of T4 polynucleotide kinase (Takara Shuzo; hereinafter the same shall apply) was added and the phosphorylation reaction was carried out at 37° C. for 2 hours.

The pAGE106-derived BglI-BamHI fragment (4.9 kb; 0.2 μg) and pATK03-derived BanII-Sau3A fragment (0.27 kb; 0.01 μg) respectively obtained as described above were dissolved in 30 μl of a buffer containing 66 mM Tris-HCl (pH 7.5), 6.6 mM MgCl$_2$, 10 mM DTT and 0.1 mM adenosine triphosphate (hereinafter, ATP) (hereinafter, "T4 ligase buffer"), 0.01 μg of the DNA linker mentioned above and 175 units of T4 DNA ligase (Takara Shuzo; hereinafter the same shall apply) were added and the ligation reaction was carried out at 12° C. for 16 hours.

The reaction mixture was used to transform *Escherichia coli* HB101 [Bolivar et al: Gene, 2, 75 (1977)] by the method of Cohen et al. [S. N. Cohen et al.: Proceedings of the National Academy of Sciences of the U.S.A., 69, 2110 (1972)] (hereinafter, this method was used for transforming *Escherichia coli*) and an ampicillin-resistant strain was obtained. From this transformant, a plasmid was isolated by a known method [H. C. Birnboim et al.: Nucleic Acids Research, 7, 1513 (1979)] (hereinafter this method was used for plasmid isolation). This plasmid was named pAGEL106 and its structure was identified by digestion with restriction enzymes.

Figure 2:
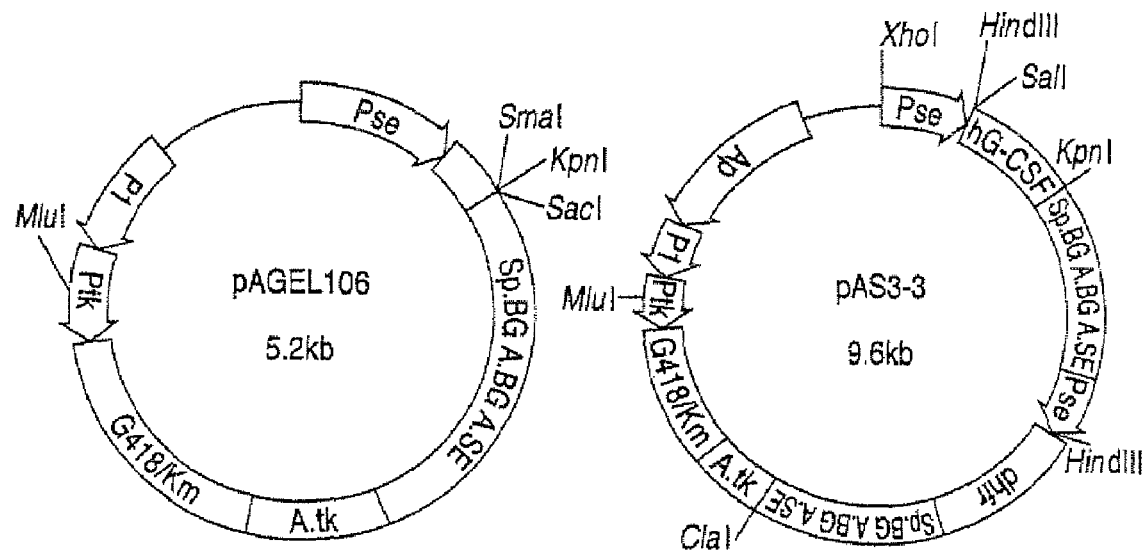
FIG. 2 shows a construction scheme for the plasmid pASLB3-3-1.
Figure 2:
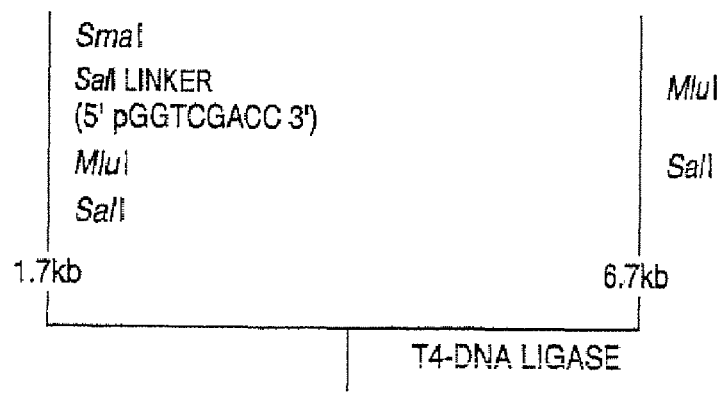
Figure 2:
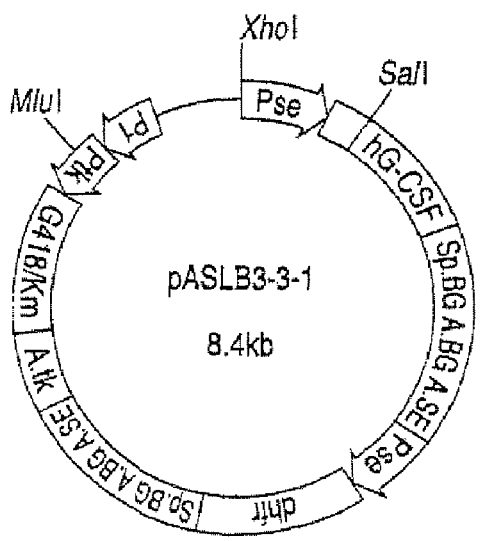

(2) Construction of pASLB3-3-1 (cf. FIG. 2)

A human granulocyte colony stimulating factor (hG-CSF) expression plasmid, pASLB3-3-1, having a promoter resulting from fusion of the SV40 early gene promoter and parts of the R and U5 regions of the long terminal repeat (LTR) of HTLV-1 was constructed in the following manner.

pAGEL106 (0.5 μg) obtained in (1) was dissolved in 30 μl of a buffer comprising 10 mM Tris-HCl (pH 7.5), 6 mM MgCl$_2$, 20 mM KCl and 6 mM 2-mercaptoethanol (hereinafter, "K-20 buffer"), 10 units of SmaI was added and the digestion reaction was carried out at 37° C. for 2 hours. After precipitation with ethanol, the precipitate was dissolved in 30 μl of T4 ligase buffer, 0.01 μg of a SalI linker (5'-pGGTC-GACC-3'; Takara Shuzo) and 175 units of T4 DNA ligase were added and the ligation reaction was carried out at 12° C. for 16 hours. After precipitation with ethanol, the precipitate was dissolved in 30 μl of a buffer comprising 10 mM Tris-HCl (pH 7.5), 6 mM MgCl$_2$, 175 mM NaCl and 6 mM 2-mercaptoethanol (hereinafter, "Y-175 buffer"), 10 units of SalI and 10 units of MluI were added and the digestion reaction was carried out at 37° C. for 2 hours. The reaction mixture was subjected to agarose gel electrophoresis and a DNA fragment of about 1.7 kb was recovered.

Separately, 1 μg of pAS3-3 (JP-A-2-227075) was dissolved in 30 μl of Y-175 buffer, 10 units of SalI and 10 units of MluI were added and the digestion reaction was carried out at 37° C. for 2 hours. The reaction mixture was subjected to agarose gel electrophoresis and a DNA fragment of about 6.7 kb was recovered.

The pAGEL106-derived MluI-SalI fragment (1.7 kg; 0.1 μg) and pAS3-3-derived MluI-SalI fragment (6.7 kb; 0.2 μg) respectively obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLB3-3-1 and its structure was identified by digestion with restriction enzymes.

Figure 3:
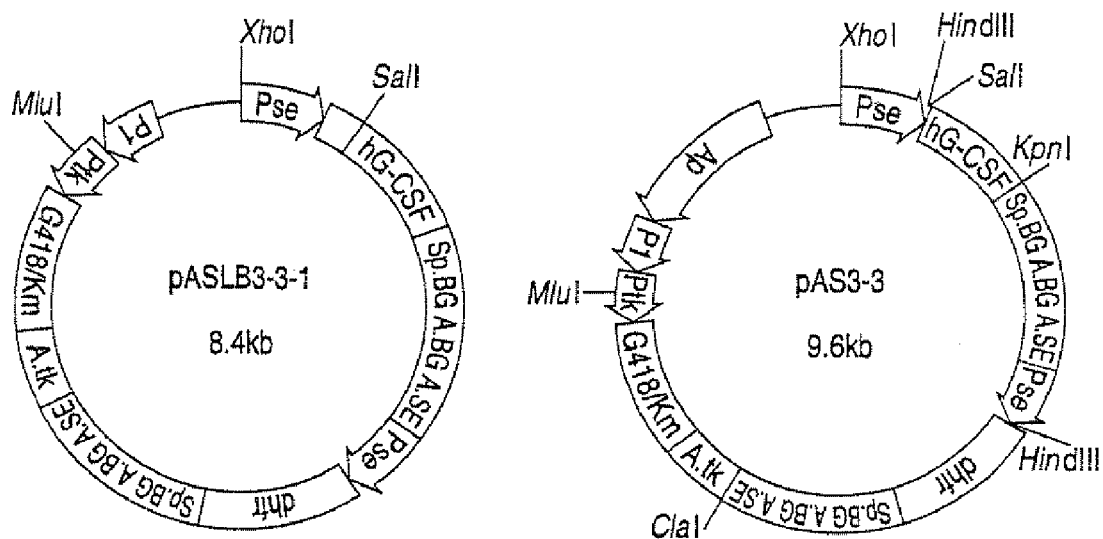
FIG. 3 shows a construction scheme for the plasmid pASLB3-3.
Figure 3:
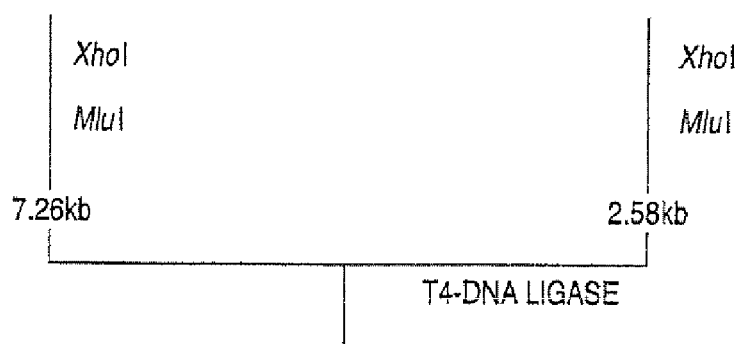
Figure 3:
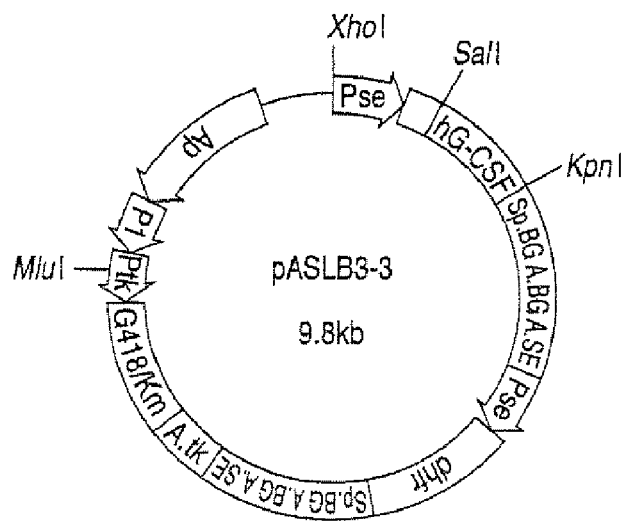

(3) Construction of pASLB3-3 (cf. FIG. 3)

For constructing a plasmid, pASLB3-3, by introducing the ampicillin resistance gene into pASLB3-3-1, an ampicillin resistance gene-containing DNA fragment [XhoI-MluI fragment (7.26 kb)] of pAS3-3 was introduced into pASLB3-3-1 between the XhoI and MluI sites.

pASLB3-3-1 (1 μg) obtained in (2) was dissolved in 30 μl of a buffer comprising 10 mM Tris-HCl (pH 7.5), 6 mM MgCl$_2$, 150 mM NaCl and 6 mM 2-mercaptoethanol (hereinafter, "Y-150 buffer"), 10 units of XhoI and 10 units of MluI and the digestion reaction was carried out at 37° C. for 2 hours. The reaction mixture was subjected to agarose gel electrophoresis and a DNA fragment of about 7.26 kb was recovered.

Separately, 1 μg of pAS3-3 (JP-A-2-227075) was dissolved in 30 μl of Y-150 buffer, 10 units of XhoI and 10 units of MluI were added and the digestion reaction was carried out at 37° C. for 2 hours. The reaction mixture was subjected to agarose gel electrophoresis and a DNA fragment of about 2.58 kb was recovered.

The pASLB3-3-1-derived XhoI-MluI fragment (7.26 kb; 0.2 μg) and pAS3-3-derived XhoI-MluI fragment (2.58 kb; 0.1 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method and its structure was identified by digestion with restriction enzymes. This plasmid was named pASLB3-3.

Figure 4:
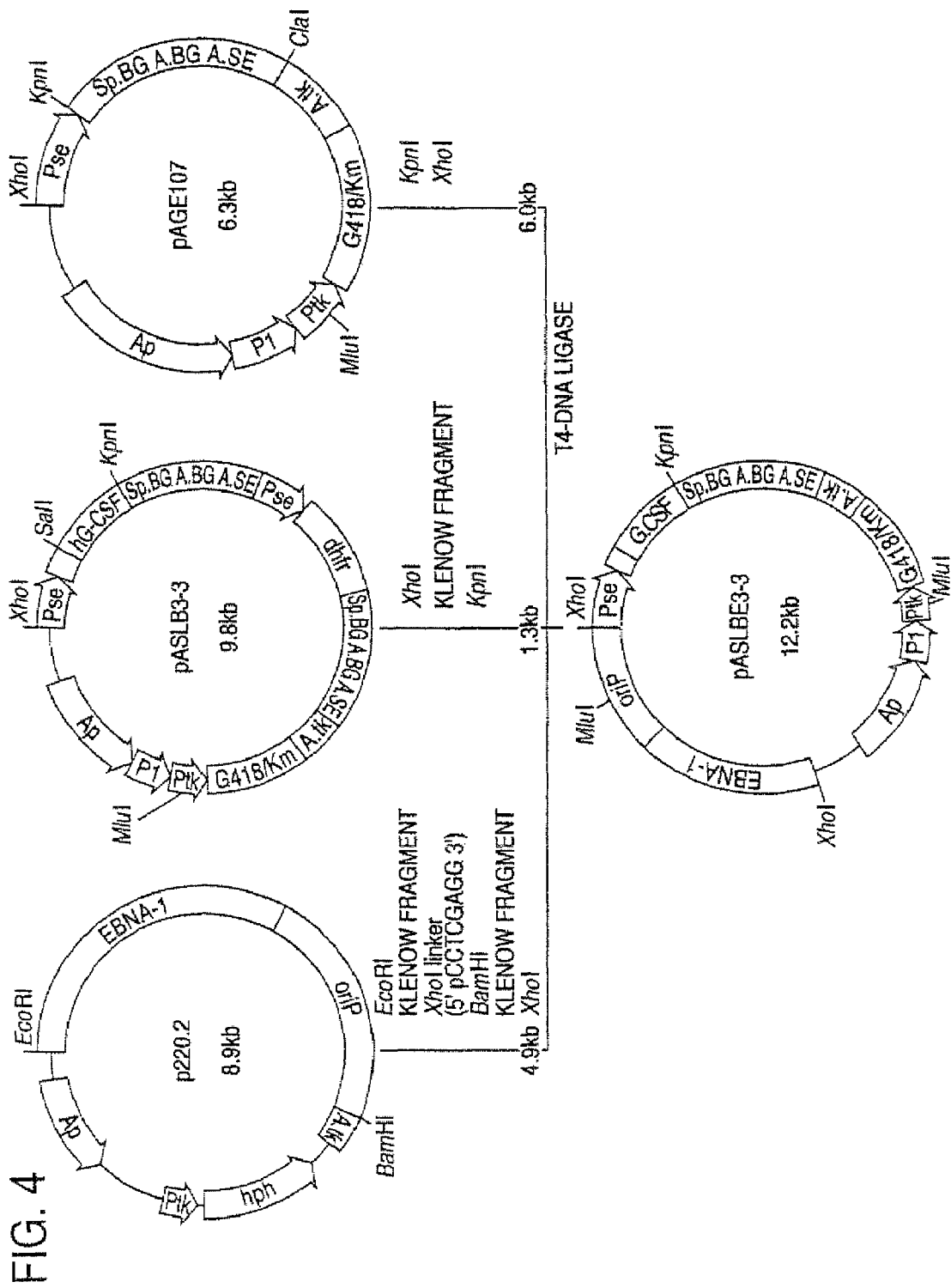
FIG. 4 shows a construction scheme for the plasmid pASLB3-3.

(4) Construction of pASLBE3-3 (cf. FIG. 4)

A plasmid, pASLBE3-3, was constructed in the manner mentioned below by eliminating from pASLB3-3 the dihydrofolate reductase (dhfr) expression unit and, instead, introducing thereinto the replication origin (oriP) and the EBNA-1 gene (acting trans on the oriP to induce replication) of the Epstein-Barr virus. The oriP and EBNA-1 genes used were those excised from a plasmid p220.2 produced by incorporating a multicloning site-containing SmaI-HaeIII fragment derived from pUC12 [Messing et al.: Methods in Enzymology, 101 20 (1983)] into p201 [Bill Sugden et al.: Nature, 313, 812 (1985)] at the NarI site thereof.

p220.2 (1 μg) was dissolved in 30 μl of Y-100 buffer, 20 units of EcoRI was added and the digestion reaction was carried out at 37° C. for 2 hours. After precipitation with ethanol, the precipitate was dissolved in 30 μl of DNA polymerase I buffer [50 mM Tris-HCl (pH 7.5), 10 mM MgCl$_2$, 0.1 mM dATP (deoxyadenosine triphosphate), 0.1 mM dCTP (deoxycytidine triphosphate), 0.1 mM dGTP (deoxyguanosine triphosphate), 0.1 mM TTP (thymidine triphosphate)], 6 units of *Escherichia coli*-derived DNA polymerase I Klenow fragment was added and the reaction was carried out at 37° C. for 60 minutes to convert the 5' cohesive end formed upon EcoRI digestion to a blunt end. The reaction was terminated by extraction with phenol. After extraction with chloroform and precipitation with ethanol, the precipitate was dissolved in 20 μl of T4 ligase buffer, 0.05 μg of an XhoI linker (5'-pCCTCGAGG-3'; Takara Shuzo) and 175 units of T4 DNA ligase were added and the ligation reaction was carried out at 12° C. for 16 hours. After precipitation with ethanol, the precipitate was dissolved in 30 μl of Y-100 buffer, 10 units of BamHI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end resulting from BamHI digestion to a blunt end. The reaction was terminated by extraction with phenol. After extraction with chloroform and precipitation with ethanol, the precipitate was dissolved in 30 µl of Y-100 buffer, 10 units of XhoI was added and the digestion reaction was carried out at 37° C. for 2 hours. The reaction mixture was subjected to agarose gel electrophoresis and a DNA fragment of about 4.9 kb was recovered.

Separately, pASLB3-3 (1 µg) obtained in (3) was dissolved in 30 µl of Y-100 buffer, 20 units of XhoI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end resulting from XhoI digestion to a blunt end. The reaction was terminated by extraction with phenol. After extraction with chloroform and precipitation with ethanol, the precipitate was dissolved in 30 µl of a buffer comprising 10 mm Tris-HCl (pH 7.5), 6 mM $MgCl_2$ and 6 mM 2-mercaptoethanol (hereinafter, "Y-0 buffer"), 20 units of KpnI was added and the digestion reaction was carried out at 37° C. for 2 hours. The reaction mixture was subjected to agarose gel electrophoresis and a DNA fragment of about 1.3 kb was recovered.

Further, separately, 1 µg of pAGE107 [JP-A-3-22979; Miyaji et al.: Cytotechnology, 3, 133 (1990)] was dissolved in 30 µl of Y-0 buffer, 20 units of KpnI was added and the digestion reaction was carried out at 37° C. for 2 hours. Then, NaCl was added to an NaCl concentration of 100 mM, 20 units of XhoI was added and the digestion reaction was further carried out at 37° C. for 2 hours. The reaction mixture was subjected to agarose gel electrophoresis and a DNA fragment of about 6.0 kb was recovered.

The p220.2-derived XhoI-BamHI (blunt end) fragment (4.9 kb; 0.2 µg), pASLB3-3-derived XhoI (blunt end)-KpnI fragment (1.3 kb; 0.1 µg) and pAGE107-derived KpnI-XhoI fragment (6.0 kb; 0.2 µg) respectively obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBE3-3 and its structure was identified by digestion with restriction enzymes.

Figure 5:
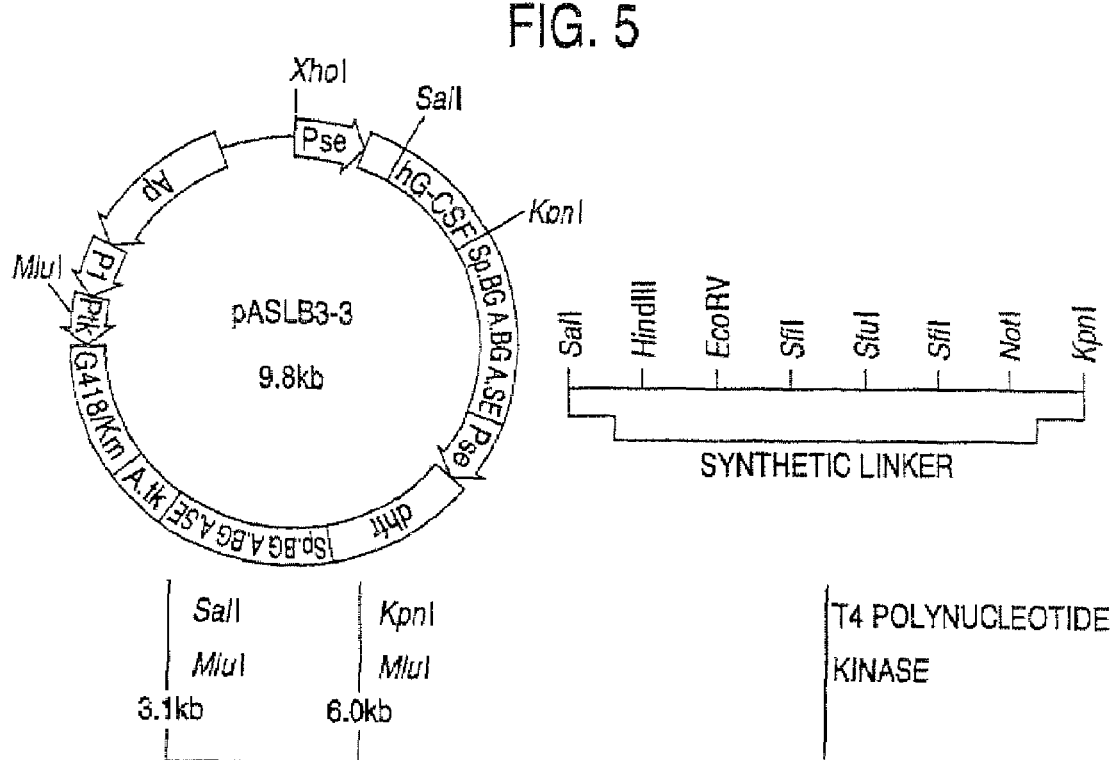
FIG. 5 shows a construction scheme for the plasmid pASLBC.
Figure 5:
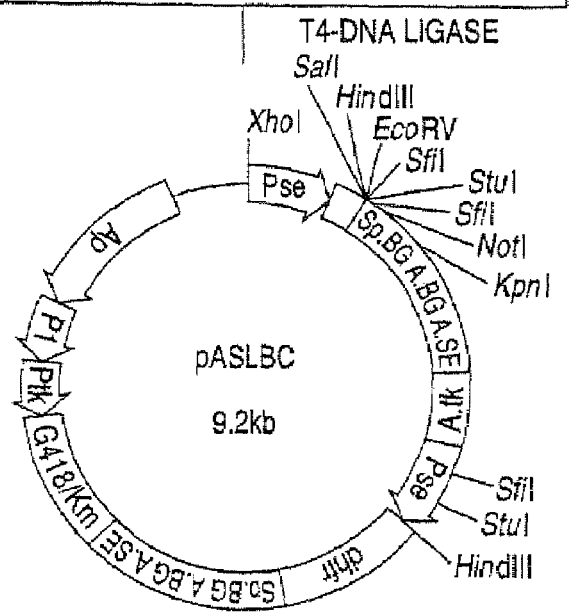

(5) Construction of pASLBC (cf. FIG. 5)

A plasmid, pASLBC, was constructed in the manner described below by eliminating from pASLB3-3 the hG-CSF gene and, instead, introducing thereinto a multicloning site. The multicloning site was prepared using synthetic DNAs.

pASLB3-3 (1 µg) obtained in (3) was dissolved in 30 µl of Y-175 buffer, 20 units of SalI and 20 units of MluI were added and the digestion reaction was carried out at 37° C. for 2 hours. The reaction mixture was subjected to agarose gel electrophoresis and a DNA fragment of about 3.1 kb was recovered.

Separately, 1 µg of the same plasmid was dissolved in 30 µl of Y-0 buffer, 20 units of KpnI was added and the digestion reaction was carried out at 37° C. for 2 hours. Then, NaCl was added to an NaCl concentration of 150 mM, 20 units of MluI was added and the digestion reaction was further carried out at 37° C. for 2 hours. The reaction mixture was subjected to agarose gel electrophoresis and a DNA fragment of about 6.0 kb was recovered.

Further, separately, the DNA linker specified below was synthesized as a linker for connecting the SalI cleavage site to the KpnI cleavage site. In this linker, there are the following restriction enzyme cleavage sites incorporated: HindIII, EcoRV SfiI, StuI and NotI.

```
         SalI  HindIII  EcoRV    SfiI StuI SfiI  NotI     KpnI
     5' TCGACAAGCTTGATATCGGCCTGTGAGGCCTCACTGGCCGCGGCCGCGGTAC 3'  (52 mer)

3'     GTTCGAACTATAGCCGGACACTCCGGAGTGACCGGCGCCGGCGC 5'          (44 mer)
```

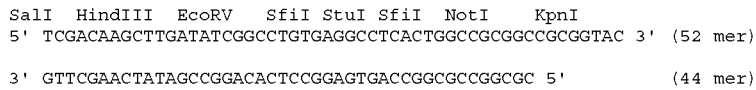

The 52 mer (SEQ ID NO: 3) and 44 mer (SEQ ID NO: 4) single-stranded DNAs of said DNA linker were respectively synthesized using an Applied Biosystems model 380A DNA synthesizer. The thus-synthesized DNAs (0.2 µg each) were dissolved in 20 µl of T4 kinase buffer, 30 units of T4 polynucleotide kinase (Takara Shuzo; hereinafter the same shall apply) was added and the phosphorylation reaction was carried out at 37° C. for 2 hours.

The SalI-MluI fragment (3.1 kb; 0.1 µg) and KpnI-MluI fragment (6.0 kb; 0.2 µg) each derived from pASLB3-3 as mentioned above were dissolved in 30 µl of T4 ligase buffer, 0.01 µg of the DNA linker mentioned above and 175 units of T4 DNA ligase were added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBC and its structure was identified by digestion with restriction enzymes.

Figure 6:
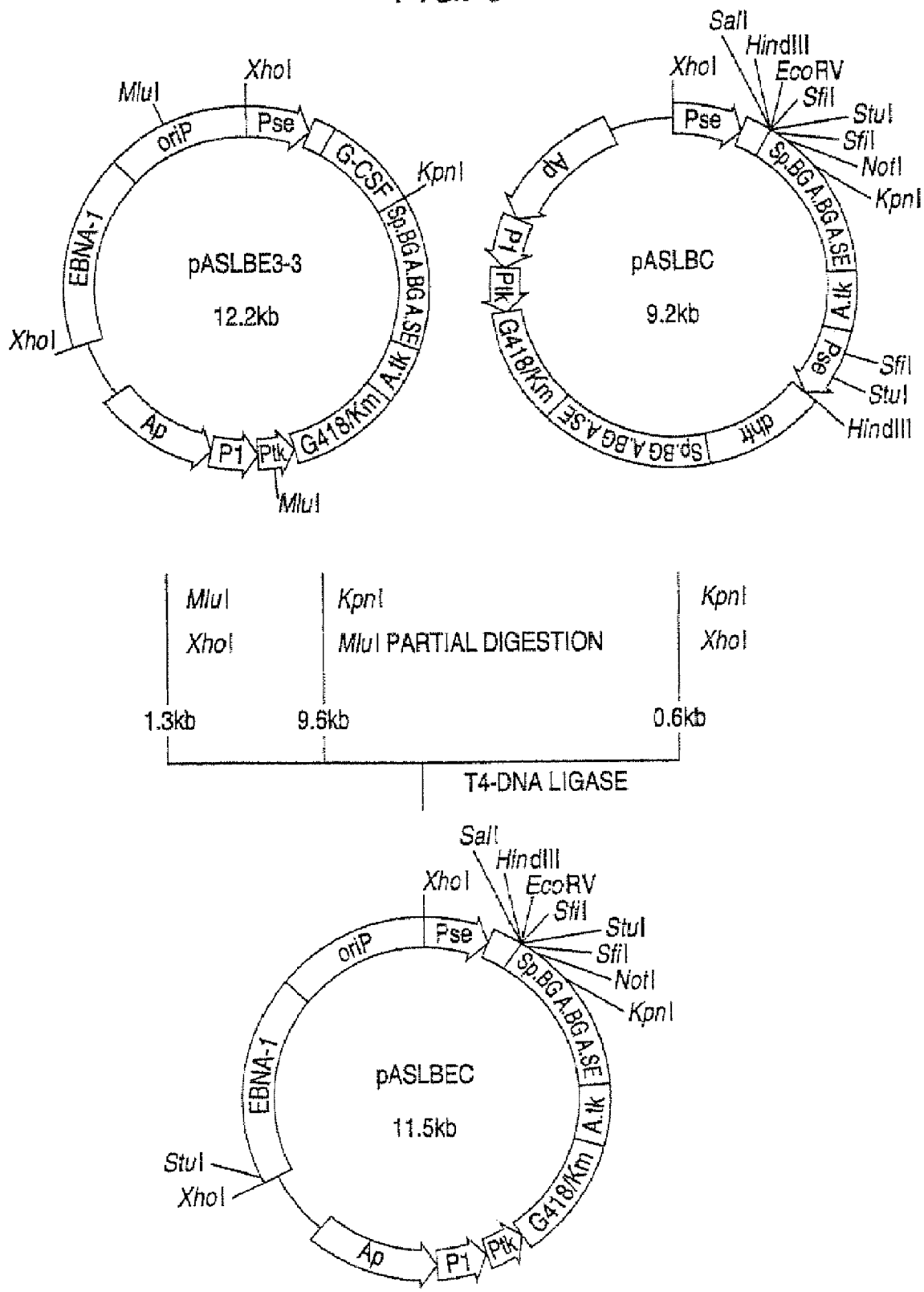
FIG. 6 shows a construction scheme for the plasmid pASLBEC.

(6) Construction of pASLBEC (cf. FIG. 6)

A plasmid, pASLBEC, was constructed by eliminating from pASLBC the dihydrofolate reductase (dhfr) expression unit and, instead, introducing thereinto the oriP and EBNA-1 gene.

pASLBE3-3 (1 µg) obtained in (4) was dissolved in 30 µl of Y-150 buffer, 20 units of MluI and 20 units of XhoI were added and the digestion reaction was carried out at 37° C. for 2 hours. The reaction mixture was subjected to agarose gel electrophoresis and a DNA fragment of about 1.3 kb was recovered.

Separately, 1 µg of the same plasmid was dissolved in 30 µl of Y-0 buffer, 20 units of KpnI was added and the digestion reaction was carried out at 37° C. for 2 hours. Then, NaCl was added to an NaCl concentration of 150 mM, 5 units of MluI was added and, further, partial digestion was effected at 37° C. for 20 minutes. The reaction mixture was subjected to agarose gel electrophoresis and a DNA fragment of about 9.6 kb was isolated.

Further, separately, pASLBC (1 µg) was dissolved in 30 µl of Y-0 buffer, 20 units of KpnI was added and the digestion reaction was carried out at 37° C. for 2 hours. Then, NaCl was added to an NaCl concentration of 100 mM, 20 units of XhoI was added and, further, the digestion reaction was carried out at 37° C. for 2 hours. The reaction mixture was subjected to agarose gel electrophoresis and a DNA fragment of about 0.6 kb was isolated.

The MluI-XhoI fragment (1.3 kb; 0.2 μg) and KpnI-MluI fragment (9.6 kb; 0.2 μg) each derived from pASLBE3-3 as described above and the pASLBC-derived KpnI-XhoI fragment (0.6 kb; 0.05 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBEC and its structure was identified by digestion with restriction enzymes.

Figure 7:
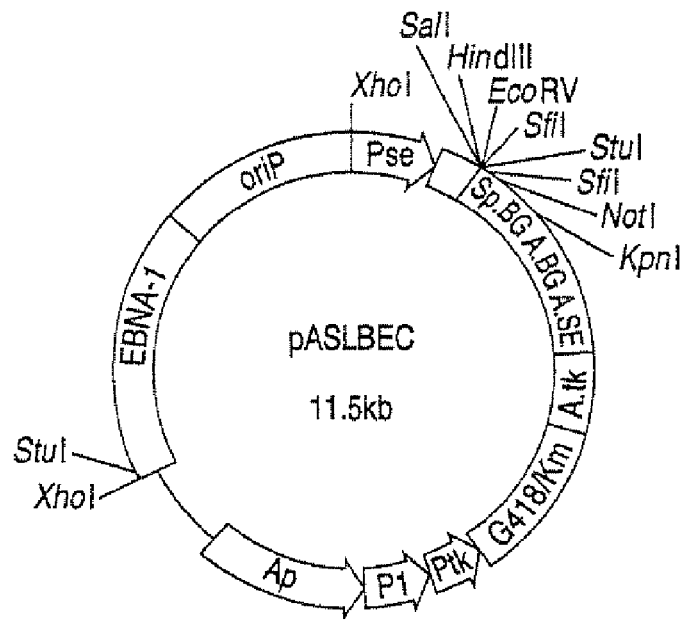
FIG. 7 shows a construction scheme for the plasmid pASLBEC2.
Figure 7:
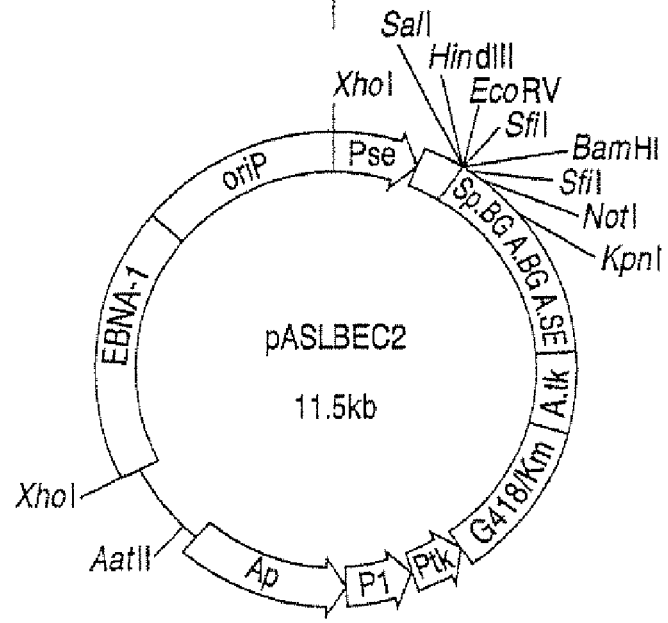

(7) Construction of pASLBEC2 (cf. FIG. 7)

A plasmid, pASLBEC2, was constructed in the manner mentioned below by introducing a BamHI linker into the StuI site in the multicloning site of pASLBEC. In pASBEC2, the StuI site in the multicloning site is missing.

pASLBEC (1 μg) obtained in (6) was dissolved in 30 μl of Y-100 buffer, 5 units of StuI was added and partial digestion was effected at 37° C. for 20 minutes. The reaction mixture was subjected to agarose gel electrophoresis and a DNA fragment of about 11.5 kb was recovered. The DNA recovered was dissolved in 30 μl of T4 ligase buffer, 0.01 μg of a BamHI linker (5'-pCCGGATCCGG-3'; Takara Shuzo) and 175 units of T4 DNA ligase were added and the ligation reaction was carried out at 12° C. for 16 hours. After precipitation with ethanol, the precipitate was dissolved in 30 μl of Y-100 buffer, 20 units of BamHI was added and the digestion reaction was carried out at 37° C. for 2 hours. The reaction mixture was subjected to agarose gel electrophoresis and a DNA fragment of about 11.5 kb was recovered. The DNA fragment recovered was dissolved in 20 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBEC2 and its structure was identified by digestion with restriction enzymes.

Figure 8:
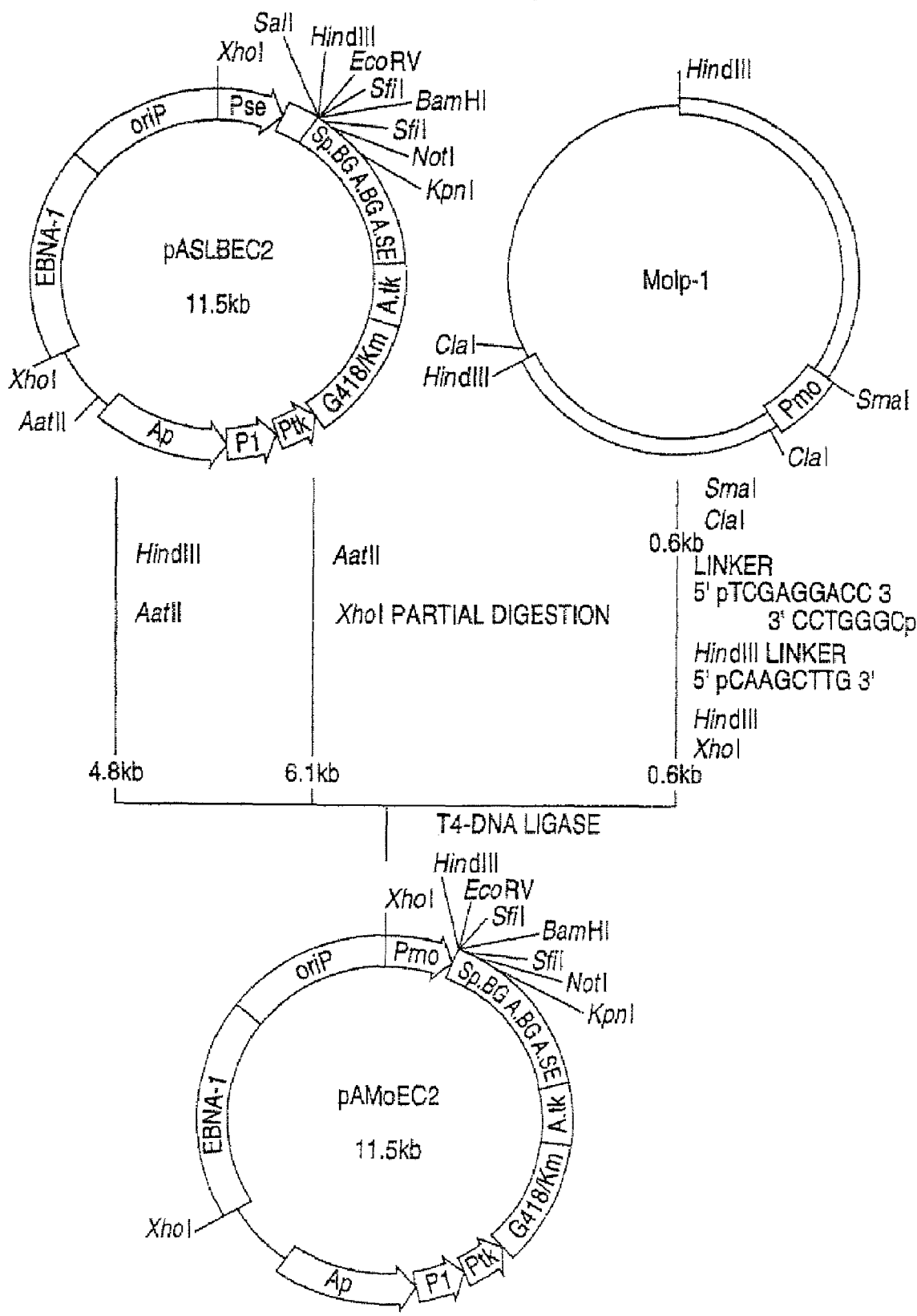
FIG. 8 shows a construction scheme for the plasmid pAMoEC2.

(8) Construction of pAMoEC2 (cf. FIG. 8)

A plasmid, pAMoEC2, was constructed in the manner described below by replacing the promoter in pASLBEC2 [promoter resulting from fusion of the SV40 early gene promoter and parts of the R and U5 regions of the long terminal repeat (LTR) of HTLV-1] with the promoter of LTR of the Moloney murine leukemia virus. The promoter of Moloney murine leukemia virus LTR was excised for use from the plasmid Molp-1 [Akinori Ishimoto et al.: Virology, 141, 30 (1985)].

pASLBEC2 (1 μg) obtained in (7) was dissolved in 30 μl of a buffer comprising 10 mM Tris-HCl (pH 7.5), 6 mM MgCl₂, 50 mM KCl and 6 mM 2-mercaptoethanol (said buffer hereinafter referred to as "K-50 buffer" for short), 20 units of HindIII and 20 units of AatII (Toyobo) were added and the digestion reaction was carried out at 37° C. for 2 hours. The reaction mixture was subjected to agarose gel electrophoresis and a DNA fragment of about 4.8 kb was recovered.

Separately, 1 μg of the same plasmid was dissolved in 30 μl of K-50 buffer, 20 units of AatII was added and the digestion reaction was carried out at 37° C. for 2 hours. Then, 5 units of XhoI was added and, further, partial digestion was effected at 37° C. for 20 minutes. The reaction mixture was subjected to agarose gel electrophoresis and a DNA fragment of about 6.1 kb was recovered.

Then, the linker shown below was synthesized as a linker for connecting the XhoI cleavage site to the ClaI cleavage site.

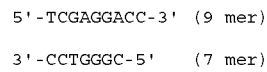

```
5'-TCGAGGACC-3'  (9 mer)

3'-CCTGGGC-5'    (7 mer)
```

The 9 mer and 7 mer single-stranded DNAs for preparing the above DNA linker were synthesized using an Applied Biosystems model 380A DNA synthesizer. The DNA synthesized (0.2 μg each) were dissolved in 40 μl of T4 kinase buffer, 30 units of T4 polynucleotide kinase was added and the phosphorylation reaction was carried out at 37° C. for 2 hours.

Further, separately, 1 μg of Molp-1 [Akinori Ishimoto et al.: Virology, 141, 30 (1985)] was dissolved in 30 μl of Y-50 buffer, 20 units of ClaI was added and the digestion reaction was carried out at 37° C. for 2 hours. After precipitation with ethanol, the precipitate was dissolved in 30 μl of T4 ligase buffer, 0.01 μg of the DNA linker described above and 175 units of T4 DNA ligase were added and the ligation reaction was carried out at 12° C. for 16 hours. After precipitation with ethanol, the precipitate was dissolved in 30 μl of K-20 buffer, 20 units of SmaI was added and the digestion reaction was carried out at 37° C. for 2 hours. The reaction mixture was subjected to agarose gel electrophoresis and a DNA fragment of about 0.6 kb was recovered. The DNA fragment recovered was dissolved in 30 μl of T4 ligase buffer, 0.03 μg of a HindIII linker (5'-pCAAGCTTG-3'; Takara Shuzo) and 175 units of T4 DNA ligase were added and the ligation reaction was carried out at 120° C. for 16 hours. After precipitation with ethanol, the precipitate was dissolved in 30 μl of a buffer comprising 10 mM Tris-HCl (pH 7.5), 6 mM MgCl₂, 50 mM NaCl and 6 mM 2-mercapto-ethanol (said buffer hereinafter referred to as "Y-50 buffer" for short), 10 units of HindIII was added and the digestion reaction was carried out at 37° C. for 2 hours. Then, NaCl was added to an NaCl concentration of 100 mM, 10 units of XhoI was added and the digestion reaction was further carried out at 37° C. for 2 hours. The reaction mixture was subjected to agarose gel electrophoresis and a DNA fragment of about 0.6 kb was recovered.

The HindIII-AatII fragment (4.8 kb; 0.2 μg) and AatII-XhoI fragment (6.1 kb; 0.2 μg) each derived from pASLBEC2 as described above and the Molp-1-derived HindIII-XhoI fragment (0.6 kb; 0.05 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoEC2 and its structure was identified by digestion with restriction enzymes.

Figure 9:
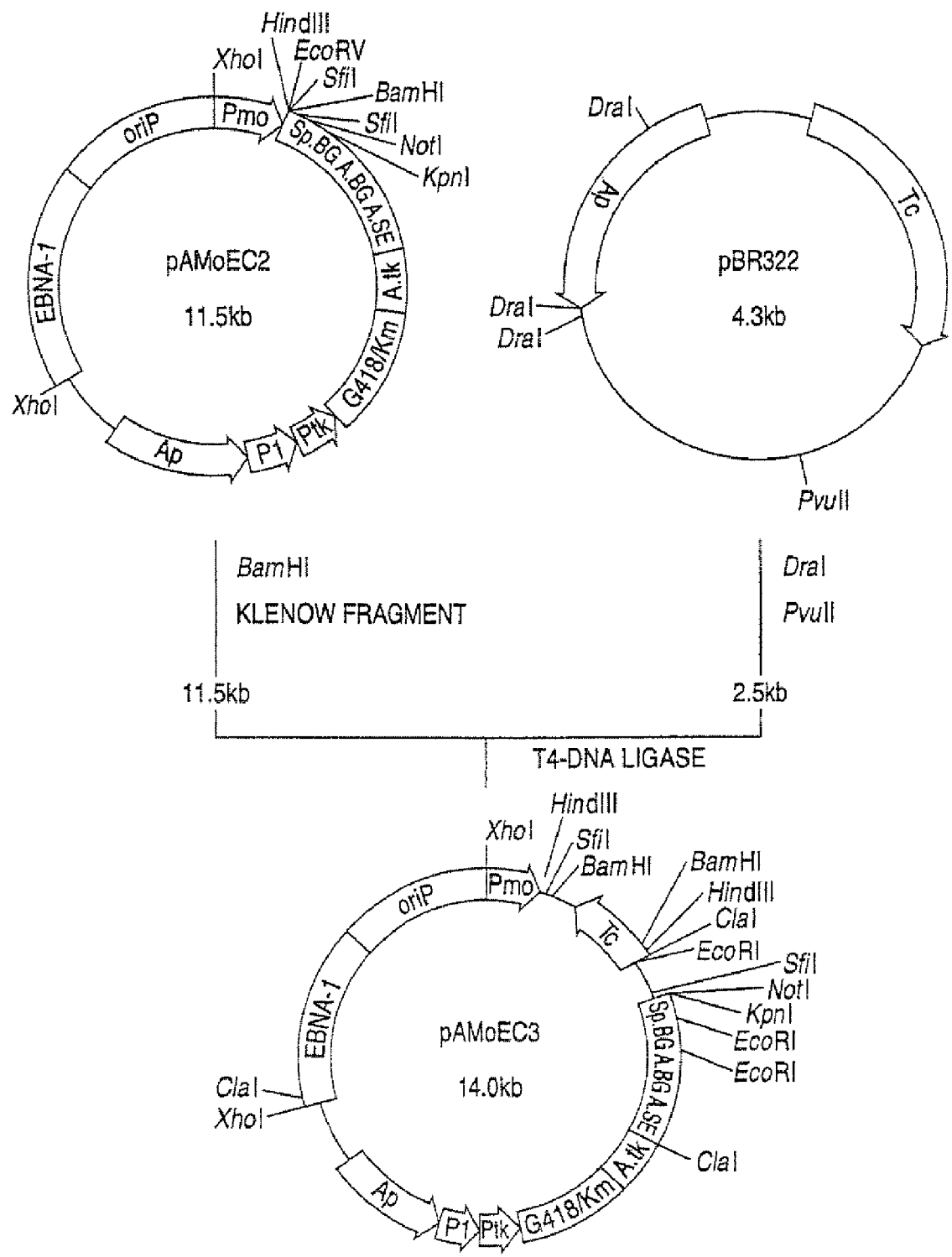
FIG. 9 shows a construction scheme for the plasmid pAMoEC3.

(9) Construction of pAMoEC3 (cf. FIG. 9)

A plasmid, pAMoEC3, was constructed in the manner described below by inserting, as a stuffer DNA, a DNA fragment [DraI-PvuII fragment (2.5 kb)] containing the tetracyline resistance gene of pER322 into the BamHI site in the multicloning site of pAMoEC2.

pAMoEC2 (1 μg) obtained in (8) was dissolved in 30 μl of Y-100 buffer, 20 units of BamHI was added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 5' cohesive end resulting from BamHI digestion to a blunt end. The reaction mixture was subjected to agarose gel electrophoresis and a DNA fragment of about 11.5 kb was recovered.

Separately, 1 µg of pBR322 [Bolivar et al.: Gene, 2, 95 (1977)] was dissolved in 30 µl of Y-50 buffer, 20 units of DraI and 20 units of PvuII were added and the digestion reaction was carried out at 37° C. for 2 hours. The reaction mixture was subjected to agarose gel electrophoresis and a DNA fragment of about 2.5 kb was recovered.

The pAMoEC2-derived BamHI (blunt end) fragment (11.5 kb; 0.1 µg) and pBR322-derived DraI-PvuII fragment (2.5 kb; 0.2 µg) respectively obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin- and tetracycline-resistant strain was obtained. From this transformant, a plasmid was isolated by a known method. This plasmid was named pAMoEC3 and its structure was identified by digestion with restriction enzymes.

Figure 10:
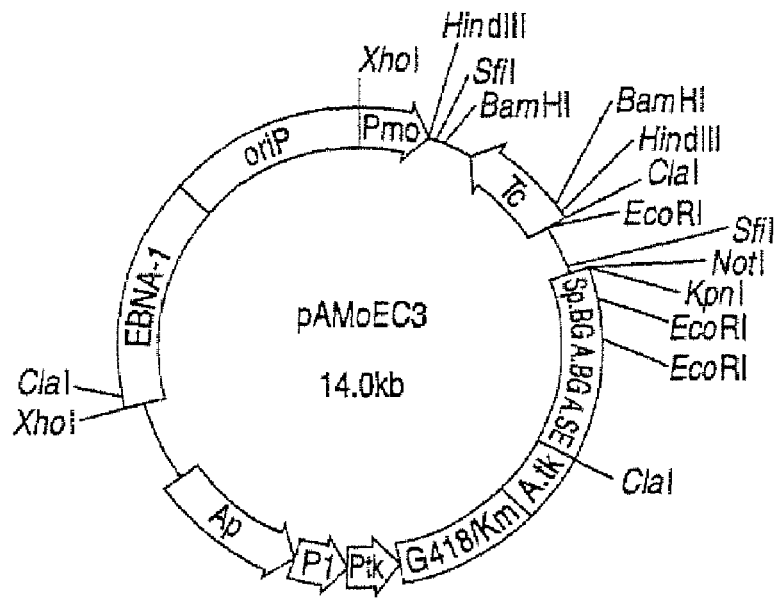
FIG. 10 shows a construction scheme for the plasmid pAMoERC3.
Figure 10:
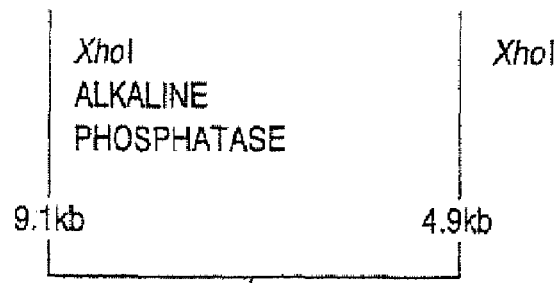
Figure 10:
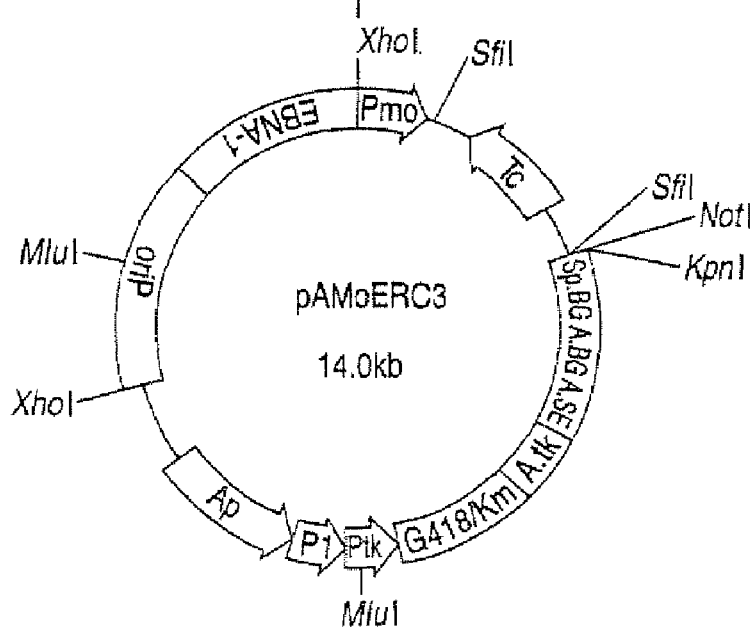

(10) Construction of pAMoERC3 (cf. FIG. 10)

A plasmid, pAMoERC3, was constructed in the manner described below by reversing the direction of the oriP and EBNA-1 gene unit in pAMoEC3.

pAMoEC3 (1 µg) obtained in (9) was dissolved in 30 µl of Y-100 buffer, 20 units of XhoI was added and the digestion reaction was carried out at 37° C. for 2 hours. Then, 30 µl of 1 M Tris-HCl (pH 8.0) and 1 unit of *Escherichia coli*-derived alkaline phosphatase (Takara Shuzo) were added and the dephosphorylation reaction was carried out at 37° C. for 2 hours. After precipitation with ethanol, the precipitate was dissolved in 30 µl of a buffer comprising 10 mM Tris-HCl (pH 8.0) and 1 mM EDTA (sodium ethylenediaminetetraacetate) (hereinafter, "TE buffer") and subjected to agarose gel electrophoresis and a DNA fragment of about 9.1 kb was recovered.

Separately, 1 µg of the same plasmid was dissolved in 30 µl of Y-100 buffer, 20 units of XhoI was added and the digestion reaction was carried out at 37° C. for 2 hours. The reaction mixture was subjected to agarose gel electrophoresis and a DNA fragment of about 4.9 kb was recovered.

The pAMoEC3-derived XhoI fragment (9.1 kb; 0.1 µg) and the XhoI fragment (4.9 kb; 0.2 µg) derived from the same plasmid, respectively obtained in the above manner, were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoERC3 and its structure was identified by digestion with restriction enzymes.

Figure 11:
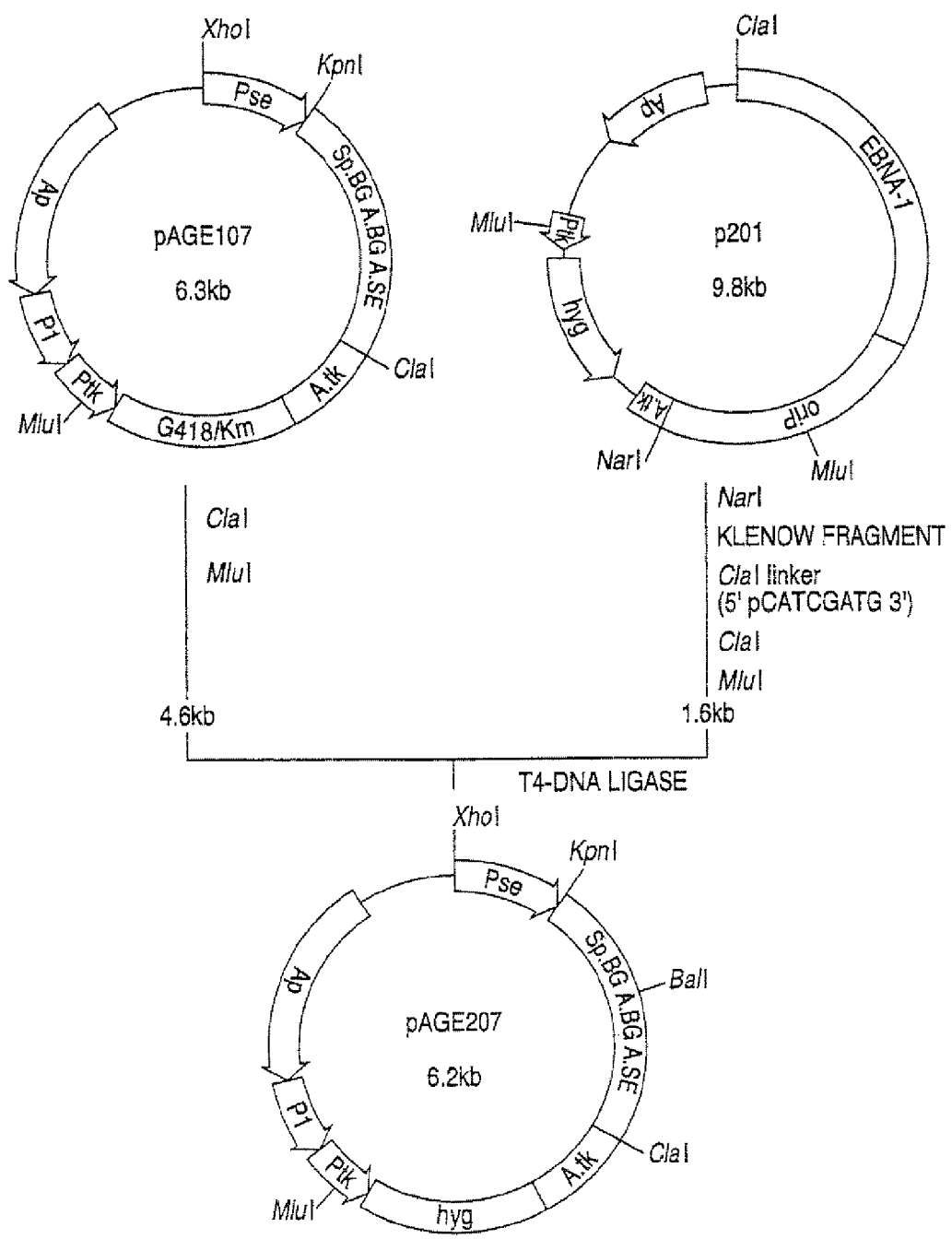
FIG. 11 shows a construction scheme for the plasmid pAGE207.

(11) Construction of pAGE207 (cf. FIG. 11)

A plasmid, pAGE207, was constructed in the manner described below by replacing the G418 resistance gene in pAGE107 with the hygromycin (hyg) resistance gene. The hyg resistance gene was excised for use from p201 [Bill Sugden et al.: Nature, 313, 812 (1985)].

pAGE107 (JP-A3-22979; 1 µg) was dissolved in 30 µl of Y-50 buffer, 20 units of ClaI was added and the digestion reaction was carried out at 37° C. for 2 hours. Then, NaCl was added to an NaCl concentration of 150 mM, 20 units of MluI was added and the digestion reaction was further carried out at 37° C. for 2 hours. The reaction mixture was subjected to agarose gel electrophoresis and a DNA fragment of about 4.6 kb was recovered.

p201 [Bill Sugden et al.: Nature, 313, 812 (1985); 0.5 µg] was dissolved in 30 µl of Y-50 buffer, 20 units of NarI (New England Biolabs) was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end formed upon NarI digestion to a blunt end. The reaction was terminated by extraction with phenol. After extraction with chloroform and precipitation with ethanol, the precipitate was dissolved in 20 µl of T4 ligase buffer, 0.05 µg of a ClaI linker (5' pCATCGATG 3'; Takara Shuzo) and 175 units of T4 DNA ligase were added and the ligation reaction was carried out at 12° C. for 16 hours. After precipitation with ethanol, the precipitate was dissolved in 30 µl of Y-50 buffer, 10 units of ClaI was added and the digestion reaction was carried out at 37° C. for 2 hours. Then, NaCl was added to an NaCl concentration of 150 mM, 10 units of MluI was added and, further, the digestion reaction was carried out at 37° C. for 2 hours. The reaction mixture was subjected to agarose gel electrophoresis and a DNA fragment of about 1.6 kb was recovered.

The pAGE107-derived ClaI-MluI fragment (4.6 kb; 0.2 µg) and p201-derived ClaI-MluI fragment (1.6 kb; 0.1 µg) respectively obtained in the above manner were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAGE207 and its structure was identified by digestion with restriction enzymes.

Figure 12:
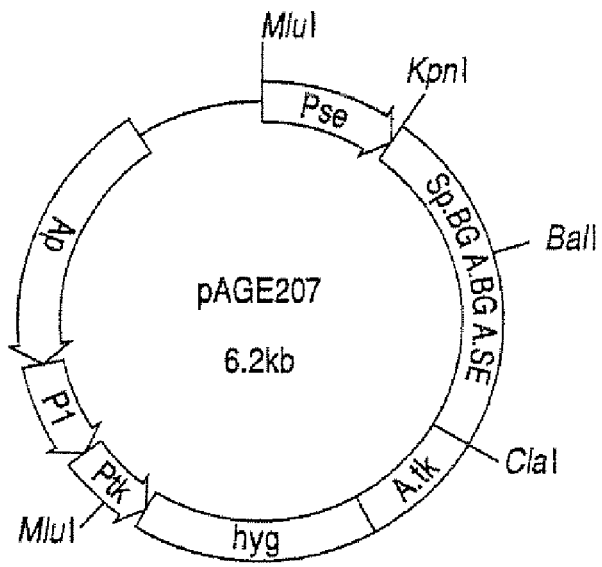
FIG. 12 shows a construction scheme for the plasmid pAGE207ScN.
Figure 12:
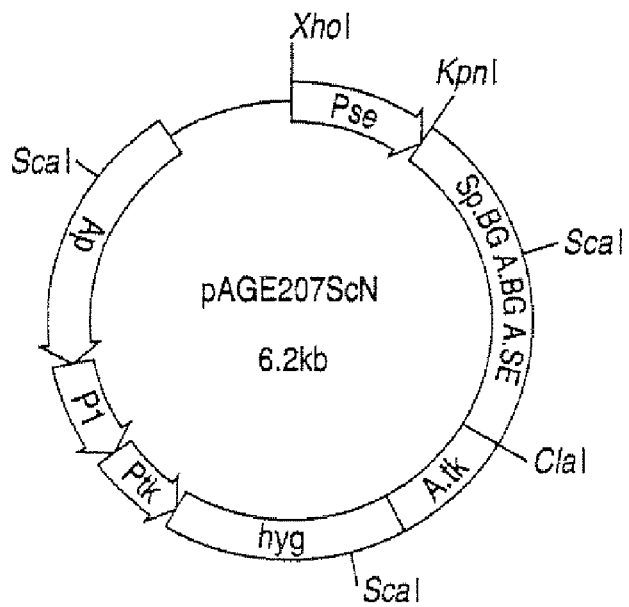

(12) Construction of pAGE207ScN (cf. FIG. 12)

For eliminating the SfiI-site-related sequence occurring in the rabbit β globin gene, a plasmid, pAGE207ScN, was constructed in the manner described below by inserting a ScaI linker into pAGE207 at the BalI site. In pAGE207ScN, the number of ScaI linkers inserted is unknown.

pAGE207 (0.5 µg) obtained in (11) was dissolved in 30 µl of Y-0 buffer, 10 units of BalI was added and the digestion reaction was carried out at 37° C. for 2 hours. After precipitation with ethanol, the precipitate was dissolved in 20 µl of T4 ligase buffer, 0.01 µg of a ScaI linker (5' pAAGTACTT 3'; Takara Shuzo) and 175 units of T4 DNA ligase were added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAGE207ScN and its structure was identified by digestion with restriction enzymes.

Figure 13:
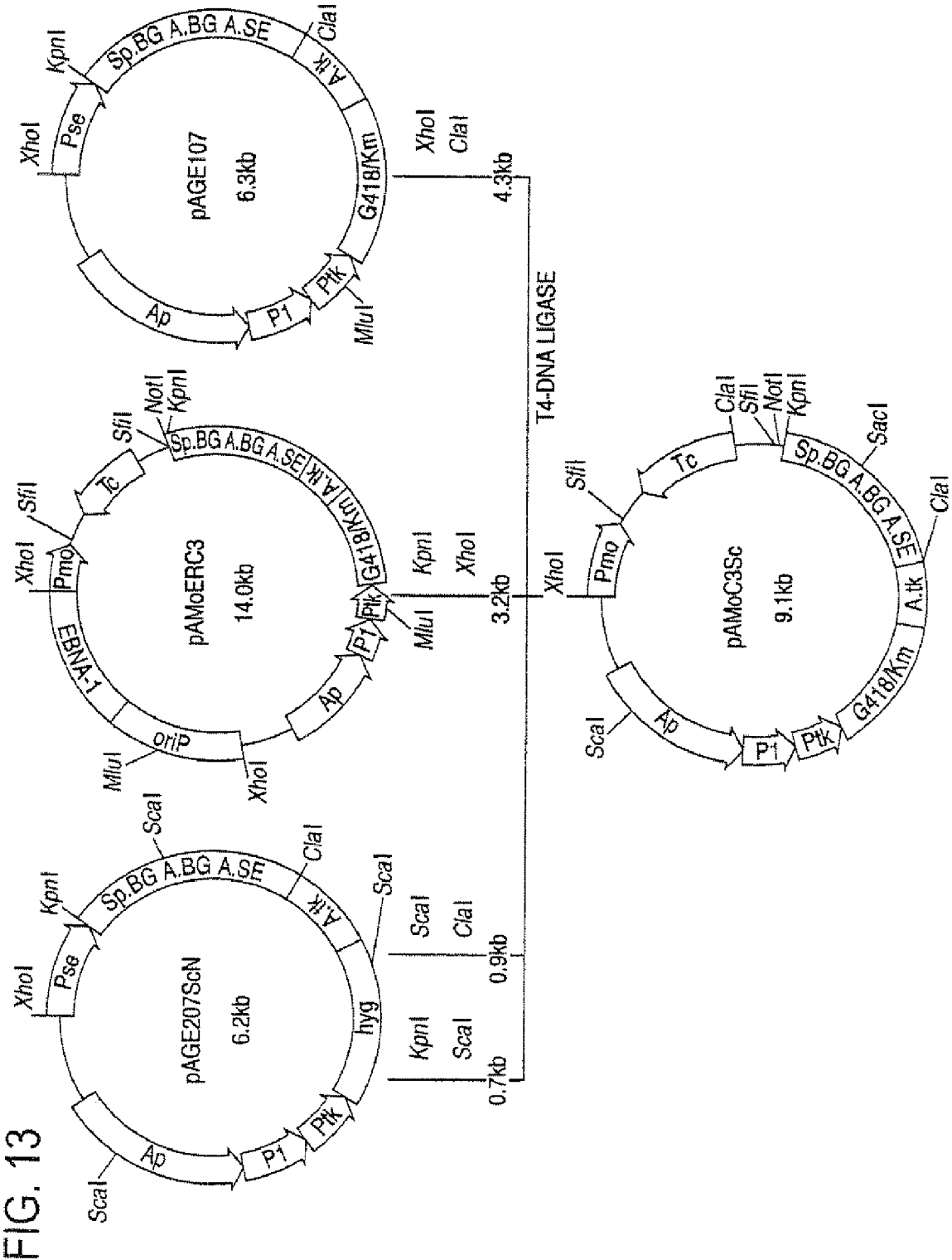
FIG. 13 shows a construction scheme for the plasmid pAMoC3Sc.

(13) Construction of pAMoC3Sc (cf. FIG. 13)

For eliminating the SfiI-site-related occurring in the rabbit β globin gene in pAMoERC3, a plasmid, pAMoERC3Sc, was constructed in the manner described below by replacing the rabbit β globin gene in pAMoERC3 with the rabbit β globin gene in pAGE207ScN no longer having that sequence in question. For convenience sake, pAMoC3Sc was first constructed and then pAMoERC3Sc was constructed. While, in the above-mentioned pAGE207ScN, the number of ScaI linkers inserted is unknown, in the case of pAMOERC3Sc, the number of ScaI sites inserted is presumably 1, since pAGE207ScN was once cleaved with ScaI.

pAGE207ScN (1 μg) obtained in (12) was dissolved in 30 μl of Y-0 buffer, 20 units of KpnI was added and the digestion reaction was carried out at 37° C. for 2 hours. Then, NaCl was added to an NaCl concentration of 100 mM, 20 units of ScaI was added and the digestion reaction was further carried out at 37° C. for 2 hours. The reaction mixture was subjected to agarose gel electrophoresis and a DNA fragment of about 0.7 kb was recovered.

Separately, 1 μg of the same plasmid was dissolved in 30 μl of Y-100 buffer, 20 units of ScaI and 20 units of ClaI were added and the digestion reaction was carried out at 37° C. for 2 hours. The reaction mixture was subjected to agarose gel electrophoresis and a DNA fragment of about 0.9 kb was recovered.

Further, separately, 1 μg of pAMoERC3 obtained in (10) was dissolved in 30 μl of Y-0 buffer, 20 units of KpnI was added and the digestion reaction was carried out at 37° C. for 2 hours. Then, NaCl was added to an NaCl concentration of 100 mM, 20 units of XhoI was added and the digestion reaction was further carried out at 37° C. for 2 hours. The reaction mixture was subjected to agarose gel electrophoresis and a DNA fragment of about 3.2 kb was recovered.

Then, 1 μg of pAGE107 (JP-A-2-227075) was dissolved in 30 μl of Y-100 buffer, 20 units of XhoI and 20 units of ClaI were added and the digestion reaction as carried out at 37° C. for 2 hours. The reaction mixture was subjected to agarose gel electrophoresis and a DNA fragment of about 4.3 kb was recovered.

The pAGE207ScN-derived KpnI-ScaI fragment (0.7 kb; 0.1 μg), pAGE207ScN-derived ScaI-ClaI fragment (0.9 kb; 0.1 μg), pAMoERC3-derived KpnI-XhoI fragment (3.2 kb; 0.3 μg) and pAGE107-derived XhoI-ClaI fragment (4.3 kb; 0.3 μg) respectively obtained as described above were dissolved in 30 μl of T4 ligase buffer, 175 units of T4 DNA ligase was added and the ligation reaction was carried out at 12° C. for 16 hours. The reaction mixture was used to transform Escherichia coli HB101 and an ampicillin-resistant strain was obtained. From this transformant, a plasmid was isolated by a known method. This plasmid was named pAMoC3Sc and its structure was identified by digestion with restriction enzymes.

Figure 14:
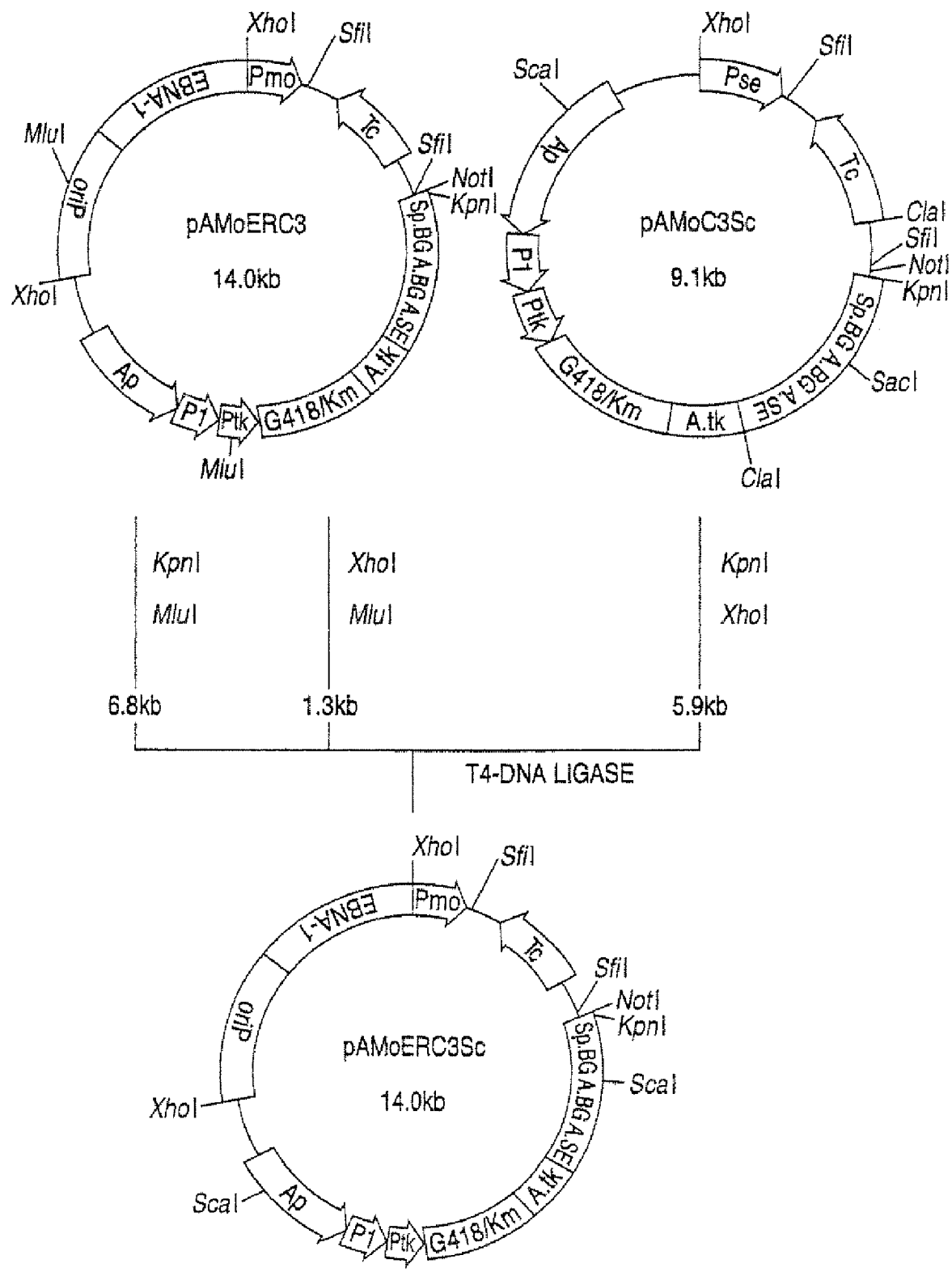
FIG. 14 shows a construction scheme for the plasmid pAMoERC3Sc.

(14) Construction of pAMoERC3Sc (cf. FIG. 14)

pAMoERC3 (1 μg) obtained in (10) was dissolved in 30 μl of Y-0 buffer, 20 units of KpnI was added and the digestion reaction was carried out at 37° C. for 2 hours. Then, NaCl was added to an NaCl concentration of 150 mM, 20 units of MluI was added and the digestion reaction was further carried out at 37° C. for 2 hours. The reaction mixture was subjected to agarose gel electrophoresis and a DNA fragment of about 6.8 kb was recovered.

Separately, 1 μg of the same plasmid was dissolved in 30 μl of Y-150 buffer, 20 units of XhoI and 20 units of MluI were added and the digestion reaction was carried out at 37° C. for 2 hours. The reaction mixture was subjected to agarose gel electrophoresis and a DNA fragment of about 1.3 kb was recovered.

Further, separately, 1 μg of pAMoC3Sc was dissolved in 30 μl of Y-0 buffer, 20 units of KpnI was added and the digestion reaction was carried out at 37° C. for 2 hours. Then, NaCl was added to an NaCl concentration of 100 mM, 20 units of XhoI was added and the digestion reaction was further carried out at 37° C. for 2 hours. The reaction mixture was subjected to agarose gel electrophoresis and a DNA fragment of about 5.9 kb was recovered.

The pAMoERC3-derived KpnI-MluI fragment (6.8 kb; 0.2 μg), pAMoERC3-derived XhoI-MluI fragment (1.3 kb; 0.05 μg) and pAMoC3Sc-derived KpnI-XhoI fragment (5.9 kb; 0.2 μg) respectively obtained as described above were dissolved in 30 μl of T4 ligase buffer, 175 units of T4 DNA ligase was added and the ligation reaction was carried out at 12° C. for 16 hours. The reaction mixture was used to transform Escherichia coli HB101 by the method of Cohen et al. and an ampicilline-resistant strain was obtained. From this transformant, a plasmid was isolated by a known method. This plasmid was named pAMoERC3Sc and its structure was identified by digestion with restriction enzymes.

pAMoERC3Sc has the long terminal repeat of Moloney murine leukemia virus as a promoter for heterologous gene expression. Its design is such that, for efficient heterologous gene expression, the heterologous gene inserted is to be followed by the rabbit β globin gene splicing signal, rabbit β globin gene poly A addition signal and SV40 early gene poly A addition signal. Further, it has the G418 resistance gene as a drug resistance marker for animal cells and the kanamycin resistance gene (same as the G418 resistance gene) and ampicillin resistance gene as drug resistance markers for Escherichia coli. Further, it has the replication origin (oriP) of the Epstein-Barr virus and the EBNA-1 gene acting trans on the oriP to induce replication, so that it can retain its plasmid state in Namalwa cells and many other cells except for rodent cells, without being incorporated into the chromosome.

cDNA library construction using pAMoERC3Sc can be realized by adding a SfiI linker to both ends of cDNA and then incorporating the addition product into pAMoERC3Sc at the SfiI site.

Figure 15:
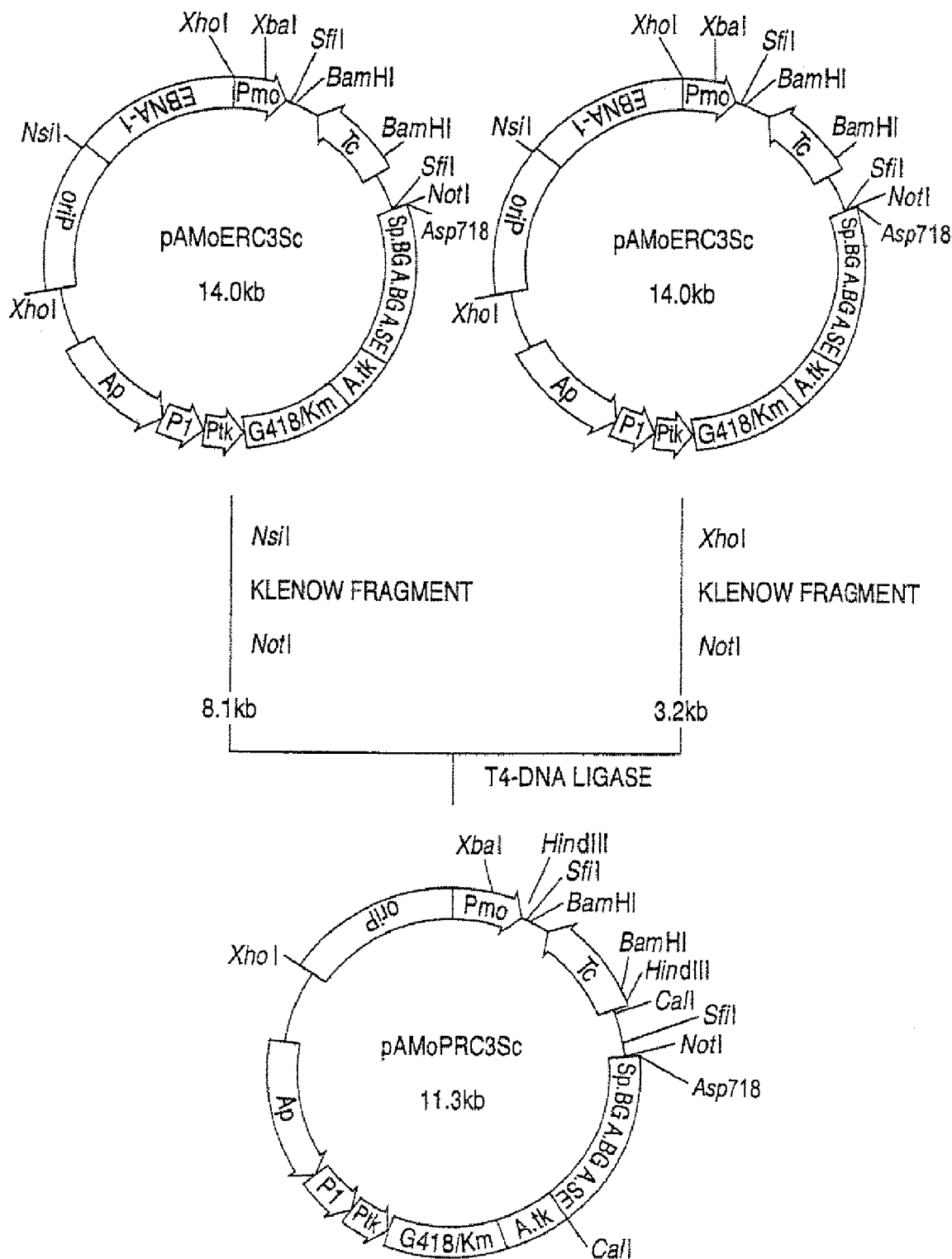
FIG. 15 shows a construction scheme for the plasmid pAMoPRC3Sc.

(15) Construction of pAMoPRC3Sc (cf. FIG. 15)

When cells expressing EBNA-1 by nature, for example Namalwa cells, are used as the host, it is supposed that the plasmid pAMoERC3Sc introduced into such host, even if it were lacking the EBNA-1 gene, could occur in the state of plasmid without being incorporated into the chromosome. Therefore, a plasmid, pAMoPRC3Sc, was constructed in the manner described below by eliminating the EBNA-1 gene from pAMoERC3Sc. Like pAMoERC3Sc, pAMoPRC3Sc can be used as a direct expression cloning vector.

pAMoERC3Sc (2 μg) obtained in (14) was dissolved in 30 μl of Y-50 buffer, 20 units of NsiI (New England Biolabs) was added and the digestion reaction was carried out at 37° C. for 2 hours. After precipitation with ethanol, the precipitate was dissolved in 30 μl of DNA polymerase I buffer, 6 units of Escherichia coli-derived DNA polymerase I Klenow fragment was added and the reaction was carried out at 37° C. for 60 minutes to convert the 3' cohesive end formed upon NsiI digestion to a blunt end. The reaction was terminated by extraction with phenol. After extraction with chloroform and precipitation with ethanol, the precipitate was dissolved in 30 μl of Y-100 buffer, 20 units of NotI was added and the digestion reaction was carried out at 37° C. for 2 hours. The reaction mixture was subjected to agarose gel electrophoresis and a DNA fragment of about 8.1 kb was recovered.

Separately, 2 μg of the same plasmid was dissolved in 30 μl of Y-100 buffer, 20 units of XhoI was added and the digestion reaction was carried out at 37° C. for 2 hours. After precipitation with ethanol, the precipitate was dissolved in 30 μl of DNA polymerase I buffer, 6 units of Escherichia coli-derived DNA polymerase I Klenow fragment was added and the reaction was carried out at 37° C. for 60 minutes to convert the 5' cohesive end formed upon XhoI digestion to a blunt end. The reaction was terminated by extraction with phenol. After extraction with chloroform and precipitation with ethanol, the precipitate was dissolved in 30 μl of Y-100 buffer, 20 units of NotI was added and the digestion reaction was carried out at 37° C. for 2 hours. The reaction mixture was subjected to agarose gel electrophoresis and a DNA fragment of about 3.2 kb was recovered.

The pAMoERC3Sc-derived NsiI (blunt end)-NotI fragment (8.1 kb; 0.1 μg) and XhoI (blunt end)-NotI fragment (3.2 kb; 0.1 μg) respectively obtained in the above manner were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoPRC3Sc and its structure was identified by digestion with restriction enzymes.

2. Cloning of α-1,3-fucosyltransferase cDNA from Cells of Human Monocytic Cell Line THP-1

(1) Extraction of mRNA from Cells of Human Monocytic Cell Line THP-1

Using the mRNA extraction kit Fast Track (Invitrogen; article number K1593-02), about 30 μg of mRNA was obtained from $1 \times 10^8$ THP-1 cells (ATCC TIB 202) The reagents and procedure used were as described in the manual attached to the kit.

(2) cDNA Library Construction

Using GIBCO BRL's kit cDNA Synthesis System, double-stranded cDNA was synthesized, with oligo dT as a primer, from 8 μg of the mRNA obtained in the above manner. On that occasion, GIBCO BRL's Super Script™ RNase H-Reverse Transcriptase was used as the reverse transcriptase in lieu of Moloney murine leukemia virus (M-MLV) reverse transcriptase belonging to the kit. Then, the cDNA was provided, on both ends, with the SfiI linker shown below and subjected to agarose gel electrophoresis for fractionating the cDNA by size. cDNA fragments not less than about 1.6 kb were thus recovered.

```
5'-CTTTAGAGCAC-3'    (11 mer)

3'-GAAATCTC-5'       (8 mer)
```

The 11 mer (SEQ ID NO: 5) and 8 mer single-stranded DNAs of the SfiI linker were respectively synthesized using an Applied Biosystems model 380A DNA synthesizer. Each DNA synthesized (50 μg) was individually dissolved in 50 μl of T4 kinase buffer, 30 units of T4 polynucleotide kinase (Takara Shuzo) was added and the phosphorylation reaction was carried out at 37° C. for 16 hours. The double-stranded cDNA synthesized as described above and the phosphorylated linkers (4 μg of the 11 mer and 2.9 μg of the 8 mer) phosphorylated as described above were dissolved in 45 μl of T4 ligase buffer, 1,050 units of T4 DNA ligase was added and the ligation reaction was carried out at 16° C. for 16 hours. The reaction mixture was subjected to agarose gel electrophoresis and cNDA fragments not less than about 1.6 kb in size were recovered.

Separately, 24 μg of the direct expression cloning vector pAMoPRC3Sc obtained in 1-(15) was dissolved in 590 μl of Y-50 buffer, 80 units of SfiI was added and the digestion reaction was carried out at 37° C. for 16 hours. Then, a portion (5 μl) of the reaction mixture was subjected to agarose gel electrophoresis. After confirmation, in this manner, of completion of the cleavage, 40 units of BamHI was added and the digestion reaction was carried out at 37° C. for 2 hours to quantitatively reduce the background (clones without any cDNA insert) resulting from the cDNA library construction. The reaction mixture was then subjected to agarose gel electrophoresis and a DNA fragment of about 8.8 kb was recovered.

The pAMoPRC3Sc-derived SfiI fragment (8.8 kb; 2 μg) obtained as described above and the cDNA purified in the above manner were dissolved in 250 μl of T4 ligase buffer, 2,000 units of T4 DNA ligase was added and the ligation reaction was carried out at 16° C. for 16 hours. Then, after addition of 5 μg of transfer RNA (tRNA), precipitation was effected by addition of ethanol and the precipitate was dissolved in 20 μl of TE buffer. The reaction mixture was used to transform *Escherichia coli* LE392 [Maniatis et al. (editors): Molecular Cloning, second edition, Cold Spring Harbor Laboratory, 1939] by electoporation [William J. Dower et al.: Nucleic Acids Research, 16, 6127 (1988)] and about 560,000 ampicillin-resistant strains.

(3) Cloning of α-1,3-fucosyltransferase cDNA (TH21)

The ampicillin-resistant strains (about 560,000 strains; cDNA library) obtained in the above manner were mixed and plasmids were prepared using Qiagen's plasmid preparation kit>plasmid<maxi kit (article number 41031). The plasmids prepared were precipitated by addition of ethanol and then dissolved in TE buffer to a concentration of 1 μg/μl.

The above plasmid was introduced into Namalwa cells conditioned in serum-free medium (KJM-1 strain) [Hosoi et al. Cytotechnology, 1, 151 (1988)] by electroporation [Miyaji et al.: Cytotechnology, 3, 133 (1990)]. After introduction of 4 μg of plasmid per $1.6 \times 10^6$ cells, the cells were suspended in 8 ml of RPMI1640-ITPSGF medium [RPMI1640 medium supplemented with 1/40 volume of 7.5% $NaHCO_3$, 3% of 200 mM L-glutamine solution (Gibco), 0.5 of a penicillin-streptomycin solution (Gibco; 5,000 units/ml penicillin, 5,000 μg/ml streptomycin), N-2-hydroxyethylpiperazine-N'-2-hydroxypropane-3-sulfonicacid (HEPES) (10 mM), insulin (3 μg/ml), transferrin (5 μg/ml), sodium pyruvate (5 mM), sodium selenite (125 nM), galactose (1 mg/ml) and Pluronic F68 (0.1% w/v); Nissui Pharmaceutical] and cultured in a $CO_2$ incubator at 37° C. for 24 hours. Then, G418 (Gibco) was added to a concentration of 0.5 mg/ml and the incubation was further continued for 7 days, whereby transformants were obtained. The transformants obtained were cultured in RPMI1640-ITPSGF medium containing 0.5 mg/ml of G418 and then about $3 \times 10^7$ cells were subjected to indirect immunofluorescent staining using an antibody against sialyl Lewis x carbohydrate chain, KM93 [Furuya et al.: Anticancer Research, 12, 27 (1992)]. Specifically, the following procedure was followed.

About $3 \times 10^7$ cells were placed in a 50-ml centrifugal tube (2059 tube; Falcon) and the cells were collected by centrifugation (130×g, 10 minutes). Then, the cells were washed with 20 ml of phosphate-buffered saline (PBS) containing 0.1% sodium azide [A-PBS; 8 g/l NaCl, 0.2 g/l KCl, 1.15 g/l $Na_2HPO_4$ (anhydrous), 0.2 g/l $KH_2PO_4$, 0.1 sodium azide]. To the cells collected was added 0.8 ml of KM93 (10 μg/ml; dissolved in A-PBS) for suspending the cells therein, and the reaction was carried out at 4° C. for 1 hours. The cells were rinsed with two portions of A-PBS and, then, 320 μl of anti-mouse IgG antibody/IgM antibody fluorescence-labeled with fluorescein isothiocyanate (FITC) (Kirkegaad & Perry Laboratories; 16-fold diluted with A-PBS) was added thereto for suspending them therein, and the reaction was carried out at 4° C. for 30 minutes. The cells were then rinsed with two portions of A-PBS and suspended in 1 ml of A-PBS and cells high in fluorescence intensity (highest 1%) were aseptically recovered using a fluorescence activated cell sorter (EPICS Elite Flow Cytometer; Coulter). The cells recovered were cultured for multiplication in RPMI1640-ITPSGF medium containing 0.5 mg/ml of G418. The cells thus grown were repeatedly treated in the same manner for separating and concentrating cells showing high fluorescence intensity. In the second treatment, cells with high fluorescence intensity (highest 1%) were recovered and, in the third treatment, cells with high fluorescence intensity (highest 20%) were recovered. As a result, cells with increased fluorescence intensity, namely cells with increased expression of sialyl Lewis x, could be obtained. These cells were cultured in RPMI1640-ITPSGF medium containing 0.5 mg/ml of G418 and then the plasmid was recovered from about $5 \times 10^6$ cells by the Hart method [Robert F. Margolskee et al.: Molecular and Cellular Biology, 8, 2837 (1988)]. The plasmid recovered was introduced into *Escherichia coli* LE392 by electroporation [William J. Dower et al.: Nucleic Acids Research, 16, 6127 (1988)] and an ampicillin-resistant strain was obtained. From that transformant, a plasmid was prepared using Qiagen's plasmid preparation kit and its structure was studied by cleaving with various restriction enzymes. It was found that the plasmid contains a cDNA of about 1.7 kb. This plasmid was named pAMoPRTH21 and again introduced into the strain KJM-1 by the method described above. Indirect immunofluorescence staining using KM93 revealed that the level of expression of sialyl Lewis x was about 10 times higher in the strain KJM-1 harboring that plasmid as compared with the strain KJM-1 harboring the control plasmid (pAMoPRC3Sc). The above results indicate that cDNA is the cDNA coding for α-1,3-fucosyltransferase participating in the production of sialyl Lewis x.

Figure 16:
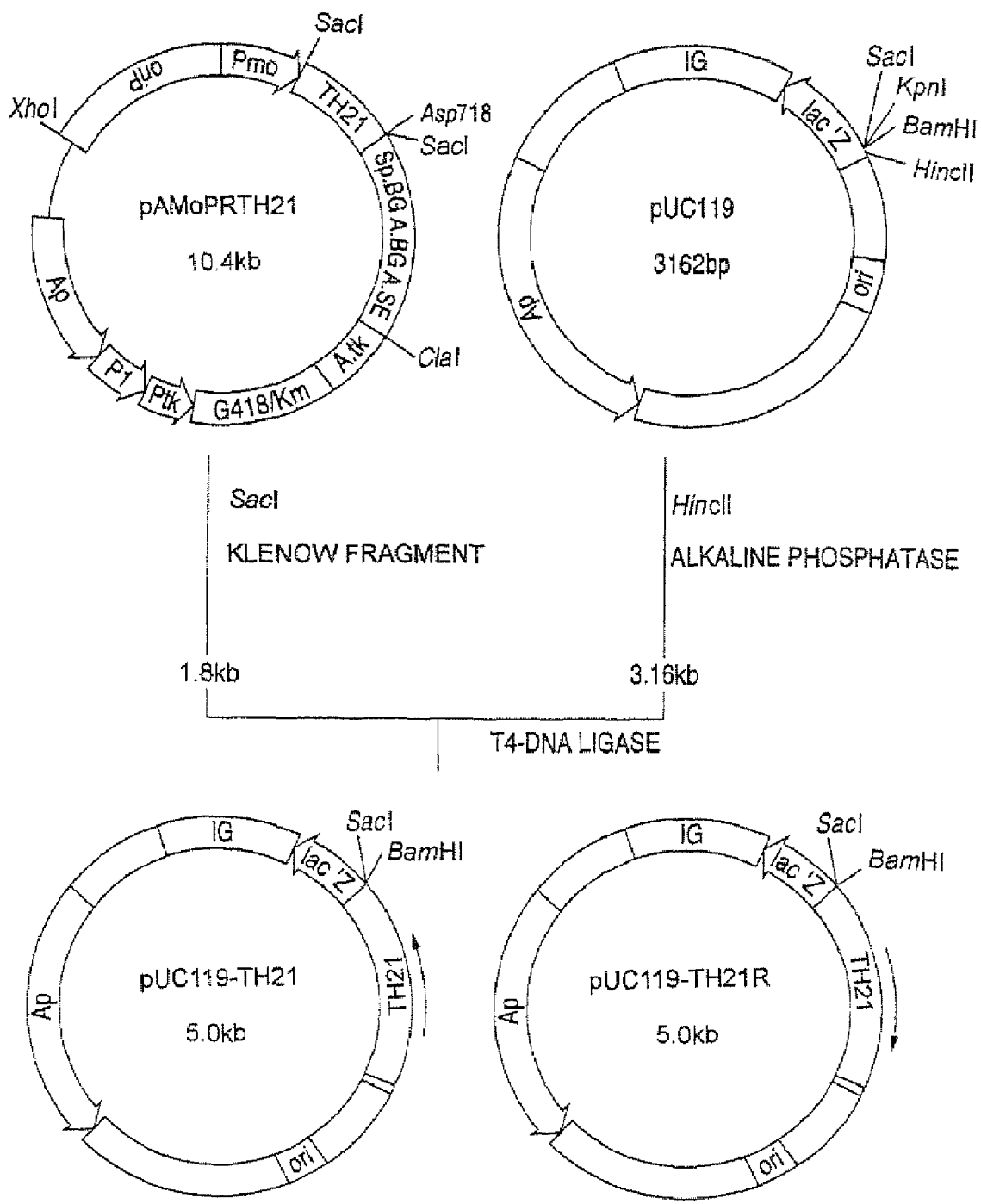
FIG. 16 shows a construction scheme for the plasmids pUC119-TH21 and pUC119-TH21R.

3. Base Sequence Determination of cDNA (TH21) Coding for α-1,3-fucosyltransferase (1) Insertion into pUC119 of cDNA (TH21) Coding for α-1, 3-fucosyltransferase (cf. FIG. 16)

pAMoPRTH21 (2 μg) was dissolved in 50 μl of Y-0 buffer, 30 units of SacI was added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 3' cohesive end formed upon SacI digestion to a blunt end. The reaction mixture was subjected to agarose gel electrophoresis and a DNA fragment of about 1.8 kb was recovered.

Separately, 1 μg of pUC119 [Messing et al.: Methods in Enzymology, 153, 3 (1987)] was dissolved in 30 μl of Y-100 buffer, 20 units of HincII was added and the digestion reaction was carried out at 37° C. for 2 hours. Then, 30 μl of 1 M Tris-HCl (pH 8.0) and 1 unit of *Escherichia coli*-derived alkaline phosphatase (Takara Shuzo) was added and the dephosphorylation reaction was carried out at 37° C. for 2 hours. After precipitation with ethanol, the precipitate was dissolved in 30 μl of TE buffer, the solution was subjected to agarose gel electrophoresis and a DNA fragment of about 3.16 kb was recovered.

The pAMoPRTH21-derived SacI (blunt end) fragment (1.8 kb; 0.05 μg) and pUC119-derived HincII fragment (3.16 kb; 0.05 μg) respectively obtained as described above were dissolved in 30 μl of T4 ligase buffer, 175 units of T4 DNA ligase and the ligation reaction was carried out at 12° C. for 16 hours. The reaction mixture was used to transform *Escherichia coli* JM105 [Yanisch-Perron et al.: Gene, 33, 103 (1985)] by the method of Cohen et al. and ampicillin-resistant strains were obtained. Plasmids were isolated from these transformants by a known method and the structure of each plasmid was identified by digestion with restriction enzymes. Two plasmids differing in the direction in pUC119 of the pAMoPRTH21-derived SacI (blunt end) fragment were isolated and named pUC119-TH21 and pUC119-TH21R, respectively.

(2) Construction of Deletion-Mutated Plasmid for Sequencing pUC119-TH21 (2 μg) and pUC119-TH21R (2 μg) were respectively dissolved in 30 μl of Y-0 buffer, 50 units of SacI was added and the digestion reaction was carried out at 37° C. for 16 hours. Then, NaCl was added to an NaCl concentration of 100 mM, 40 units of BamHI was added and the digestion reaction was further carried out at 37° C. for 2 hours. After precipitation with ethanol, each precipitate was dissolved in 100 μl of ExoIII buffer (attached to Takara Shuzo's deletion kit for kilosequencing).

The pUC119-TH21-derived SacI-BamHI fragment and pUC119-TH21R-derived SacI-BamHI fragment respectively obtained as described above were used to prepare a total of 21 deletion-mutated plasmids using Takara Shuzo's deletion kit for kilosequencing. The reagents and procedure used were as described in the manual attached to the kit.

The deletion plasmids obtained in the above manner were sequenced using an Applied Biosystems' sequencing kit (Taq DyeDeoxy™ Terminator Cycle Sequencing Kit; article number 401113). The thus-determined base sequence is shown as SEQ ID NO:1). As a result, it was revealed that TH21 encodes a protein composed of 342 amino acid residues. It was further revealed that said protein has structure common to glycosyltransferases (GTs). Apparently, it has a structure such that it reaches out the N-terminal 13 amino acid residues on the cytoplasm side, binds to the membrane by means of the highly hydrophobic region composed of the subsequent 24 amino acid residues and exposes the remaining majority C-terminal portion (including the catalytic site) to the Golgi body inside. Comparison, from the amino acid sequence viewpoint, with the known glycosyltransferases so far structurally identified revealed that it is 30% to 40% homologous with FucT-III, FucT-IV, FucT-V and FucT-VI. The following facts indicate that TH21 codes for a novel α-1,3-fucosyltransferase: that when TH-21 is expressed in Namalwa cells, the expression of sialyl Lewis x increases, that the protein encoded by TH21 shares homology with fucosyltransferases and that the protein encoded by TH21 differs in amino acid sequence from the known glycosyltransferases described above.

EXAMPLE 2

Synthesis of Sialyl Lewis x Carbohydrate Chain in KJM-1 Strain with Fucosyltransferase Expression Plasmid Introduced Therein The plasmids pAMoPRC3Sc (direct expression cloning vector; control) and pAMoPRTH21 (fucosyltransferase expression plasmid) were prepared using Qiagen's plasmid preparation kit>plasmid<maxi kit (article number 41031) The plasmids obtained were precipitated with ethanol and then dissolved in TE buffer to a concentration of 1 μg/μl. Both the plasmids were then introduced into Namalwa KJM-1 by electroporation [Miyaji et al.: Cytotechnology, 3, 133 (1990)]. After introduction of 4 μg of plasmid per $1.6 \times 10^6$ cells, the cells were suspended in 8 ml of RPMI1640-ITPSGF medium and cultivated in a $CO_2$ incubator at 37° C. for 24 hours. Then, G418 (Gibco) was added to a concentration of 0.5 mg/ml and cultivation was continued for 7 days. Thereafter, 22 ml of RPMI1640-ITPSGF medium (containing 0.5 mg/ml of G418) was added and cultivation was further conducted for 5 days. The thus-obtained transformants were cultured in RPMI1640-ITPSGF medium containing 0.5 mg/ml of G418. About 1×10⁶ cells of each culture were placed in a microtube (1.5 ml; Eppendorf) and centrifuges (550×g, 7 minutes). The thus-collected cells were washed with 1 ml of phosphate-buffered saline (PBS) containing 0.1% sodium azide [A-PES; 8 g/l NaCl, 0.2 g/l KCl, 1.15 g/l $Na_2HPO_4$, (anhydrous), 0.2 g/l $KH_2PO_4$, 0.1% sodium azide]. The cells collected were subjected to indirect immunofluorescence staining using a mouse antibody of the class IgM against sialyl Lewis x carbohydrate chain, CSLEX1 [Fukushima et al.: Cancer Research, 44, 5279 (1984)], and a mouse antibody of the class IgM, KM93 [Furuya et al.: Anticancer Research, 12, 27 (1992)] for checking the expression of sialyl Lewis x carbohydrate chain in these cells. To the cells collected was added 50 µl (10 µg/ml) of CSLEX1 or KM93 for suspending the cells and the reaction was carried out at 4° C. for 1 hour. Then, the cells were washed with 3 portions of A-PBS, 20 µl of an anti-mouse IgG antibody/IgM antibody fluorescence-labeled with fluorescein isothiocyanate (TITC) (Kirkegaad & Perry Laboratories; used after 16-fold dilution with A-PBS) was added and the reaction was carried out at 4° C. for 30 minutes. The cells were washed with 3 portions of A-PBS, then again suspended in A-PBS and analyzed using an EPICS Elite flow cytometer (Coulter).

As a control, an experiment was carried out in the same manner as mentioned above using a serum collected from a normal BALB/c mouse (used after 500-fold dilution with A-PBS) in lieu of CSLEX1 or KM93.

Figure 17A:
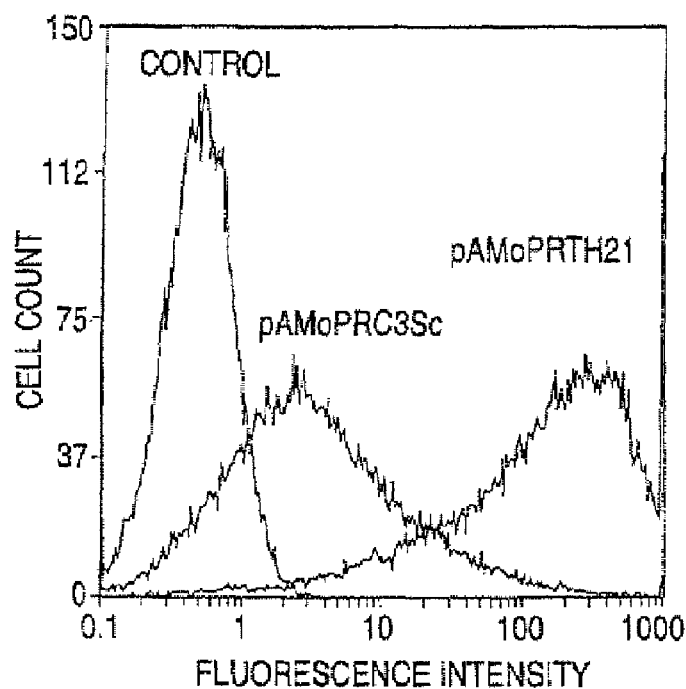
FIG. 17 shows the results of analysis on an EPICS Elite flow cytometer (Coulter) following indirect immunofluorescent staining. In the figure, data a show the results obtained by subjecting the KJM-1 strain after introduction therein of pAMoPRC3Sc (control plasmid) or pAMoPRTH21 (α-1,3-fucosyltransferase expression plasmid) to indirect immunofluorescent staining using CSLEX1, while data b show the results obtained by subjecting the KJM-1 strain after introduction therein of pAMoPRC3Sc (control plasmid) or pAMoPRTH21 (α-1,3-fucosyltransferase expression plasmid) to indirect immunofluorescent staining using KM93. In both cases, the results obtained by subjecting the KJM-1 strain after introduction therein of pAMoPRC3Sc (control plasmid) to indirect immunofluorescent staining using normal mouse serum are shown as controls.
Figure 17B:
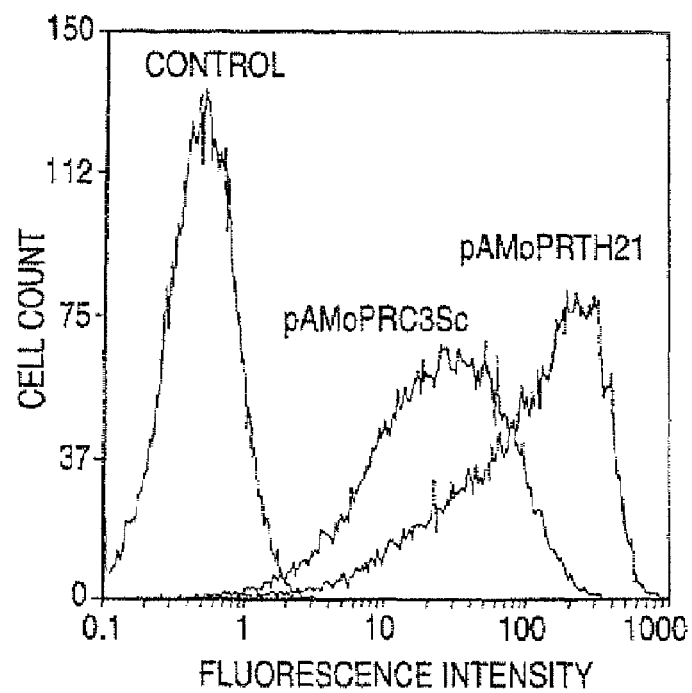

The results thus obtained are shown in FIG. 17. It is evident that, for the KJM-1 strain harboring the indirect expression cloning vector pAMoPRC3Sc (control plasmid) introduced therein, the fluorescence intensity of the cells stained with CSLEX1 or KM93 is higher as compared with the fluorescence intensity of the control. This means that the KJM-1 strain is originally capable of expressing the sialyl Lewis x carbohydrate chain. Further, it is evident that the fluorescence intensity of the KJM-1 strain harboring pAMoPRTH21 (fucosyltransferase expression plasmid) as stained with CSLEX1 or KM93 is still higher than the fluorescence intensity of the KJM-1 strain harboring pAMoPRC3Sc (control plasmid) as stained with CSLEX1 or KM93. This indicates that the sialyl Lewis x carbohydrate chain can be newly synthesized on the carbohydrate chain of a glycoprotein or glycolipid on the cell surface by causing intracellular expression of fucosyltransferase encoded by TH21 and, further, that the sialyl Lewis x carbohydrate chain can be synthesized as well on a glycoprotein secreted from the cells allowed to produce fucosyltransferase. Therefore, it is possible to produce and cause to be secreted a useful glycoprotein using those cells that produce fucosyltransferase and provide the glycoprotein produced with the sialyl Lewis x carbohydrate chain and have same secreted it was also found out that since the sialyl Lewis x carbohydrate chain can be synthesized, the fucosyltransferase encoded by TH21 has α-1,3-fucosyltransferase activity.

EXAMPLE 3

Secretory Production of α-1,3-fucosyltransferase (TH21) in KJM-1 Cells

Figure 18:
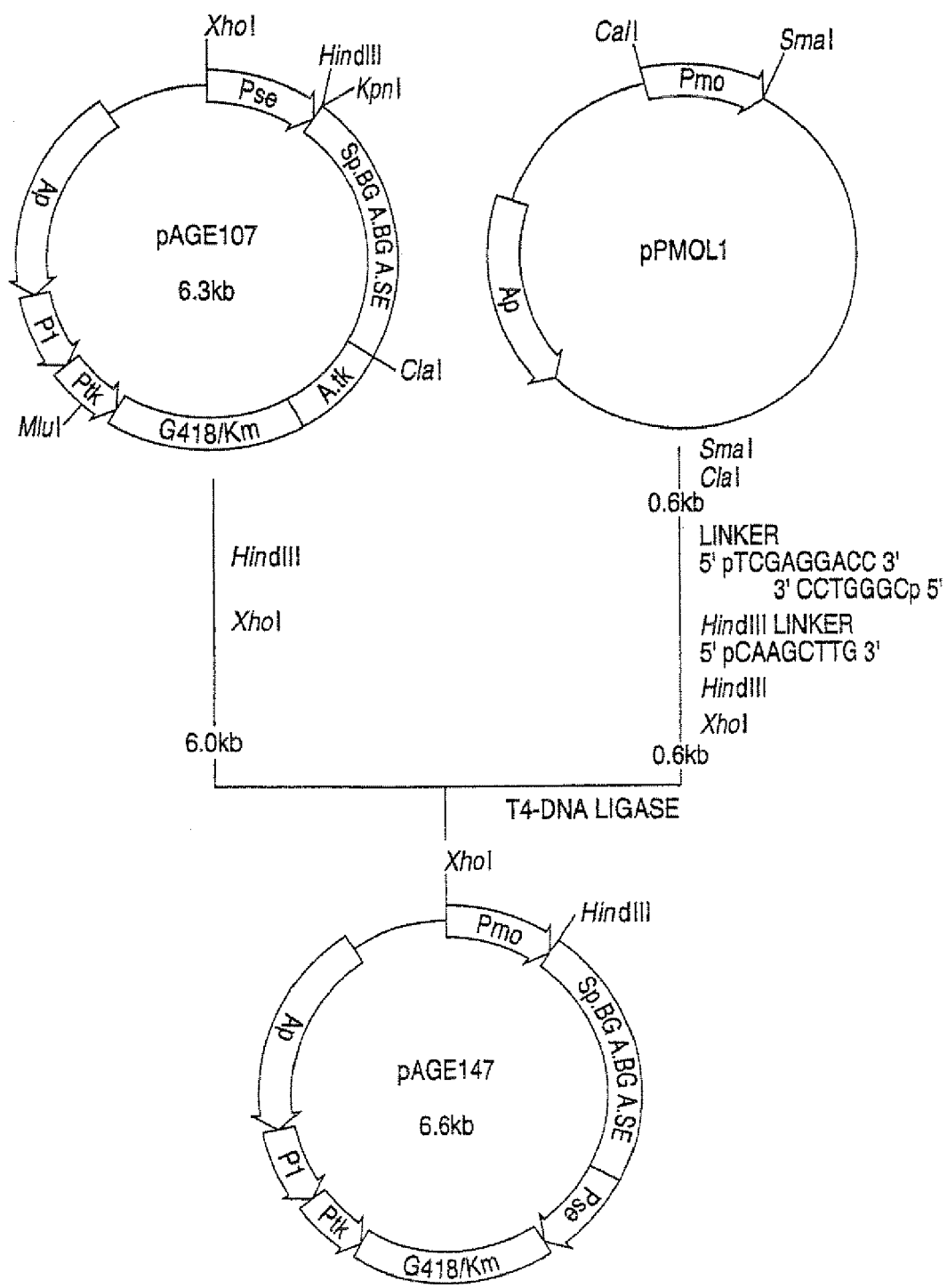
FIG. 18 shows a construction scheme for the plasmid pAGE147.

1. Construction of Secretory Expression Vector pAMoPRSA (1) Construction of pAGE147 (cf. FIG. 18)

A plasmid, pAGE147, was constructed in the manner described below by replacing the SV40 early gene promoter of pAGE107 with the LTR promoter of the Moloney murine leukemia virus.

The plasmid pPMOL1 (JP-A-1-63394; 2 µg) was dissolved in 30 µl of Y-0 buffer, 20 units of SmaI was added and the digestion reaction was carried out at 30° C. for 3 hours. Then, NaCl was added to a concentration of 50 mM, 20 units of ClaI was added and the digestion reaction was carried out at 37° C. for 2 hours. The reaction mixture was subjected to agarose gel electrophoresis and a DNA fragment (about 0.6 kb) containing the LTR promoter of the Moloney murine leukemia virus was recovered.

Separately, 25 picomoles each of the two DNA linkers synthesized in Example 1, section 1-(8) were dissolved in 10 ml of T4 kinase buffer, 5 units of T4 DNA kinase was added and the reaction was carried out at 37° C. for 30 minutes for the phosphorylation at the 5' end.

The pPMOL1-derived ClaI-SmaI fragment (0.6 kb; 0.05 mg) and two 5'-phosphorylated synthetic DNAs (1 picomole each) respectively obtained as described above and a HindIII linker (5'-pCAAGCTTG-3'; Takara Shuzo; 1 picomole) were dissolved in 30 µl of T4 ligase buffer, 200 units of T4 DNA ligase was added and the ligation reaction was carried out at 12° C. for 16 hours. The resulting DNA fragment was recovered by precipitation with ethanol and dissolved in Y-100 buffer, 10 units of HindIII and 10 units of XhoI were added and the digestion reaction was carried out at 37° C. for 2 hours. The reaction was terminated by extraction with phenol and chloroform and the DNA fragment was recovered by precipitation with ethanol.

Separately, 1 µg of pAGE107 [JP-A-3-22979; Miyaji et al.: Cytotechnology, 3, 133 (1990)] was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 6.0 kb) containing the G418 resistance gene and ampicillin resistance gene was recovered.

The pAGE107-derived HindIII-XhoI fragment (6.0 kb; 0.3 µg) and pPMOL1-derived HindIII-XhoI fragment (0.6 kb; 0.01 µg) respectively obtained as described above were dissolved in 20 µl of T4 ligase buffer, 200 units of T4 DNA ligase was added and the ligation reaction was carried out at 12° C. for 16 hours.

The reaction mixture was used to transform *Escherichia coli* HB101 by the method of Cohen et al. and an ampicillin resistant strain was obtained. A plasmid was isolated from this transformant by a known method. This plasmid was named pAGE147 and its structure was identified by digestion with restriction enzymes.

Figure 19:
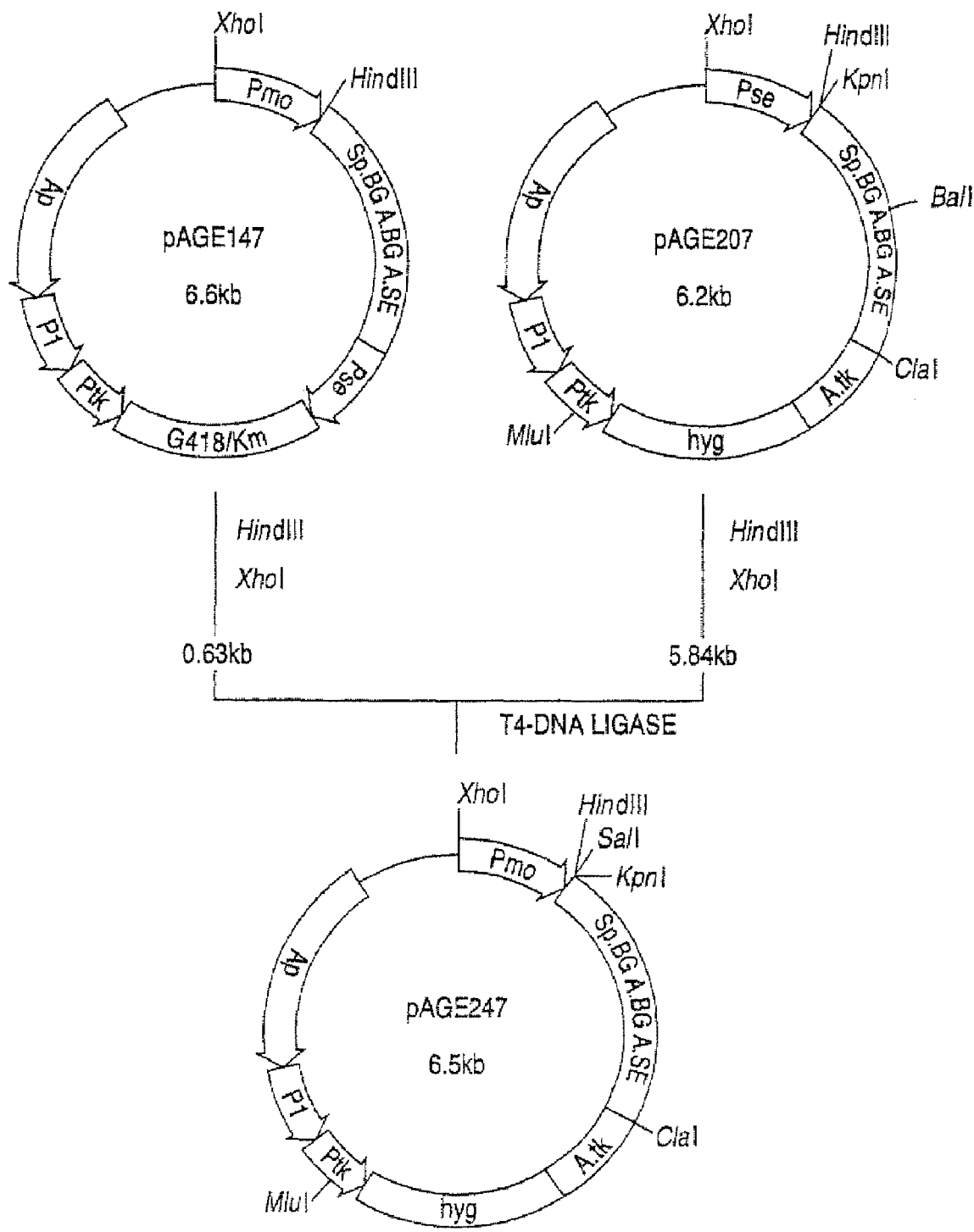
FIG. 19 shows a construction scheme for the plasmid pAGE247.

(2) Construction of pAGE247 (cf. FIG. 19)

A plasmid, pAGE247, was constructed in the manner described below by replacing the SV40 early gene promoter of pAGE207 with the LTR promoter of the Moloney murine leukemia virus.

pAGE147 (2 µg) obtained in (1) was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 0.63 kb) containing the Moloney murine leukemia virus LTR promoter was recovered.

Separately, pAGE207 (2 µg) constructed in Example 1, section 1-(11) was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 5.84 kb) containing the hygromycin resistance gene and ampicillin resistance gene was recovered.

The pAGE147-derived HindIII-XhoI fragment (0.63 kb; 0.05 µg) and pAGE207-derived HindIII-XhoI fragment (5.84 kb; 0.1 µg) respectively obtained as described above were dissolved in 30 µl of T4 ligase buffer, 100 units of T4 DNA ligase was added and the ligation reaction was carried out at 12° C. for 16 hours.

The reaction mixture was used to transform *Escherichia coli* HB101 by the method of Cohen et al. and an ampicillin-resistant strain was obtained. A plasmid was isolated from this transformant by a known method. This plasmid was named pAGE247 and its structure was identified by digestion with restriction enzymes.

Figure 20:
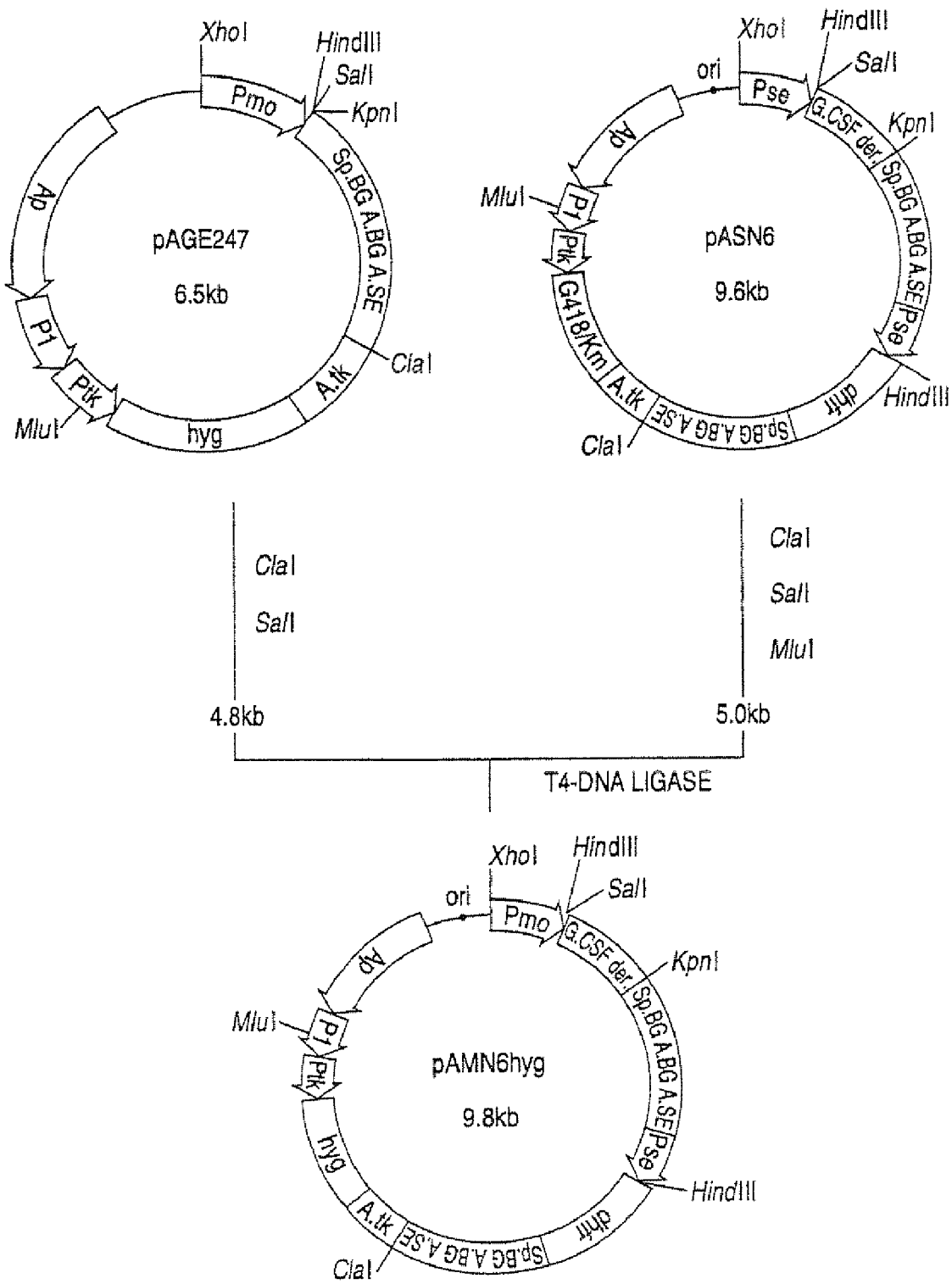
FIG. 20 shows a construction scheme for the plasmid pAMN6hyg.

(3) Construction of pAMN6hyg (cf. FIG. 20)

An expression plasmid, pAMN6hyg, for a human granulocyte colony stimulating factor derivative was constructed with the Moloney murine leukemia virus LTR as a promoter and the hygromycin resistance gene as a marker, as follows.

pAGE247 (2 µg) obtained as described above was dissolved in 30 µl of Y-50 buffer, 20 units of Cla: was added and the digestion reaction was carried out at 37° C. for 2 hours. Then, NaCl was added to a concentration of 175 mM, 20 units of SalI was added and the digestion reaction was carried out at 37° C. for 2 hours. The reaction mixture was subjected to agarose gel electrophoresis and a DNA fragment (about 4.8 kb) containing the Moloney murine leukemia virus LTR promoter, ampicillin resistance gene and hygromycin resistance gene was recovered.

Separately, the plasmid pASN6 (2 µg) obtained by the method disclosed in JP-A-2227075 was dissolved in 30 µl of Y-50 buffer, 20 units of ClaI was added and the digestion reaction was carried out at 37° C. for 2 hours. Then, NaCl was added to a concentration of 175 mM, 20 units of SalI and 20 units of MluI were added and the digestion reaction was carried out at 37° C. for 2 hours. The reaction mixture was subjected to agarose gel electrophoresis and a DNA fragment (about 5.0 kb) containing the human granulocyte colony stimulating factor derivative gene was recovered.

The pAGE247-derived ClaI-SalI fragment (4.8 kb; 0.1 µg) and pASN6-derived ClaI-SalI fragment (5.0 kb; 0.1 µg) respectively obtained as described above were dissolved in 20 µl of T4 ligase buffer, 200 units of T4 DNA ligase was added and the ligation reaction was carried out at 12° C. for 16 hours.

The reaction mixture was used to transform *Escherichia coli* HB101 by the method of Cohen et al. and an ampicillin-resistant strain was obtained. A plasmid was isolated from this transformant by a known method. This plasmid was named pAMN6hyg and its structure was identified by digestion with restriction enzymes.

Figure 21:
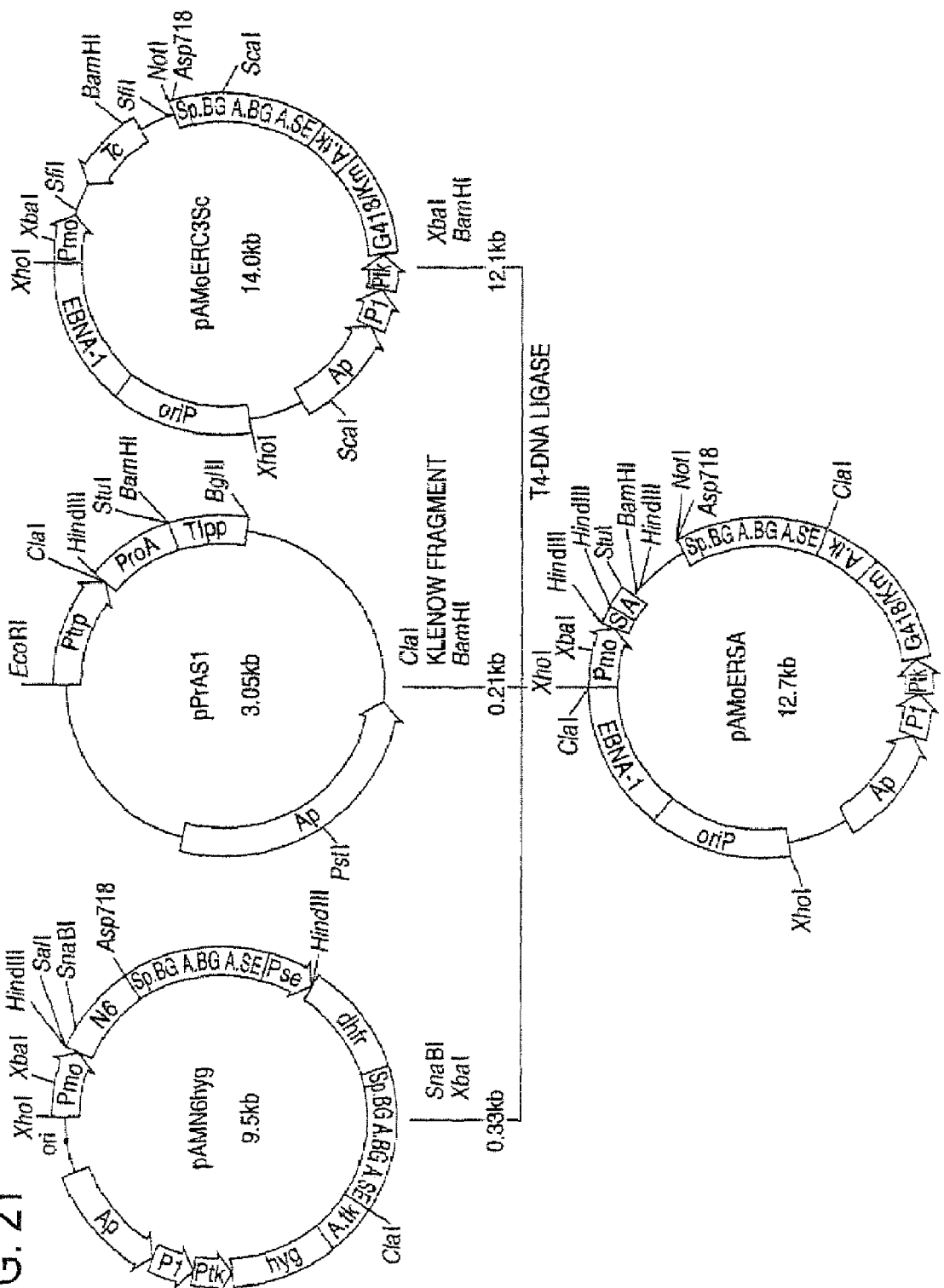
FIG. 21 shows a construction scheme for the plasmid pAMoERSA.

(4) Construction of pAMoERSA (cf. FIG. 21)

A vector, pAMoERSA, for secretory expression of α-1,3-fucosyltransferase in a form fused to the immunoglobulin G (IgG) binding region of *Staphylococcus aureus* protein A was constructed in the following manner.

pAMN6hyg (2 µg) obtained in (3) was dissolved in 30 µl of Y-50 buffer, 20 units of SnaBI was added and the digestion reaction was carried out at 37° C. for 2 hours. Then, NaCl was added to a concentration of 100 mM, 20 units of XbaI was added and the digestion reaction was carried out at 37° C. for 2 hours. The reaction mixture was subjected to agarose gel electrophoresis and a DNA fragment (about 0.33 kb) containing the human granulocyte colony stimulating factor signal sequence was recovered.

Separately, 2 µg of pPrAS1 [Saito et al.: Protein Engineering, 2, 481 (1989)] was dissolved in 30 µl of Y-50 buffer, 20 units of ClaI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end formed upon ClaI digestion to a blunt end. The reaction was terminated by extraction with phenol. After extraction with chloroform and precipitation with ethanol, the precipitate was dissolved in 30 µl of Y-100 buffer, 20 units of BamHI was added and the digestion reaction was carried out at 37° C. for 2 hours. The reaction mixture was subjected to agarose gel electrophoresis and a DNA fragment (about 0.21 kb) containing the IgG binding region of protein A was recovered.

Further, separately, 2 µg of pAMoERC3Sc obtained in Example 1, section 1-(13) was dissolved in 30 µl of Y-100 buffer, 20 units of XbaI and 20 units of BamHI were added and the digestion reaction was carried out at 37° C. for 2 hours. The reaction mixture was subjected to agarose gel electrophoresis and a DNA fragment of about 12.1 kb was recovered.

The pAMN6hyg-derived SnaBI-XbaI fragment (0.33 kb; 0.05 µg), pPrAS1-derived ClaI (blunt end)-BamHI fragment (0.21 kb; 0.05 µg) and pAMoERC3Sc-derived XbaI-BamHI fragment (12.1 kb; 0.1 µg) respectively obtained as described above were dissolved in 30 µl of T4 ligase buffer, 175 units of T4 DNA ligase was added and the ligation reaction was carried out at 12° C. for 16 hours.

The reaction mixture was used to transform *Escherichia coli* HB101 by the method of Cohen et al. and an ampicillin-resistant strain was obtained. A plasmid was isolated from this transformant by a known method. This plasmid was named pAMoERSA and its structure was identified by digestion with restriction enzymes.

Figure 22:
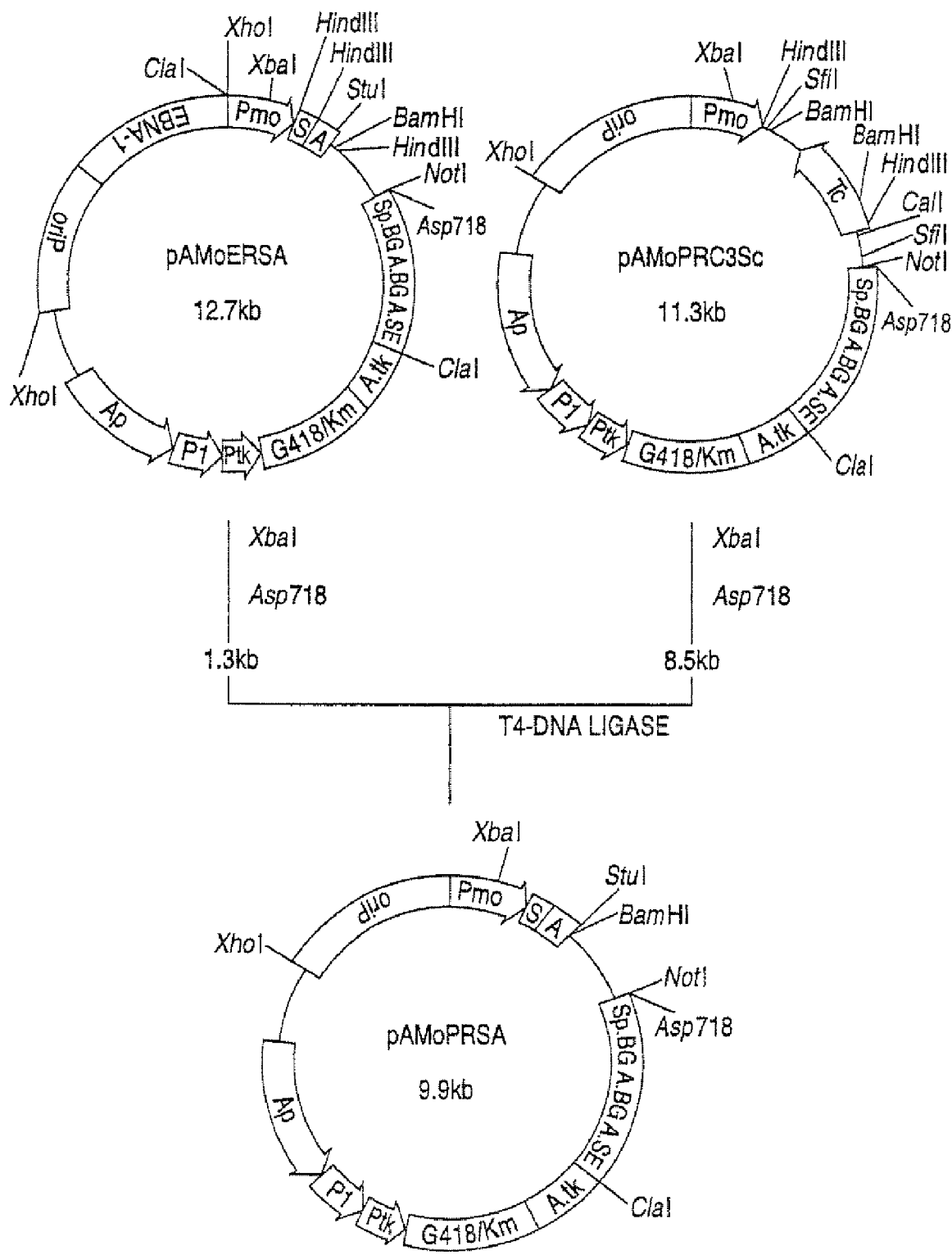
FIG. 22 shows a construction scheme for the plasmid pAMoPRSA.

(5) Construction of pAMoPRSA (cf. FIG. 22)

A plasmid, pAMoPRSA, was constructed by eliminating the EBNA-1 gene from pAMoERSA in the manner described below. pAMoPRSA can be used as a secretory expression vector like pAMoERSA.

pAMoERSA (2 µg) was dissolved in 30 µl of a buffer comprising 10 mM Tris-HCl (pH 7.5), 6 mM $MgCl_2$, 80 mM NaCl and 6 mM 2-mercaptoethanol (hereinafter referred to as "Y-80 buffer"), 20 units of XbaI and 20 units of Asp718 (Boehringer Mannheim) were added and the digestion reaction was carried out at 37° C. for 2 hours. The reaction mixture was subjected to agarose gel electrophoresis and a DNA fragment of about 1.3 kb was recovered.

Separately, 2 µg of pAMoPRC3Sc was dissolved in 30 µl of Y-100 buffer, 20 units of XbaI and 20 units of Asp718 were added and the digestion reaction was carried out at 37° C. for 2 hours. The reaction mixture was subjected to agarose gel electrophoresis and a DNA fragment of about 8.5 kb was recovered.

The pAMoERSA-derived XbaI-Asp718 fragment (1.3 kb; 0.05 µg) and pAMoPRC3Sc-derived XbaI-Asp718 fragment (8.5 kb; 0.1 µg) obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant by a known method. This plasmid was named pAMoPRSA and its structure was identified by digestion with restriction enzymes.

2. Cloning of α-2,3-sialyltransferase (WM17) cDNA from WM266-4 Cells (Human Melanoma Cell Line) and Secretory Production of α-2,3-sialyltransferase (WM17)

(1) Cloning of α-2,3-sialyltransferase (WM17) cDNA from WM266-4 Cells, i.e. Human Melanoma Cells (a) Testing of Namalwa Cells for Resistance Against *Ricinus communis* Lectin 120

The resistance of the KJM-1 strain against castor bean lectin 120 was investigated by culturing the KJM-1 strain in the presence of *Ricinus communis* lectin 120 in various concentrations. Thus, cells of the KJM-1 strain were suspended in RPMI1640-ITPSGF medium at a concentration of $5\times10^4$ cells/ml and the suspension was distributed in 200 μl portions into wells of a 96-well microliter plate. Thereto were added various concentrations of *Ricinus communis* lectin 120 (Seikagaku Corp.) in 1/100 volume portions and incubation was performed in a $CO_2$ incubator at 37° C. for 3 weeks. As a result, the minimum concentration of *Ricinus communis* lectin 120 required for completely inhibiting the growth of the KJM-1 strain was found to be 50 ng/ml. With $4\times10^6$ KJM-1 strains tested, any spontaneous appearance of *Ricinus communis* lectin 120-resistant strains could not be noted at that concentration.

(b) Isolation of mRNA from WM266-4 Cells, i.e. Human Melanoma Cells

About 30 μg of mRNA was obtained from $1\times10^8$ WM266-4 cells using Invitrogen's mRNA extraction kit Fast Track (article number K1593-02). (The reagents and procedure actually used or followed were as described in the manual attached to the kit.)

(c) Construction of cDNA Library

Starting from 8 μg of the mRNA obtained as described above, double-stranded cDNA was synthesized using Invitrogen's cDNA synthesis kit The Librarian I, with random primers as primers. The double-stranded cDNA synthesized and the SfiI linker (4 μg of the 11 mer and 2.9 μg of the 8 mer) prepared in the same manner as in Example 1, section 2-(2) were dissolved in 45 μl of T4 ligase buffer, 1,050 units of T4 DNA ligase was added and the ligation reaction was carried out at 16° C. for 16 hours. The reaction mixture was subjected to agarose gel electrophoresis and cDNA fragments not less than about 1.2 kb in size were recovered.

Separately, 24 μg of the expression cloning vector pAMoPRC3Sc was dissolved in 590 μl of Y-50 buffer, 80 units of SfiI was added and the digestion reaction was carried out at 37° C. for 16 hours. A 5-μl portion of the reaction mixture was subjected to agarose gel electrophoresis for confirming completion of the cleavage. Thereafter, for decreasing the proportion of clones lacking in cDNA, 40 units of BamHI was added and the digestion reaction was further carried out at 37° C. for 2 hours. The reaction mixture was subjected to agarose gel electrophoresis and a DNA fragment of about 8.8 kb was recovered.

The pAMoPRC3Sc-derived SfiI fragment (8.8 kb; 2 μg) obtained as described above and the cDNA purified in the above manner were dissolved in 250 μl of T4 ligase buffer, 2,000 units of T4 DNA ligase was added and the ligation reaction was carried out at 16° C. for 16 hours. Then, 5 μg of transfer RNA (tRNA) was added for ethanol was added for causing precipitation and the precipitate was dissolved in 20 μl of TE buffer. The reaction mixture was used to transform *Escherichia coli* LE392 by electroporation and about $2\times10^5$ ampicillin-resistant strains.

(d) Cloning of α-2,3-sialyltransferase (WM17) cDNA Utilizing Resistance Development Against *Ricinus communis* Lectin 120

The about $2\times10^5$ ampicillin-resistant strains obtained as described above were mixed and plasmid preparation was performed using Qiagen's plasmid preparation kit>plasmid<maxi kit (article number 41031). The plasmid obtained was precipitated by addition of ethanol and dissolved in TE buffer in a concentration of 1 mg/ml.

The above plasmid was introduced into the KJM-1 strain by electroporation [Miyaji et al.: Cytotechnology, 3, 133 (1990)]. After introduction of 4 μg of plasmid per $1.6\times10^6$ cells, the cells were suspended in 8 μl of RPMI1640-ITPSGF medium and cultured in a $CO_2$ incubator at 37° C. for 24 hours. Then, G418 (Gibco) was added to a concentration of 0.5 mg/ml and cultivation was continued for 5 to 7 days, whereby transformant strains were obtained. The transformant strains obtained were suspended in RPMI1640-ITPSGF medium containing *Ricinus communis* lectin 120 (50 ng/ml) to a concentration of $5\times10^4$ cells/ml and the suspension was distributed in 200 μl portions into wells of 96-well microtiter plates. Cultivation was conducted in a $CO_2$ incubator at 37° C. for 4 weeks. A *Ricinus communis* lectin 120-resistant strain was thus obtained. The resistant strain was cultured and a plasmid was recovered from about $5\times10^6$ cells thereof by the Hart method [Robert F. Margolskee et al.: Molecular and Cellular Biology, 8, 2837 (1988)]. The plasmid recovered was introduced into *Escherichia coli* LE392 by electroporation [William J. Dower et al.: Nucleic Acids Research, 16, 6127 (1988)] and an ampicillin-resistant strain was obtained. From that transformant, a plasmid was prepared using Qiagen's plasmid preparation kit and its structure was investigated by cleaving with various restriction enzymes. It was thus revealed that it contains a cDNA of about 1.9 kb. This plasmid was named pAMoPRWM17 and introduced again into the KJM-1 strain by the same method as described above, whereupon the strain again developed resistance against *Ricinus communis* lectin 120. It thus became apparent that this cDNA is the gene causative of lectin resistance. The KJM-1 strain harboring pAMoPRWM17 introduced therein can grow in the presence of *Ricinus communis* lectin 120 at a concentration as high as 200 ng/ml.

Figure 23:
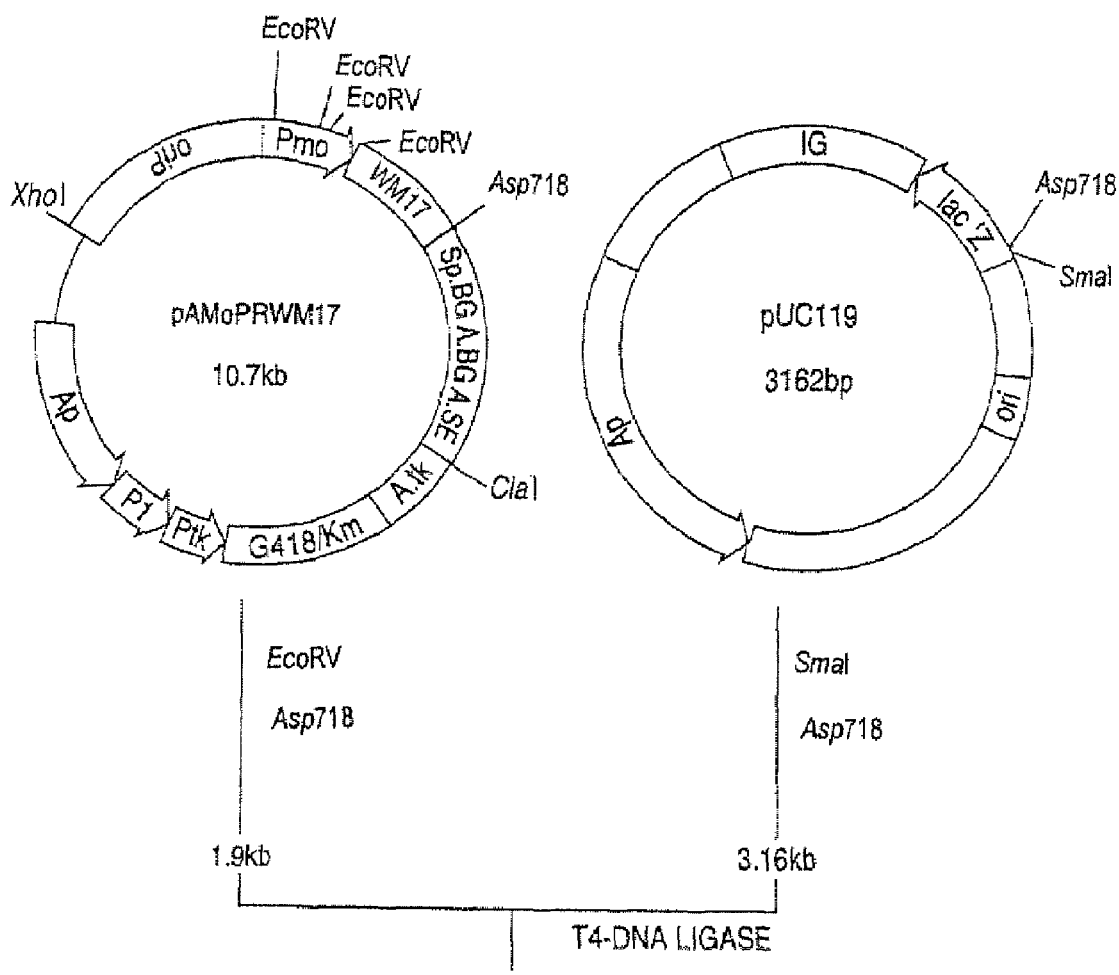
FIG. 23 shows a construction scheme for the plasmid pUC119-WM17.
Figure 23:
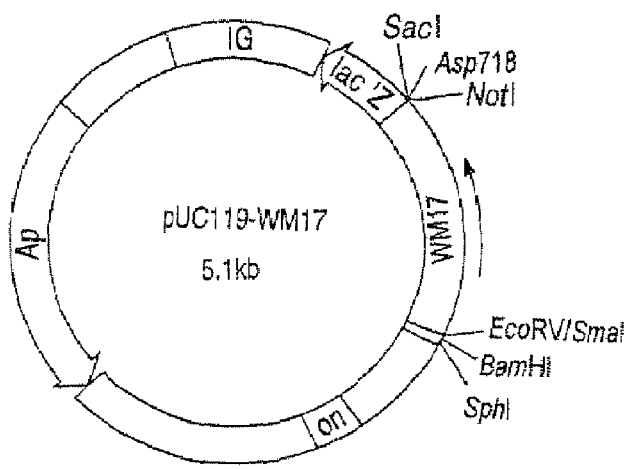

(2) Base Sequence Determination of α-2,3-sialyl Transferase (WM17) cDNA (a) Insertion of α-2,3-sialyltransferase (WM17) cDNA into pUC119 (cf. FIG. 23)

pAMoPRWM17 (1 mg) was dissolved in 30 μl of Y-100 buffer, 20 units of EcoRV and 20 units of Asp718 (Boehringer Mannheim) were added and the digestion reaction was carried out at 37° C. for 2 hours. The reaction mixture was subjected to agarose gel electrophoresis and a DNA fragment of about 1.9 kb was recovered.

Separately, 1 μg of pUC119 [Messing et al.: Methods in Enzymology, 153, 3 (1987)] was dissolved in 30 μl of K-20 buffer, 20 units of SmaI was added and the digestion reaction was carried out at 37° C. for 2 hours. Then, NaCl was added to an NaCl concentration of 100 mM, 20 units of Asp718 was added and the digestion reaction was further carried out at 37° C. for 2 hours. The reaction mixture was subjected to agarose gel electrophoresis and a DNA fragment of about 3.16 kb was recovered.

The pAMoPRWM17-derived EcoRV-ASp718 fragment (1.9 kb; 0.2 μg) and pUC119-derived SmaI-Asp-718 fragment (3.16 kb; 0.1 μg) obtained as described above were dissolved in 30 μl of T4 ligase buffer, 175 units of T4 DNA ligase was added and the ligation reaction was carried out at 12° C. for 16 hours.

The reaction mixture was used to transform *Escherichia coli* 101 by the method of Cohen et al. and an ampicillin-resistant strain was obtained. A plasmid was isolated from this transformant by a known method. This plasmid was named pUC119-WM17 and its structure was identified by digestion with restriction enzymes.

(b) Construction of Deletion-Mutated Plasmid for Sequencing pUC119-WM17 (2 μg) obtained in (a) was dissolved in 30 μl of Y-150 buffer, 20 units of BamHI and 20 units of SphI were added and the digestion reaction was carried out at 37° C. for 2 hours. After precipitation with ethanol, the precipitate was dissolved in 100 µl of ExoIII buffer (attached to Takara Shuzo's deletion kit for kilosequencing). Separately, 2 µg of the same plasmid was dissolved in 30 µl of Y-0 buffer, 20 units of SacI was added and the digestion reaction was carried out at 37° C. for 2 hours. Then, NaCl was added to an NaCl concentration of 150 mM, 20 units of NotI was added and the digestion reaction was further carried out at 37° C. for 2 hours. After precipitation with ethanol, the precipitate was dissolved in 100 µl of exonuclease III buffer.

Starting with the pUC119-WM17-derived BamHI-SphI and SacI-NotI fragments obtained as described above, scores of deletion-mutated plasmids were produced for each fragment using Takara Shuzo's deletion kit for kilosequencing. The reagents and procedure actually employed were as described in the manual attached to the kit.

The deletion-mutated plasmids obtained in the above were sequenced using Applied Biosystems' sequencing kit (Taq DyeDeoxy™ Terminator Cycle Sequencing Kit (article number 401113). The base sequence thus determined is shown as SEQ ID NO:6. The 1742 base pairs (bp) is followed by poly A. This base sequence indicates that this DNA codes for a protein composed of 329 amino acid residues. It is evident from the amino acid sequence that this protein has a structure common to glycosyltransferases. Thus, the protein is supposedly composed of the cytoplasmid region (8 amino acid residues) on the N-terminal side, the subsequent membrane binding region (18 amino acid residues) and the C-terminal region (303 amino acid residues) having catalytic activity.

Figure 24:
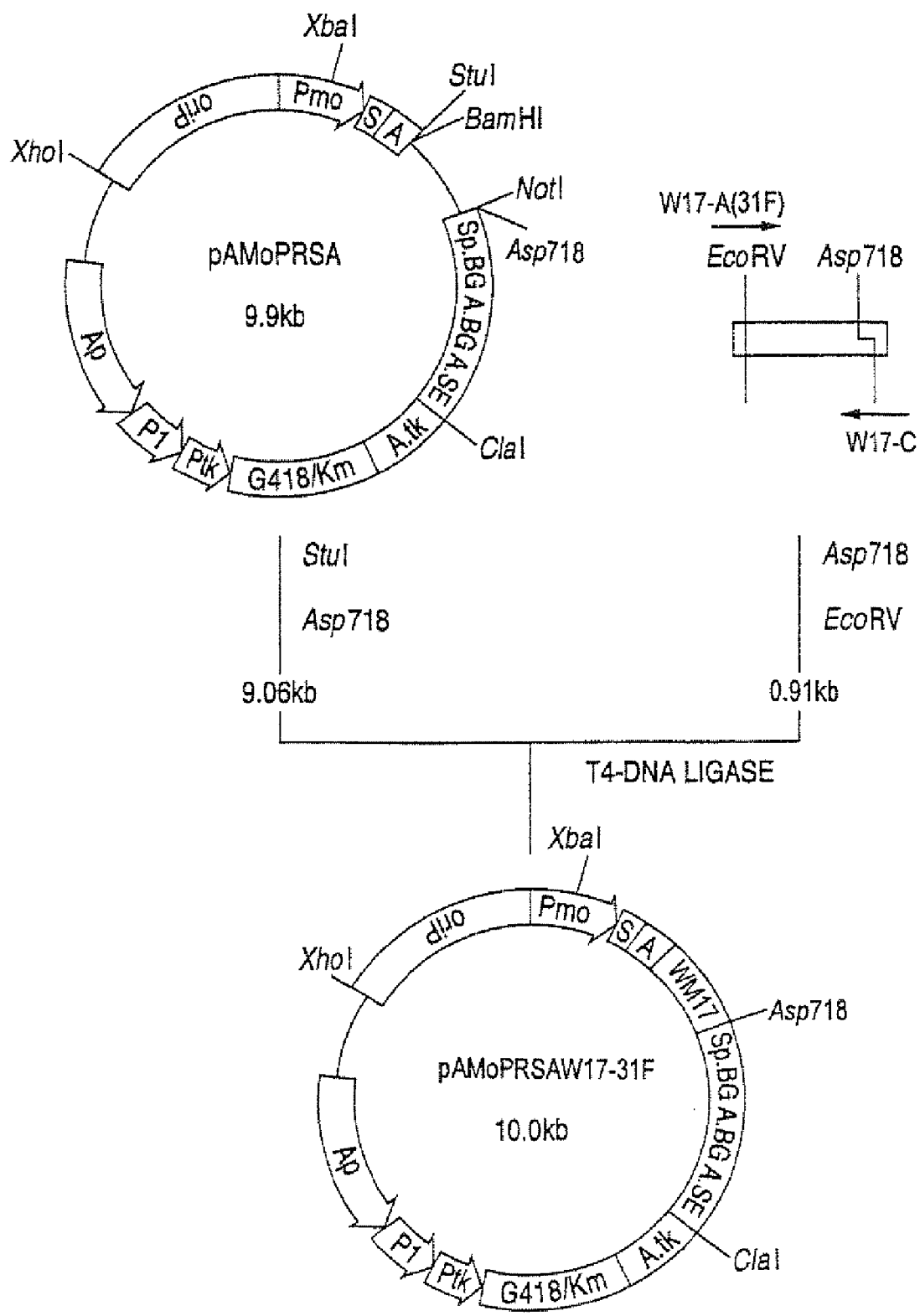
FIG. 24 shows a construction scheme for the plasmid pAMoPRSAW17-31F.
Figure 25:
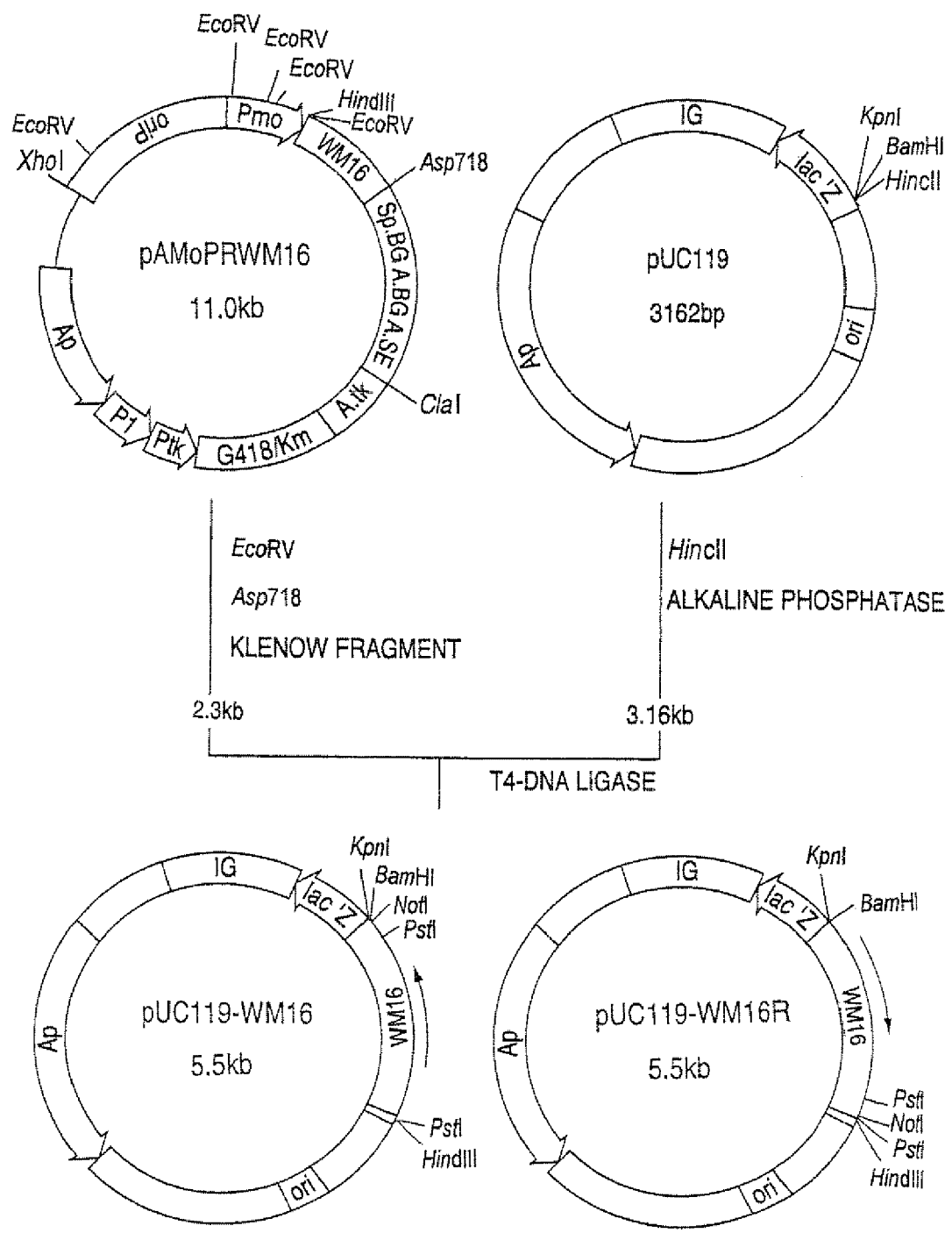
FIG. 25 shows a construction scheme for the plasmids pUC119-WM16 and pUC119-WM16R.
Figure 26:
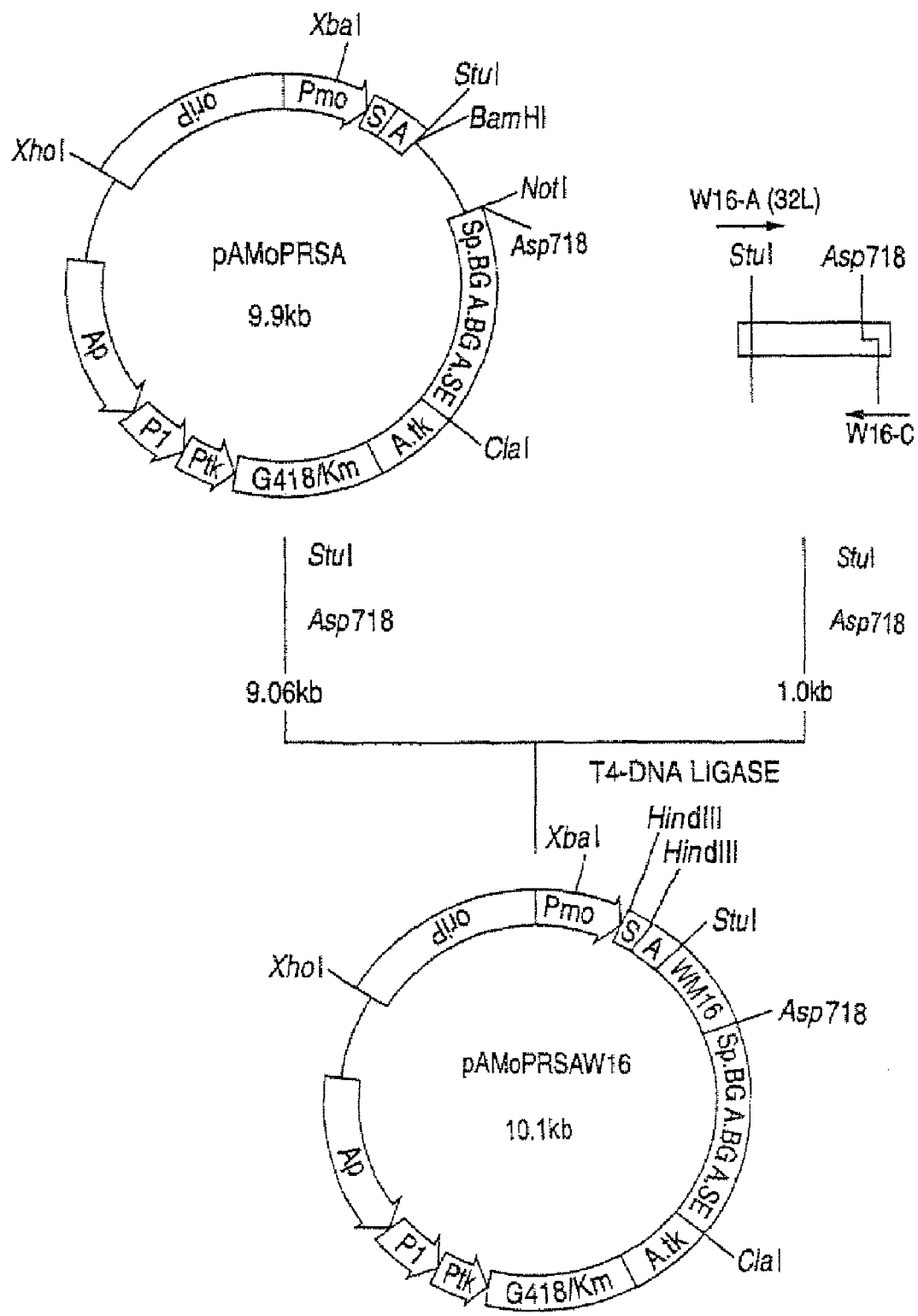
FIG. 26 shows a construction scheme for the plasmid pAMoPRSAW16.

(3) Secretory Production of α-2,3-sialyltransferase (WM17) in KJM-1 Cells (a) Construction of Plasmid pAMoPRSAW17-31F for Secretory Production of α-2,3-sialyltransferase (cf. FIG. 24)

Based on its primary sequence, the α-2,3-sialyltransferase (WM17) cloned is supposed to be composed of the cytoplasmid region (8 amino acid residues) on the N-terminal side, the subsequent membrane binding region (18 amino acid residues) and the C-terminal region (303 amino acid residues) having catalytic activity. Therefore, secretory production of α-2,3-sialyltransferase was attempted by eliminating the segment down to the membrane binding region of the α-2,3-sialyltransferase and instead adding the signal sequence of human granulocyte colony stimulating factor and the IgG binding region of *Staphylococcus aureus* protein A. The gene segment coding for the C-terminal region [from the 31st amino acid (phenylalanine) residue to the 329th amino acid (phenylalanine) residue in SEQ ID NO:6] having the catalytic activity of α-2,3-sialyltransferase was prepared by the PCR method and inserted into the secretory production vector pAMoPRSA constructed in Example 1, section 1-(5), As primers for PCR, the following two synthetic DNAs [W17-A (31F) (44 mer; SEQ ID NO:7) and W17-C (36 mer; SEQ ID NO:8)] were synthesized using an Applied Biosystems model 380A DNA synthesizer.

```
W17-A (31F) (44 mer)
5' CTCTCCGATATCTGTTTTATTTTCCCATCCCAGAGAAGAAGGAG 3'

W17-C (36 mer)
5' GATTAAGGTACCAGGTCAGAAGGACGTGAGGTTCTT 3'
```

Since W17-A (31F) is designed for introduction therein of an EcoRV site and W17-C for introduction therein of an Asp718 site, the DNA fragment amplified by PCR can be inserted, after cleavage with EcoRV and A 718, into pAMo-PRSA between the StuI and Asp718 sites. The PCR was carried out using Takara Shuzo's kit (GeneAmp™ DNA Amplification Reagent Kit with AmpliTaq™ Recombinant Taq DNA Polymerase). The reaction solution was prepared according to the kit method and, using Perkin Elmer Cetus' DNA Thermal Cycler (distributed by Takara Shuzo), the reaction steps (94° C., 1 minute; 55° C., 1 minute; and 72° C., 3 minutes) were repeated in a total of 30 cycles and then the reaction was further conducted at 72° C. for 7 minutes. The plasmid pUC119-WM17 (1 ng) constructed in (2)-(a) was used as a template. After completion of the reaction, chloroform extraction and ethanol precipitation were performed. The precipitate was dissolved in 30 µl of Y-100 buffer, 20 units of EcoRV and 20 units of Asp718 were added and the digestion reaction was carried out at 37° C. for 2 hours. The reaction mixture was subjected to agarose gel electrophoresis and a DNA fragment of about 0.91 kb was recovered.

Separately, 2 µg of pAMoPRSA was dissolved in 30 µl of Y-100 buffer, 20 units of StuI and 20 units of Asp718 were added and the digestion reaction was carried out at 37° C. for 2 hours. The reaction mixture was subjected to agarose gel electrophoresis and a DNA fragment of about 9.06 kb was recovered.

The EcoRV-Asp718 fragment (0.91 kb; 0.1 µg) derived from the PCR-amplified DNA as described above and the pAMoPRSA-derived StuI-Asp718 fragment (9.06 kb; 0.1 µg) obtained as described above were dissolved in 30 µl of T4 ligase buffer, 175 units of T4 DNA ligase was added and the ligation reaction was carried out at 12° C. for 16 hours.

The reaction mixture was used to transform *Escherichia coli* 101 by the method of Cohen et al. and an ampicillin-resistant strain was obtained. A plasmid was isolated from this transformant by a known method. This plasmid was named pAMoPRSAW17-31F and its structure was identified by digestion with restriction enzymes.

(b) Secretory Production of α-2,3-sialyltransferase (WM17) Using Namalwa KJM-1 Cells as a Host The plasmid pAMoPRSA (secretory production vector) obtained in Example 1, section 1-(5) and the plasmid pAMoPRSAW17-31F (plasmid for secretory production of α-2,3-sialyltransferase) constructed as described above were prepared using Qiagen's plasmid preparation kit (>plasmide<maxi kit; article number 41031). After precipitation with ethanol, each plasmid obtained was dissolved in TE buffer to a concentration of 1 µg/µl. Both the plasmids were then introduced into the Namalwa KJM-1 strain by electroporation [Miyaji et al.: Cytotechnology, 3, 133 (1990)]. After introduction of 4 µg of plasmid per $1.6 \times 10^6$ cells, the cells were suspended in 8 µl of RPMI1640-ITPSGF medium and cultivated in a $CO_2$ incubator at 37° C. for 24 hours. Then, G418 (Gibco) was added to a concentration of 0.5 mg/ml and cultivation was further continued for 7 to 14 days, whereby transformants were obtained. The transformants obtained were suspended in 30 µl of RPMI1640-ITPSGF medium containing 0.5 mg/ml of G418 to a concentration of $1 \times 10^5$ cells/ml and cultivated in a $CO_2$ incubator at 37° C. for 8 days. Then, cells were removed by centrifugation (160×g, 10 minutes) and each supernatant was recovered and again subjected to centrifugation (1,500×g, 10 minutes) and the supernatant was recovered. The culture supernatants thus obtained were stored at −80° C. until use.

Since the α-2,3-sialyltransferase encoded by the plasmid pAMoPRSAW17-31F is expressed and secreted as a protein fused with the IgG binding region of *Staphylococcus aureus* protein A, it can be readily purified using IgG Sepharose. Therefore, sodium azide was added to the culture supernatant obtained as mentioned above to a final concentration of 0.1%, then 100 µl of IgG Sepharose (Pharmacia) pretreated in accordance with the product manual was added and the mixture was stirred gently overnight at 4° C. Then, IgG Sepharose was recovered by centrifugation (160×g, 10 minutes) and washed with three 1 ml portions of RPMI1640-ITPSGF medium and 5 μl thereof was directly used for α-2,3-sialyltransferase activity assaying.

For activity determination, the reaction was carried out in 30 μl of an assay solution [0.1 M cacodylic acid-HCl (pH 6.5), 0.01 M $MnCl_2$, 0.45% Triton X-100, 0.1 mM substrate, above-described IgG Sepharose (5 μl), 5 mM CMP-sialic acid (with or without addition)] at 37° C. for 2 hours and then the activity was determined by identifying the product by high performance liquid chromatography (hereinafter referred to as "HPLC"). The following substrates were used: lacto-N-neotetraose (Galβ1-4GlcNAcβ1-3Galβ1-4Glc; hereinafter, "LNnT"), lacto-N-tetraose (Galβ1-3GlcNAcβ1-3Galβ1-4Glc; hereinafter, "LNT"), lacto-N-fucopentaose III (Galβ1-4(Fucα1-3)GlcNAcβ1-3-Galβ1-4Glc; hereinafter, "LNFP-III") and lacto-N-fucopentaose V(Galβ1-3GlcNAcβ1-3Galβ1-4(Fucα1-3)Glc; hereinafter, "LNFP-V") [all obtained from Oxford Glycosystems] each fluorescence-labeled with aminopyridine. The substrates were fluorescence-labeled according to the conventional method [Kondo et al.: Agricultural and Biological Chemistry, 54, 2169 (1990)]. For each IgG Sepharose, the reaction was carried out using the assay solution containing CMP-sialic acid (carbohydrate donor) and the assay solution without CMP-sialic acid and the peak appearing only with the CMP-sialic acid-containing assay solution as analyzed by HPLC was regarded as the product. After completion of the reaction, the assay solution was treated at 100° C. for 5 minutes and centrifuged at 10,000×g for 10 minutes and 10 μl of the supernatant obtained was subjected to HPLC. For HPLC, a TSK gel ODS-80 TM column 4.6 mm×30 cm; Tosoh Corp.) was used and elution was carried out with 0.02 M acetate buffer (pH 4.0) at an elution temperature of 50° C. at a flow rate of 1 ml/minute. The product was detected using a Shimadzu model RF-535T fluorescence HPLC monitor (excitation wavelength: 320 nm; emission wavelength: 400 nm). The product was judged as identified when the elution time was identical with that of the standard carbohydrate chain and when the substrate was regenerated upon sialidase treatment of the product. For quantitating the product, aminopyridylated lactose was used as the standard and the fluorescence intensities were compared.

When the IgG Sepharose used was the one derived from the culture supernatant of Namalwa cells harboring pAMo-PRSAW17-31F introduced therein, α-2,3-sialyltransferase activity was detected for all the carbohydrate chains used as substrates. The relative activities with the activity against LNnT taken as 100 were 42, 32 and 8 against LNT, LNFP-V and LNFP-III, respectively. In contrast, when the IgG Sepharose used was the one derived from the culture supernatant of Namalwa cells harboring the vector pAMoPRSA introduced therein, no such activity was detected for any of the carbohydrate chains used as substrates. The above results thus indicated that α-2,3-sialyltransferase can be produced and secreted in the culture supernatant as a protein fused to the IgG binding region of *Staphylococcus aureus* protein A and that the fused protein can be readily recovered and purified using IgG Sepharose.

3. Cloning of α-2,3-sialyltransferase (WM16) cDNA from WM266-4 Cells (Human Melanoma Cell Line) and Secretory Production of α-2,3-sialyltransferase (WM16)

(1) Cloning of α-2,3-sialyltransferase (WM16) cDNA from WM266-4 Cells, Namely Human Melanoma Cells (a) Isolation of mRNA from WM266-4 Cells, i.e. Human Melanoma Cells About 30 μg of mRNA was obtained from $1 \times 10^8$ WM266-4 cells (ATCC CRL1676) using Invitrogen's mRNA extracation kit Fast Track (article number K1593-02). The reagents and procedure actually employed were as described in the manual attached to the kit.

(b) Construction of cDNA Library

Based on 8 μg of the mRNA obtained in the above, double-stranded cDNA synthesis was carried out using Gibco BRL's cDNA synthesis kit (cDNA Synthesis System), with oligo dT as the primer. On that occasion, another reverse transcriptase of the same company (Super Script™ RNase H⁻ reverse transcriptase) was used as the reverse transcriptase in lieu of the reverse transcriptase belonging to the kit (Moloney murine leukemia virus (M-MLV) reverse transcriptase). Then, the double-stranded cDNA synthesized and the SfiI linker (4 μg of the 11 mer and 2.9 μg of the 8 mer) prepared in the same manner as in Example 1, section 2-(2) were dissolved in 45 μl of T4 ligase buffer, 1,050 units of T4 DNA ligase was added and the ligation reaction was carried out at 16° C. for 16 hours. The reaction mixture was subjected to agarose gel electrophoresis and cDNA fragments not less than about 1.2 kb in size were recovered.

Separately, 24 μg of the expression cloning vector pAMoPRC3Sc obtained in Example 1, section 1-(5) was dissolved in 590 μl of Y-50 buffer, 80 units of SfiI was added and the digestion reaction was carried out at 37° C. for 16 hours. For confirming completion of the cleavage, 5 μl of the reaction mixture was subjected to agarose gel electrophoresis. Thereafter, for reducing the proportion of clones free of cDNA, 40 units of BamHI was added and the digestion reaction was further carried out at 37° C. for 2 hours. The reaction mixture was subjected to agarose gel electrophoresis and a DNA fragment of about 8.8 kb was recovered.

The pAMoPRC3Sc-derived SfiI fragment (8.8 kb; 2 μg) obtained as described above and the cDNA purified in the above manner were dissolved in 250 μl of T4 ligase buffer, 2,000 units of T4 DNA ligase was added and the ligation reaction was carried out at 16° C. for 16 hours. Then, 5 μg of transfer RNA (tRNA) was added and, after precipitation with ethanol, the precipitate was dissolved in 20 μl of TE buffer. The reaction mixture was used to transform *Escherichia coli* LE392 by electroporation and about $2.6 \times 10^5$ ampicillin-resistant strains were obtained.

(c) Cloning of α-2,3-sialyltransferase (WM16) cDNA

The about $2.6 \times 10^5$ ampicillin-resistant strains obtained in the above were mixed and plasmid preparation was performed using Qiagen's plasmid preparation kit (>plasmid<maxi kit; article number 41031). The plasmid obtained was precipitated with ethanol and dissolved in TE buffer to a concentration of 1 μg/μl.

The above-described plasmid was introduced into the KJM-1 strain by electroporation. After introduction of 4 μg of plasmid per $1.6 \times 10^6$ cells, the cells were suspended in 8 μl of RPMI1640-ITPSGF medium and cultured in a $CO_2$ incubator at 37° C. for 24 hours. Then, G418 (Gibco) was added to a concentration of 0.5 mg/ml and cultivation was further continued for 7 days. Transformants were thus obtained. The transformants obtained were suspended in RPMI1640-ITPSGF medium containing *Ricinus communis* lectin 120 (50 ng/ml) to a concentration of $5 \times 10^4$ cells/ml and the suspension was distributed in 200 μl portions into wells of 96-well microtiter plates.

Cultivation was conducted in a $CO_2$ incubator at 37° C. for 4 weeks and a strain resistant to *Ricinus communis* lectin 120 was obtained. The resistant strain was cultured and then a plasmid was recovered from about $5 \times 10^6$ cells thereof by the H art method. The plasmid recovered was introduced into *Escherichia coli* LE392 by electroporation and an ampicillin-resistant strain was obtained. A plasmid was prepared from that transformant strain using Qiagen's plasmid preparation kit and its structure was examined by cleaving with various restriction enzymes. It was revealed that it contains a cDNA of about 2.2 kb. The plasmid containing this cDNA was named pAMoPRWM16 and again introduced into the KJM-1 strain by the same method as described above, whereupon the strain developed resistance against *Ricinus communis* lectin 120. Therefore, this cDNA is apparently the DNA coding for α-2,3-sialyltransferase.

(2) Base Sequence Determination of α-2,3-sialyltransferase (WM16) cDNA (a) Insertion of α-2,3-sialyltransferase (WM16) cDNA into pUC119 (cf. FIG. 25)

pAMoPRWM16 (2 μg) obtained as described above was dissolved in 50 μl of Y-100 buffer, 30 units of EcoRV and 30 units of Asp718 (Boehringer Mannheim) were added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes for converting the 5' cohesive end resulting from Asp718 digestion to a blunt end. The reaction mixture was subjected to agarose gel electrophoresis and a DNA fragment of about 2.3 kb was recovered.

Separately, 1 Mg of pUC119 [Messing et al.: Methods in Enzymology, 153, 3 (1987)] was dissolved in 30 μl of Y-100 buffer, 20 units of HincII was added and the digestion reaction was carried out at 37° C. for 2 hours. Then, 30 μl of 1 M Tris-HCl (pH 8.0) and 1 unit of *Escherichia coli*-derived alkaline phosphatase (Takara Shuzo) were added and the dephosphorylation reaction was carried out at 37° C. for 2 hours. After precipitation with ethanol, the precipitate was dissolved in 30 μl of TE buffer and subjected to agarose gel electrophoresis, and a DNA fragment of about 3.16 kb was recovered.

The pAMoPRWM16-derived EcoRV-Asp718 (blunt end) fragment (2.3 kb; 0.05 μg) and pUC119-derived HincII fragment (3.16 kb; 0.05 μg) obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and ampicillin-resistant strains were obtained. Plasmid isolation was performed from the transformant strains by a known method. Two plasmids differing in the direction of the pAMoPRWM16-derived EcoRV-A 718 (blunt end) fragment were isolated. The respective plasmids were named pUC119-WM16 and pUC119-WM16R and their structures were identified by digestion with restriction enzymes.

(b) Construction of Deletion-Mutated Plasmids for Sequencing pUC119-WM16 (2 μg) and pUC119-WM16R (2 μg) obtained as described above were dissolved in 30 μl of Y-0 buffer, 50 units of KpnI was added and the digestion reaction was carried out at 37° C. for 16 hours. Then, NaCl was added to an NaCl concentration of 100 mM, 40 units of NotI was added and the digestion reaction was further carried out at 37° C. for 2 hours. After precipitation with ethanol, the precipitate was dissolved in 100 μl of exonuclease III buffer (attached to Takara Shuzo's deletion kit for kilosequencing). After precipitation with ethanol, the precipitate was dissolved in 100 μl of exonuclease III buffer.

Starting from the pUC119WM16-derived KpnI-BamHI fragment and pUC119-WM16R-derived KpnI-BamHI fragment obtained as described above, scores of deletion-mutated plasmids were produced for each fragment using Takara Shuzo's deletion kit for kilosequencing. The reagents and procedure actually employed were as described in the manual attached to the kit.

The deletion-mutated plasmids obtained in the above were sequenced using Applied Biosystems' sequencing kit (Taq DyeDeoxy™ Terminator Cycle Sequencing Kit; article number 401113). The base sequence thus determined is shown as SEQ ID NO:9. As a result, it was revealed that the *Ricinus communis* lectin 120 resistance gene (WM16) codes for a protein composed of 375 amino acid residues. Based on the amino acid sequence, it was further revealed that this protein has a structure common to glycosyltransterases. Thus, it appears that it comprises the N-terminal cytoplasmic region (8 amino acid residues), the subsequent membrane binding region (20 amino acid residues) and the C-terminal region (347 amino acid residues) showing catalytic activity.

(3) Secretory Production of α-2,3-sialyltransferase (WM16) in KJM-1 Cells (a) Construction of Plasmid pAMoPRSAW16 for Secretory Production of α-2,3-sialyltransferase (cf. FIG. 26)

Based on its primary sequence, the α-2,3-sialyl transferase (WM16) cloned is composed of the N-terminal cytoplasmic region (8 amino acid residues), the subsequent membrane binding region (20 amino acid residues) and the C-terminal region (347 amino acid residues) showing catalytic activity. Therefore, secretory production of α-2,3-sialyltransferase was attempted by eliminating the segment down to the membrane binding region of α-2,3-sialyltransferase and instead adding the signal sequence of human granulocyte colony stimulating factor and the IgG binding region of *Staphylococcus aureus* protein A. The gene segment coding for the C-terminal region [from the 32nd amino acid (serine) residue to the 375th amino acid (isoleucine) residue in SEQ ID NO:9] having the catalytic activity of α-2,3-sialyltransferase was prepared by the PCR method and inserted into the secretory expression vector pAMoPRSA constructed in Example 1, section 1-(5).

As primers for PCR, the following two synthetic DNAs [W16-A (32L) (38 mer; SEQ ID NO:10) and W16-C (37 mer; SEQ ID NO:11)] were synthesized using an Applied Biosystems model 380A DNA synthesizer.

```
W16-A (32L) (38 mer)
5'-CTCTGTAGGCCTTACTCCAGTGGGAGGAGGACTCCAAT-3'

W16-C (37 mer)
5'-GACTCAGGTACCACTCAGATGCCACTGCTTAGATCAG-3'
```

Since W16-A(32L) is designed for introduction therein of an StuI site and W16-C for introduction therein of an Asp718 site, the DNA fragment amplified by PCR can be inserted, after cleavage with StuI and Asp718, into pAMoPRSA between the StuI and Asp718 sites. The PCR was carried out using Takara Shuzo's kit (GeneAmp™ DNA Amplification Reagent Kit with AmpliTaq™ Recombinant Tag DNA Polymerase). The reaction solution was prepared according to the manual attached to the kit and, using Perkin Elmer Cetus' DNA Thermal Cycler (distributed by Takara Shuzo), the reaction steps (94° C., 1 minute; 55° C., 1 minute; and 72° C., 3 minutes) were repeated in a total of 30 cycles and then the reaction was further conducted at 72° C. for 7 minutes. The plasmid pUC119-WM16 (1 ng) was used as a template. After completion of the reaction, chloroform extraction and ethanol precipitation were performed and the precipitate was dissolved in 30 μl of Y-100 buffer, 20 units of StuI and 20 units of Asp718 were added and the digestion reaction was carried out at 37° C. for 2 hours. The reaction mixture was subjected to agarose gel electrophoresis and a DNA fragment of about 1.0 kb was recovered. Separately, 2 μg of pAMoPRSA was dissolved in 30 μl of Y-100 buffer, 20 units of StuI and 20 units of Asp718 were added and the digestion reaction was carried out at 37° C. for 2 hours. The reaction mixture was subjected to agarose gel electrophoresis and a DNA fragment of about 9.06 kb was recovered.

The StuI-A718 fragment (1.0 kb; 0.1 μg) derived from the DNA amplified by PCR as obtained in the above and the pAMoPRSA-derived StuI-Asp718 fragment (9.06 kb; 0.1 μg) obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant strain by a known method. This plasmid was named pAMoPRSAW16 and its structure was identified by digestion with restriction enzymes.

(b) Secretory Production of α-2,3-sialyltransferase (WM16) Using Namalwa KJM-1 Cells as a Host The plasmids pAMoPRSA (secretory production vector) and pAMoPRSAW16 (plasmid for secretory production of α-2,3-sialyltransferase) obtained as described above were prepared using Qiagen's plasmid preparation kit (>plasmid<maxi kit; article number 41031). The plasmids prepared were precipitated with ethanol and then dissolved in TE buffer to a concentration of 1 μg/μl. Then, both the plasmids were introduced into the Namalwa KJM-1 strain by electroporation [Miyaji et al.: Cytotechnology, 3, 133 (1990)]. After introduction of 4 μg of plasmid per $1.6 \times 10^6$ cells, the cells were suspended in 8 ml of RPMI1640-ITPSGP medium and cultured in a $CO_2$ incubator at 37° C. for 24 hours. Then, G418 (Gibco) was added to a concentration of 0.5 mg/ml and cultivation was continued for 7 days. Thereafter, 22 ml of RPMI1640-ITPSGF medium (containing 0.5 mg/ml of G418) was added and cultivation was further continued for 5 days. Transformants were thus obtained. The transformants obtained were suspended in 30 ml of RPMI1640-ITPSGF medium containing 0.5 mg/ml of G418 to a concentration of $5 \times 10^4$ cells/ml and cultivated in a $CO_2$ incubator at 37° C. for 8 days. Then, cells were removed by centrifugation (160×g, 10 minutes) and each supernatant was recovered and again centrifuged (1,500×g, 10 minutes) and the supernatant was recovered. The culture supernatants thus obtained were stored at −80° C. until use.

Since the protein encoded by the plasmid pAMo-PRSAW16 is produced and secreted as a protein fused to the IgG binding region of protein A, it can be readily purified using IgG Sepharose. Therefore, sodium azide was added to each supernatant obtained in the above to a final concentration of 0.1%, 100 μl of IgG Sepharose (Pharmacia) pretreated in accordance with the manual attached thereto and the mixture was stirred gently overnight at 4° C. Then, IgG Sepharose was recovered by centrifugation (160×g, 10 minutes) and washed with three 1-ml portions of a buffer comprising 50 mM Tris-HCl (pH 7.6), 150 mM sodium chloride and 0.05% Tween 20. Then, the protein adsorbed on IgG Sepharose was eluted with 100 μl of 0.5 M acetic acid (adjusted to pH 3.4 with ammonium acetate) and IgG Sepharose was removed by centrifugation (160×g, 10 minutes). The eluate was adjusted to pH 7.0 by adding 2 M Tris-HCl (pH 8.0) and water was added to make a final volume of 1 ml. Using 5 μl of the eluate prepared in that manner, its sialyltransferase activity was determined.

For activity determination, the reaction was carried out in 30 μl of an assay solution [0.1 M cacodylic acid-hydrochloric acid (pH 6.5), 0.01 M manganese chloride, 0.45% Triton X-100, 0.1 mM substrate, eluate described above (5 μl), 5 mM CMP-sialic acid (with or without addition)] at 37° C. for 30 minutes and then product identification was performed by HPLC. The substrates used were LNnT, LNT and LNFP-V (all available from Oxford Glyco-systems) each fluorescence-labeled with aminopyridine. The substrates were fluorescence-labeled by the conventional method [Kondo et al.: Agricultural and Biological Chemistry, 54, 2169 (1990)]. For each IgG Sepharose, the reaction was carried out using the assay solution containing CMP-sialic acid (carbohydrate donor) and the assay solution free of CMP-sialic acid and the peak appearing only with the CMP-sialic acid-containing assay solution as analyzed by HPLC was regarded as the product. After completion of the reaction, the assay solution was treated at 100° C. for 5 minutes and centrifuged at 10,000×g for 10 minutes and a 10 μl portion of the supernatant obtained was subjected to HPLC. For HPLC, a TSK gel ODS-80 TM column (4.6 mm×30 cm; Tosoh Corp.) was used and elution was carried out with 0.02 M acetate buffer (pH 4.0) at an elution temperature of 50° C. and a flow rate of 1 ml/minute. For product detection, a Shimadzu model RF-535T fluorescence HPLC monitor was used (excitation wavelength: 320 nm; emission wavelength: 400 nm). The product was judged as identified when the elution time was identical with that of the standard carbohydrate chain and when the substrate was regenerated upon sialidase treatment of the product. For quantitating the product, aminopyridylated lactose was used as the standard and fluorescence intensity comparison was made.

When the IgG Sepharose used was the one derived from the culture supernatant of Namalwa cells harboring pAMo-PRSAW16 introduced therein, α-2,3-sialyltransferase activity was detected for all the carbohydrate chains used as substrates. The relative activities with the activity against LNT taken as 100 were 98 and 4 against LNFP-V and LNnT, respectively. On the contrary, when the IgG Sepharose used was the one derived from the culture supernatant of Namalwa cells harboring the vector pAMoPRSA introduced therein, no such activity was detected for any of the carbohydrate chains used as substrates.

The above results indicated that α-2,3-sialyltransferase can be produced and secreted into the culture supernatant in the form of a protein fused to the IgG binding region of *Staphylococcus aureus* protein A and that the secretion product can be readily recovered and purified using IgG Sepharose.

4. Cloning of α-1,3-fucosyltransferase (Fuc-TVI) cDNA from SW116 Cells (Human Rectal Cancer Cell Line) and Construction of Fuc-TVI Expression Plasmid (1) Cloning of α-1,3-fucosyltransferase (Fuc-TVI) cDNA from SW1116 Cells (Human Rectal Cancer Cell Line)

(a) Testing of KJM-1 Strain Harboring Expression Vector pAMoPRC3Sc Introduced Therein for Resistance Against *Maacia amurensis* Lectin I The KJM-1 strain harboring the expression vector pAMoPRC3Sc obtained in Example 1, section 1-(15) was cultured in the presence of *Maacia amurensis* lectin I (hereinafter referred to as "MAL-I"; product of Vector) in various concentrations and tested for resistance against MAL-I. Thus, cells of the KJM-1 strain were suspended in RPMI1640-ITPSGF medium to a concentration of $5 \times 10^4$ cells/ml and the suspension was distributed in 200 μl portion into wells of a 96-well microtiter plate. Thereto were added various concentrations of MAL-I in 1/100 volume portions and cultivation was performed in a $CO_2$ incubator at 37° C. for 3 weeks. As a result, the minimum concentration of MAL-I as required for complete inhibition of the growth of the KJM-1 strain was found to be 10 mg/ml. With $4 \times 10^6$ KJM-1 strains tested, any spontaneous appearance of MALI-resistant strains was not observed.

(b) Isolation of mRNA from SW1116 Cells

About 30 μg of mRNA was obtained from $1 \times 10^8$ SW1116 cells (ATCC CCL223) using Invitrogen's mRNA extraction kit Fast Tract (article number K1593-02). The reagents and procedure actually employed were those described in the manual attached to the kit.

(c) Construction of cDNA Library

Using 8 μg of the mRNA obtained in the above manner, a cDNA library was constructed in the same manner as in Example 1, section 2-(2) and about $4.8 \times 10^5$ ampicillin-resistant strains were obtaiend.

(d) Cloning of α-1,3-fucosyltransferase (Fuc-TVI) cDNA

The about $4.8 \times 10^5$ ampicillin-resistant strains (cDNA library) obtained as described above were mixed and plasmid preparation was performed using Qiagen's plasmid preparation kit (>plasmid<maxi kit; article number 41031). The plasmid obtained was precipitated with ethanol and dissolved in TE buffer to a concentration of 1 μg/μl.

The above-described plasmid was introduced into KJM-1 strain by electroporation. After introduction of 4 μg of plasmid per $1.6 \times 10^6$ cells, the cells were suspended in 8 ml of RPMI1640-ITPSGF medium and cultured in a $CO_2$ incubator at 37° C. for 24 hours. Then, G418 (Gibco) was added to a concentration of 0.5 mg/ml and cultivation was further continued for 7 days, whereby transformants were obtained. The transformants obtained were suspended in RPMI1640-ITPSGF medium containing MAL-I (10 μg/μl) and G418 (0.5 mg/ml) to a concentration of $5 \times 10^4$ cells/ml and the suspension was distributed in 200 μl portions into wells of 96-well microtiter plates.

After 3 weeks of incubation in a $CO_2$ incubator at 37° C., a MAL-I-resistant strain was obtained. After incubation of the resistant strain, a plasmid was recovered from about $5 \times 10^6$ cells thereof by the Hart method. The plasmid recovered was introduced into *Escherichia coli* LE392 by electroporation and an ampicillin-resistant strain was obtained. Plasmid preparation was performed from that transformant using Qiagen's plasmid preparation kit and the structure of the plasmid was examined by cleaving with various restriction enzymes, whereupon it was found that the plasmid contains a cDNA of about 2.1 kb. The plasmid containing this cDNA was named pAMoPRMAL4 and again introduced into the KJM-1 strain by the same method as described above, whereupon the strain developed resistance against MAL-I, proving that said cDNA is the gene (MAL-I resistance gene) providing the KJM-1 strain with resistance against MAL-I.

Figure 27:
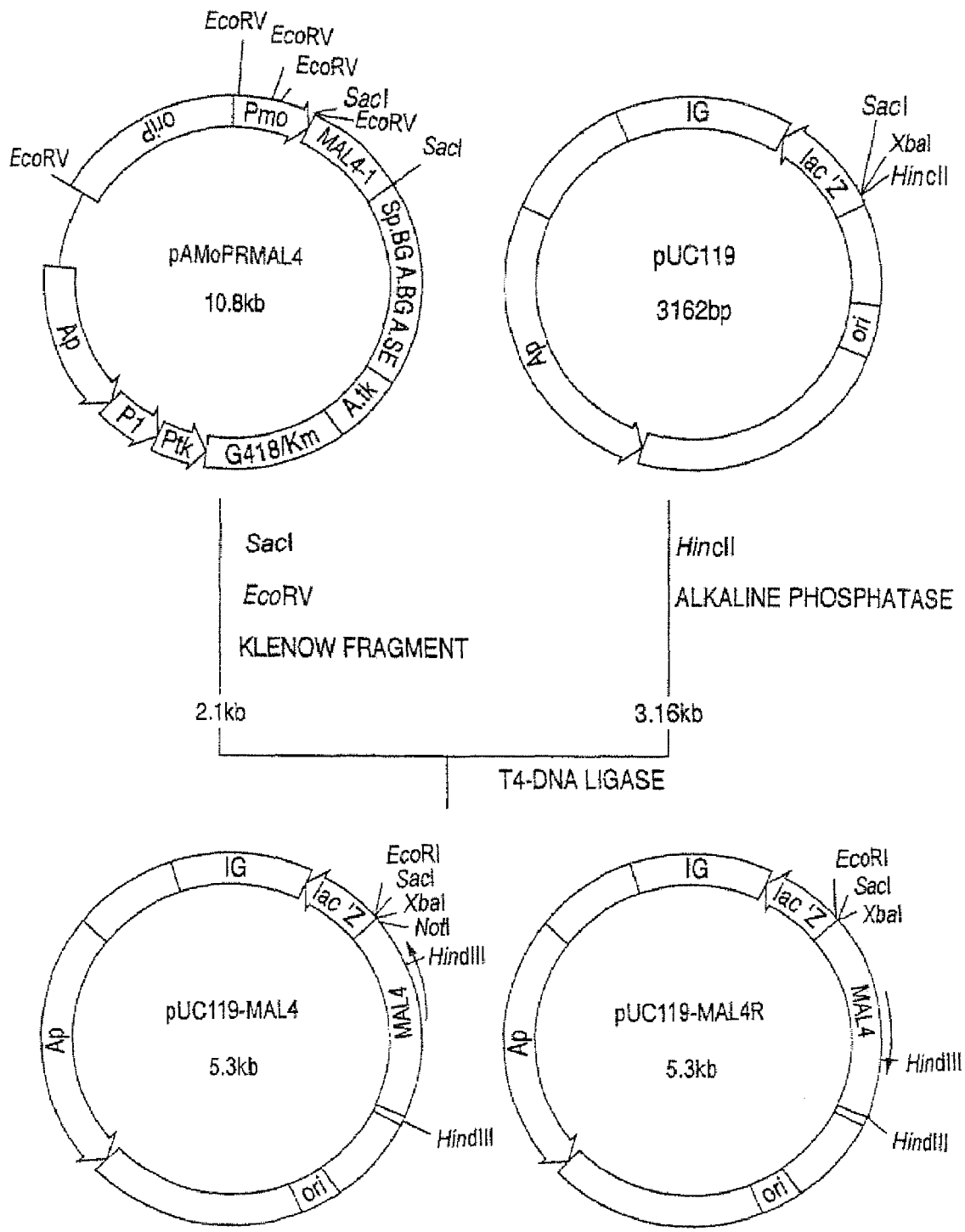
FIG. 27 shows a construction scheme for the plasmids pUC119-MAL4 and pUC119-MAL4R.

(2) Base Sequence Determination of α-1,3-fucosyltransferase (Fuc-TVI) cDNA (a) Insertion of α-1,3-fucosyltransferase (Fuc-TVI) cDNA into pUC119 (cf. FIG. 27)

pALMoPRMAL4 (2 μg) was dissolved in 50 μl of Y-0 buffer, 30 units of SacI was added and the digestion reaction was carried out at 37° C. for 2 hours. Then, NaCl was added to an NaCl concentration of 150 mM, 20 units of EcoRV was added and the digestion reaction was further carried out at 37° C. for 2 hours. After precipitation with ethanol, the precipitate was dissolved in 30 μl of DNA polymerase I buffer, 6 units of *Escherichia coli*-derived DNA polymerase I Klenow fragment and the reaction was carried out at 37° C. for 60 minutes to convert the 3' cohesive end formed upon SacI digestion to a blunt end. The reaction mixture was subjected to agarose gel electrophoresis and a DNA fragment of about 2.1 kb was recovered.

Separately, pUC119 (1 μg) was dissolved in 30 μl of Y-100 buffer, 20 units of HincII was added and the digestion reaction was carried out at 37° C. for 2 hours. Then, 30 μl of 1 M Tris-HCl (pH 8.0) and 1 unit of *Escherichia coli*-derived alkaline phosphatase (Takara Shuzo) were added and the dephosphorylation reaction was carried out at 37° C. for 2 hours. After precipitation with ethanol, the precipitate was dissolved in 30 μl of TE buffer and subjected to agarose gel electron phoresis and a DNA fragment of about 3.16 kb was recovered.

The pAMoPRMAL4-derived SacI (blunt end)-EcoRV fragment (2.1 kb; 0.05 μg) and pUC119-derived HincII fragment (3.16 kb; 0.05 μg) obtained as mentioned above were dissolved in 30 μl of T4 ligase buffer, 175 units of T4 DNA ligase was added and the ligation reaction was carried out at 12° C. for 16 hours.

The reaction mixture was used to transform *Escherichia coli* JM105 by the method of Cohen et al. and ampicillin-resistant strains were obtained. Plasmids were isolated from these transformant strains by a known method and the structures thereof were identified by digestion with restriction enzymes. Two plasmids differing in the direction of the pAMoPRMAL4-derived SacI (blunt end)-EcoRV fragment inserted into pUC119 were isolated. The plasmids were named pUC119-MAL4 and pUC119-MAL4R, respectively.

(b) Construction of Deletion-Mutated Plasmids for Sequencing pUC119-MAL4 (2 μg) and pUC119MAL4R (2 μg) were respectively dissolved in 30 μl of Y-0 buffer, 50 units of SacI was added and the digestion reaction was carried out at 37° C. for 16 hours. Then, NaCl was added to an NaCl concentration of 100 mM, 40 units of XbaI was added and the digestion reaction was further carried out at 37° C. for 2 hours. After precipitation with ethanol, each precipitate was dissolved in 100 μl of exonuclease III buffer (attached to Takara Shuzo's deletion kit for kilosequencing).

Starting from the pUC119-MAL4-derived SacI-XbaI fragment and pUC119-MAL4R-derived SacI-XbaI fragment obtained in the above manner, a total of 18 deletion-mutated plasmids were prepared using Takara Shuzo's deletion kit for kilosequencing. The reagents and procedure actually employed were as described in the manual attached to the kit. The base sequences of the deletion plasmids thus obtained were determined using Applied Biosystems' sequencing kit (Taq DyeDeoxy™ Terminator Cycle Sequencing Kit; article number 401113). As a result, it was revealed that the MAL-I resistance gene codes for a known α-1,3-fucosyltransferase (Fuc-TVI) but not for the α-1,3-fucosyltransferase (TH21) of the present invention.

Figure 28:
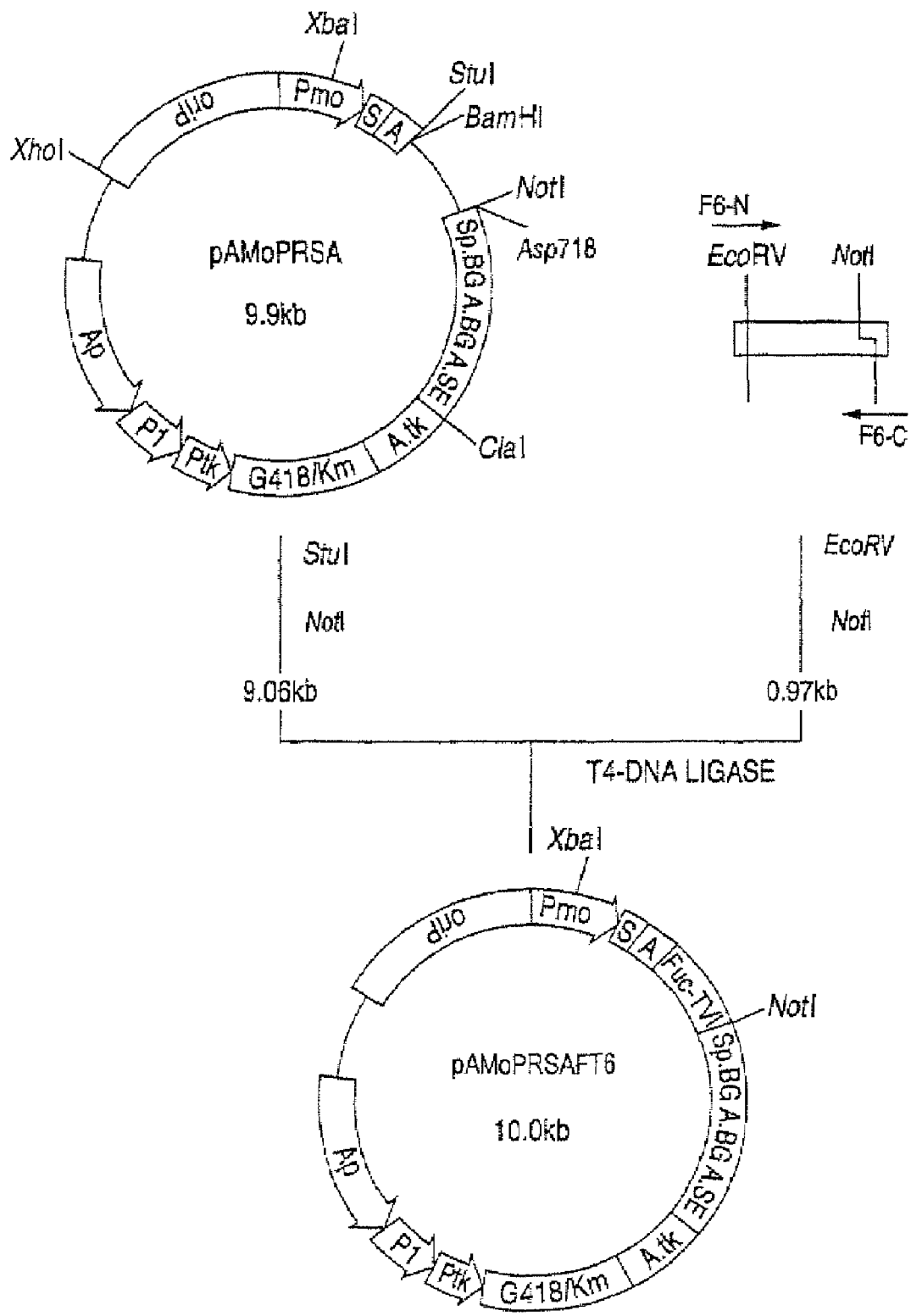
FIG. 28 shows a construction scheme for the plasmid pAMoPRSAFT6.

(3) Secretory Production of Fuc-TVI in KJM-1 Cells (a) Construction of Plasmid pAMoPRSAFT6 for Secretory Expression of Fuc-TVI (cf. FIG. 28)

Based on its primary sequence, the thus-cloned Fuc-TVI is supposed to be composed of the N-terminal cyloplasmic region (14 amino acid residues), the subsequent membrane binding region (20 amino acid residues) and the C-terminal region (325 amino acid residues) having catalytic activity. Therefore, an attempt was made to cause secretory expression of Fuc-TVI by deleting the segment down to the membrane binding region of Fuc-TVI and instead adding the signal sequence of human granulocyte colony stimulating factor and the IgG binding region of *Staphylococcus aureus* protein A. The gene segment coding for the C-terminal region [from the 40th amino acid (aspartic acid) residue to the 359th amino acid (threonine) residue] having the catalytic activity of Fuc-TVI was prepared by the PCR method and inserted into the secretory expression vector pAMoPRSA constructed in Example 1, section 1-(5).

The following two synthetic DNAs [F6-N (34 mer; SEQ ID NO:12) and F6-C (37 mer; SEQ ID NO:13)] were synthesized as primers for PCR using an Applied Biosystems model 380A DNA synthesizer

```
F6-N (34 mer)
5'-CTCTCGGATATCCCACTGTGTACCCTAATGGGTC-3'

F6-C (37 mer)
5'-GTAGACGCGGCCGCTCAGGTGAACCAAGCCGCTATG-3'
```

Since F6-N (34 mer) is designed for introduction therein of an EcoRV site and F6-C (37 mer) for introduction therein of an NotI site, the DNA fragment amplified by PCR can be inserted, after cleavage with EcoRV and NotI, into pAMoPRSA between the StuI and NotI sites. The PCR was carried out using Takara Shuzo's kit (GeneAmp™ DNA Amplification Reagent Kit with AmpliTaq™ Recombinant Taq DNA Polymerase) The reaction solution was prepared according to the manual attached to the kit and, using Perkin Elmer Cetus' DNA Thermal Cycler (distributed by Takara Shuzo), the reaction steps (94° C., 1 minute; 65° C., 1 minute; and 72° C. 3 minutes) were repeated in a total of 20 cycles and then the reaction was further conducted at 72° C. for 7 minutes The plasmid pUC119-MAL4 (70 ng) was used as a template. After completion of the reaction, chloroform extraction and ethanol precipitation were performed and the precipitate was dissolved in 30 μl of Y-80 buffer, 20 units of EcoRV and 20 units of NotI were added and the digestion reaction was carried out at 37° C. for 2 hours. The reaction mixture was subjected to agarose gel electrophoresis and a DNA fragment of about 0.97 kb was recovered.

Separately, 2 μg of pAMoPRSA was dissolved in 30 μl of Y-100 buffer, 20 units of StuI was added and the digestion reaction was carried out at 37° C. for 2 hours. Then, NaCl was added to a concentration of 150 mM, 20 units of NotI was added and the digestion reaction was carried out at 37° C. for 2 hours. The reaction mixture was subjected to agarose gel lectrophoresis and a DNA fragment of about 9.06 kb was recovered.

The EcoRV-NotI fragment (0.97 kb; 0.1 μg) derived from the PCR-amplified DNA and the pAMoPRSA-derived StuI-NotI fragment (9.06 kb; 0.1 μg), obtained in the above manner, were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant strain by the known method. This plasmid was named pAMoPRSAFT6 and its structure was identified by digestion with restriction enzymes.

Figure 29:
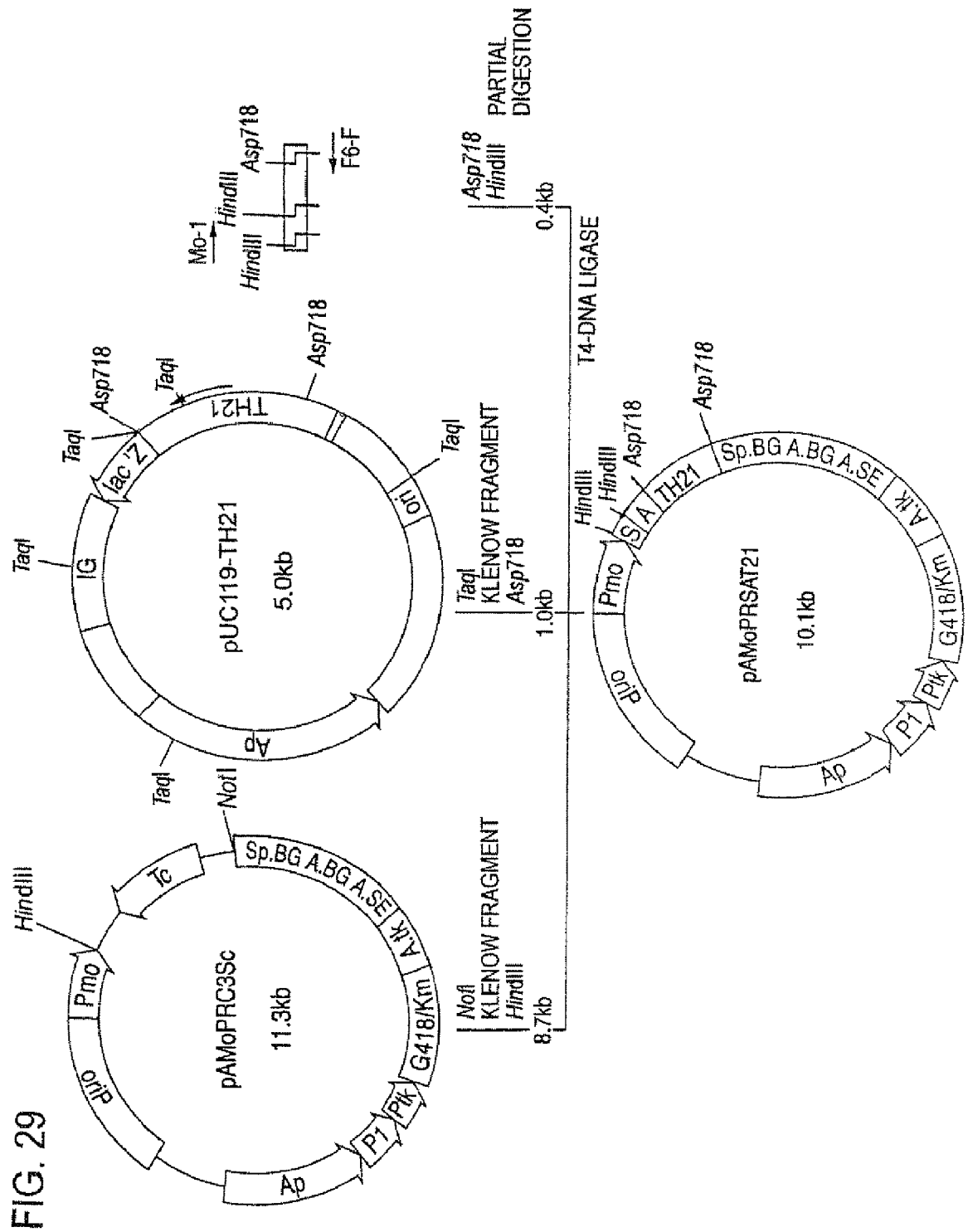
FIG. 29 shows a construction scheme for the plasmid pAMoPRSAT21.
Figure 30:
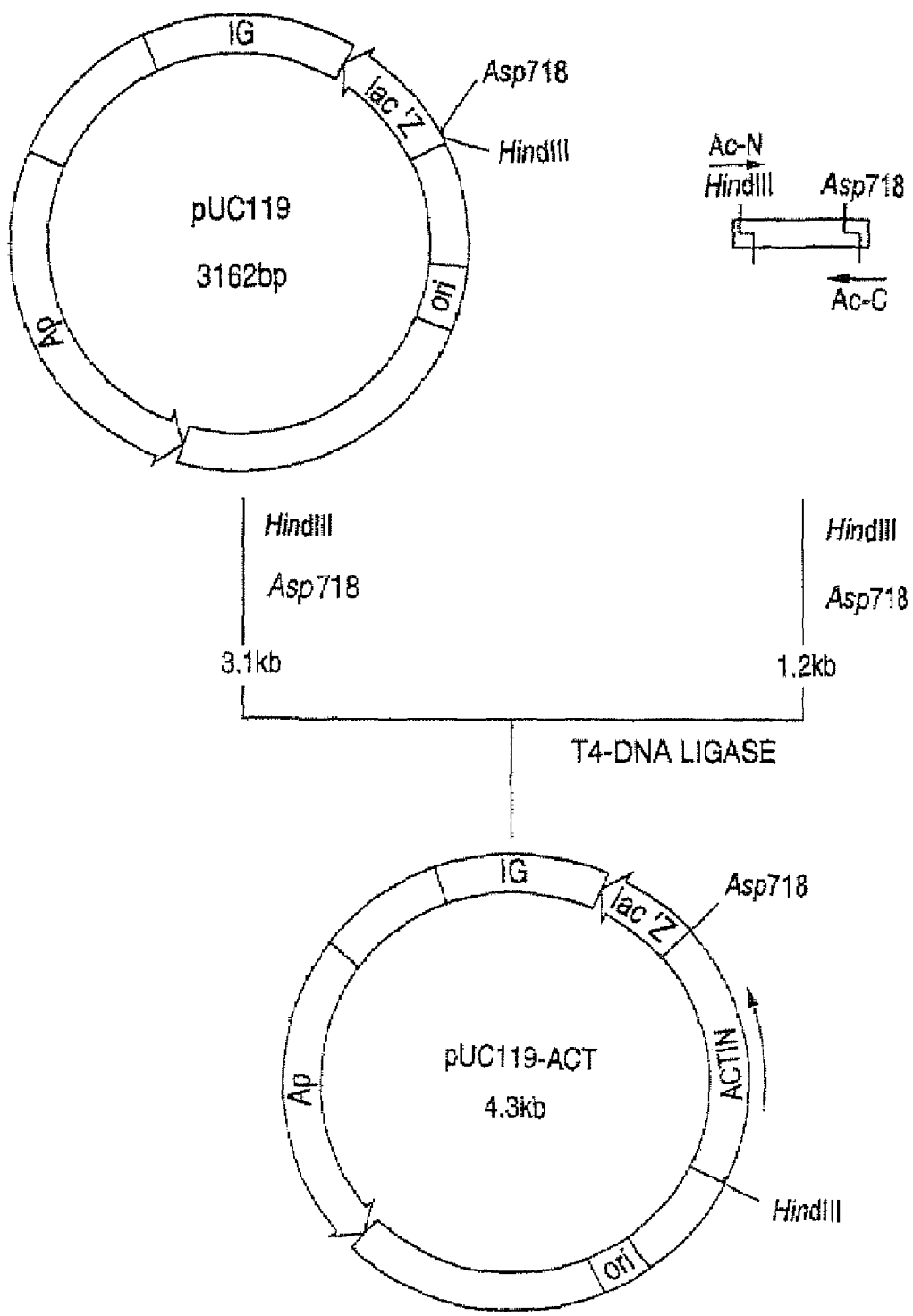
FIG. 30 shows a construction scheme for the plasmid pUC119-ACT.
Figure 31:
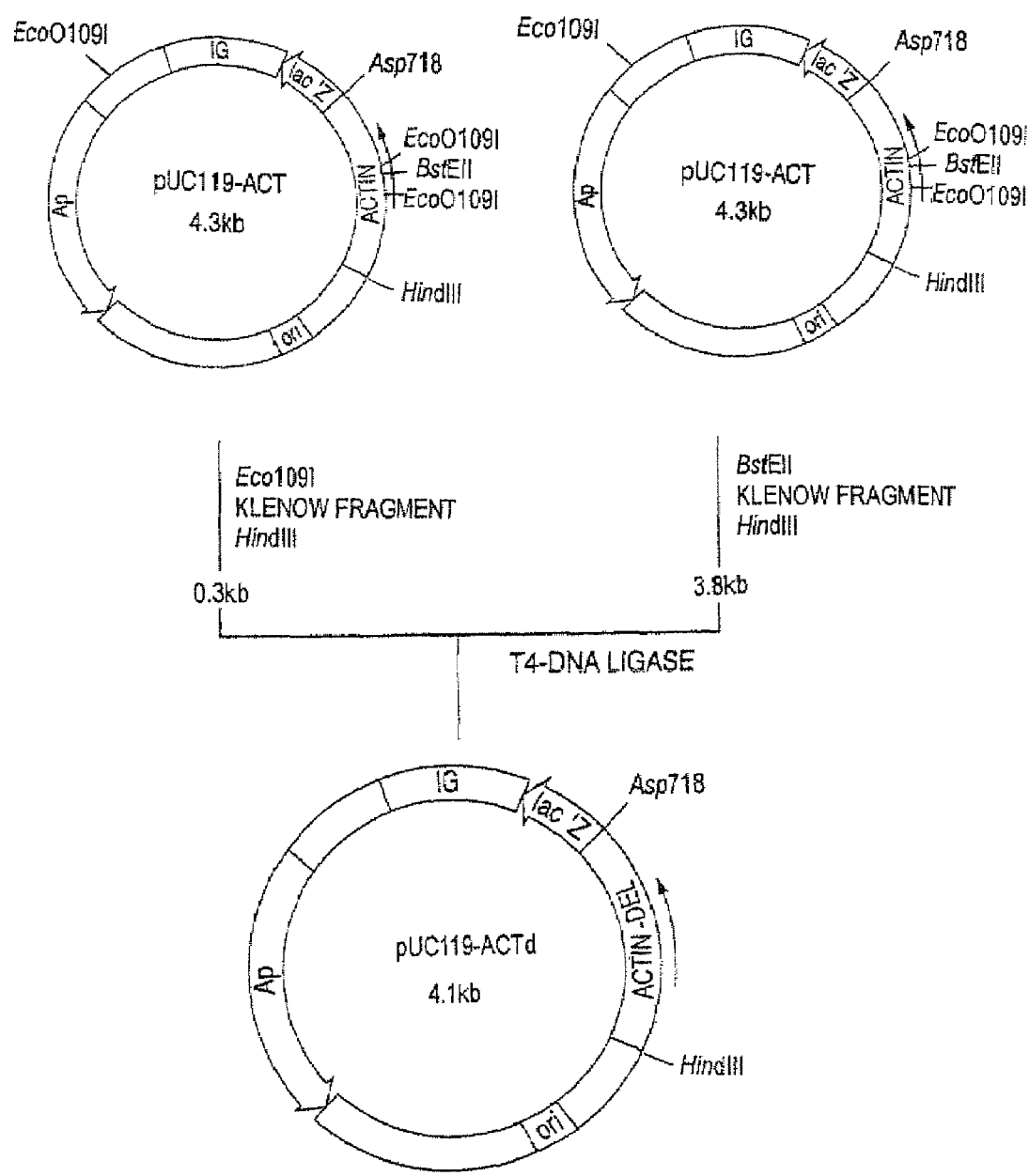
FIG. 31 shows a construction scheme for the plasmid pUC119-ACTd.
Figure 32:
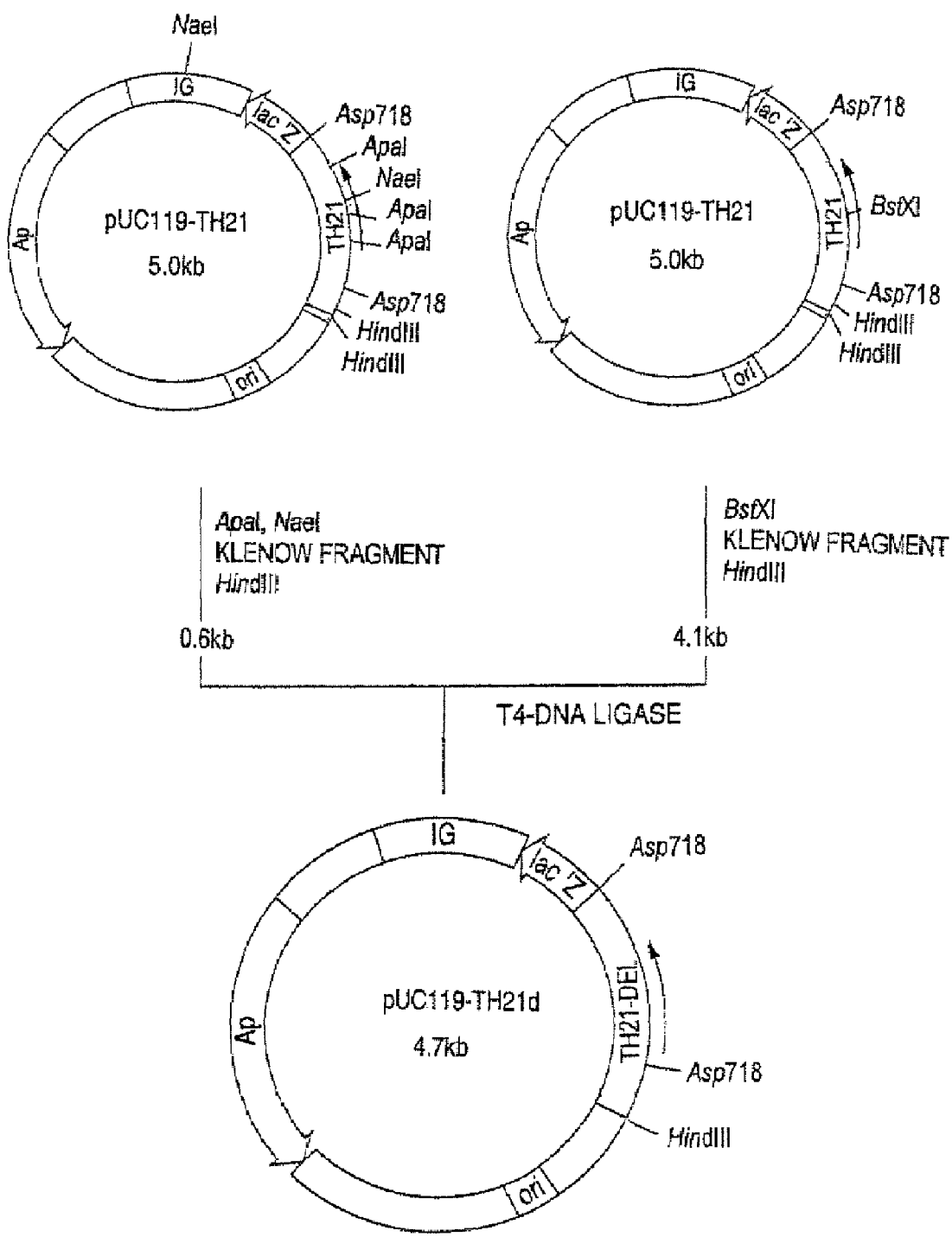
FIG. 32 shows a construction scheme for the plasmid pUC119-TH21d.

5. Secretory Production of α-1,3-fucosyltransferase (TH21) in KJM-1 Cells (1) Construction of Plasmid pAMoPRSAT21 for Secretory Expression of α-1,3-fucosyltransferease (TH21) (cf. FIG. 29)

Based on its primary sequence, the thus-cloned α-1,3-fucosyltransferase (TH21) is composed of the N-terminal cytoplasmic region (14 amino acid residues), the subsequent membrane binding region (19 amino acid residues) and the C-terminal region (309 amino acid residues) having catalytic activity. Therefore, an attempt was made to cause secretory expression of the novel α-1,3-fucosyltransferase species (TH21) by deleting the cytoplasmic and membrane binding regions and instead adding the signal sequence of human granulocyte colony stimulating factor and the IgG binding region of *Staphylococcus aureus* protein A. The gene portion coding for the C-terminal region [in SEQ ID NO: 1 or SEQ ID NO:2, from the 39th amino acid (glycine) residue to the 342nd amino acid (alanine) residue] was excised from pUC119-TH21 and inserted into the secretory Fuc-TVI expression plasmid pAMoPRSAFT6 constructed in section 4 in place of the Fuc-TVI-encoding region to construct a plasmid, pAMoPRSAT21. pAMoPRSAT21 is capable of secretory production of a fused protein composed of the IgG binding region of protein A and the α-1,3-fucosyltransferase segment [from the 39th amino acid (glycine) residue to the 342nd amino acid (alanine) residue], with the Fuc-TVI-derived 15 amino acid residues [from the 40th amino acid (aspartic acid) residue to the 54th amino acid (threonine) residue] inserted therebetween.

First, the region coding for the signal sequence of human granulocyte colony stimulating factor, the IgG binding region of protein A and the Fuc-TVI-derived 15 amino acids [from the 40th amino acid (aspartic acid) residue to the 54th amino acid (threonine) residue] was prepared by PCR using pAMoPRSAFT6 as a template. The following two synthetic DNAs [Mo-1 (24 mer; SEQ ID NO:14) and F6-F (31 mer; SEQ ID NO:15)] were synthesized as primers for PCR using an Applied Biosystems model 380A DNA synthesizer.

```
Mo-1 (24 mer)
5'-CGCCAGTCCTCCGATTGACTGAGT-3'

F6-F (31 mer)
5'-CCATGGTACCTGTGCTGTCTGGGAAGCGGGA-3'
```

F6-F (31 mer) has a construction causing introduction of an Asp718 site. Therefore, the DNA fragment amplified by PCR was cleaved with HindIII and Asp718. The PCR was carried out using Takara Shuzo's kit (GeneAmp™ DNA Amplification Reagent Kit with AmpliTaq™ Recombinant Taq DNA Polymerase). The reaction solution was prepared as described in the manual attached to the kit. The reaction steps (94° C., 1 minute; 65° C., 1 minute; and 72° C., 3 minutes) were repeated in a total of 20 cycles using Perkin Elmer Cetus' DNA Thermal Cylcer (distributed by Takara Shuzo) and the reaction was further conducted at 72° C. for 7 minutes. The plasmid pAMoPRSAFT6 (70 ng) was used as a template. After completion of the reaction, chloroform extraction and ethanol precipitation were performed. The precipitate was dissolved in 30 μl of Y-80 buffer, 20 units of Asp718 was added and the digestion reaction was carried out at 37° C. for 2 hours. Then, 5 units of HindIII was added and partial digestion was effected at 37° C. for 10 minutes. The reaction mixture was subjected to agarose gel electrophoresis and a DNA fragment of about 0.4 kb was recovered.

Separately, 2 μg of pUC119-TH21 was dissolved in 30 μl of Y-100 buffer, 20 units of TaqI was added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 5' cohesive end resulting from TaqI digestion to a blunt end.

The reaction was terminated by extraction with phenol and, after chloroform extraction and ethanol precipitation, the precipitate was dissolved in 30 µl of Y-80 buffer, 20 units of Asp718 was added and the digestion reaction was carried out at 37° C. for 2 hours. The reaction mixture was subjected to agarose gel electrophoresis and a DNA fragment of about 1.0 kb was recovered.

Further, separately, 2 µg of pAMoPRC3Sc was dissolved in 30 µl of Y-150 buffer, 20 units of NotI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end resulting from NotI digestion to a blunt end. The reaction was terminated by extraction with phenol and, after chloroform extraction and ethanol precipitation, the precipitate was dissolved in 30 µl of Y-80 buffer, 20 units of HindIII was added and the digestion reaction was carried out at 37° C. for 2 hours. The reaction mixture was subjected to agarose gel electrophoresis and a DNA fragment of about 8.7 kb was recovered.

The HindIII-Asp718 fragment (0.4 kb; 0.05 µg) derived from the PCR-amplified DNA, the pUC119-TH21-derived Asp718-TagI (blunt end) fragment (1.0 kb; 0.1 µg) and the pAMoPRC3Sc-derived HindIII-NotI (blunt end) fragment (8.7 kb; 0.2 µg), obtained as described above, were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant strain by a known method. This plasmid was named pAMoPRSAT21 and its structure was identified by digestion with restriction enzymes.

(2) Secretory Production of α-1,3-fucosyltransferase (TH21) and Fuc-TVI Using Namalwa KJM-1 Cells as Host In a parallel run, Fuc-TVI was prepared and used as a control, since Fuc-TVI is a known species of α-1,3-fucosyltransferase.

The plasmids pAMoPRSA (secretory production vector), pAMoPRSAT21 [plasmid for secretory expression of α-1,3-fucosyltransferase (TH21)] and pAMoPRSAFT6 (plasmid for secretory production of Fuc-TVI), obtained as described above, were prepared using Qiagen's plasmid preparation kit (>plasmid<maxi kit, article number 41031). Each plasmid obtained was precipitated with ethanol, then dissolved in TE buffer to a concentration of 1 µg/µl and introduced into Namalwa KJM-1 cells by electroporation. After introduction of 4 µg of plasmid per $1.6 \times 10^6$ cells, the cells were suspended in 8 µl of RPMI1640-ITPSGF medium and cultured in a $CO_2$ incubator at 37° C. for 24 hours. Then, G418 (Gibco) was added to a concentration of 0.5 mg/ml and cultivation was further continued for 7 days. Then, 22 ml of RPMI1640-ITPSGF medium (containing 0.5 mg/ml of G418) was added and cultivation was further continued for 5 days to give transformants. The transformant strains thus obtained were each suspended, to a concentration of $5 \times 10^4$ cells/ml, in 30 ml of RPMI1640-ITPSGF medium containing 0.5 mg/ml of G418 and cultured in a $CO_2$ incubator at 37° C. for 8 days. Then, cells were removed by centrifugation (160×g, 10 minutes). Each supernatant was recovered and again centrifuged (1,500×g, 10 minutes) and the supernatant was recovered. The supernatants thus obtained were stored at −80° C. until use.

The α-1,3-fucosyltransferase species (TH21) encoded by the plasmid pAMoPRSAT21 and Fuc-TVI encoded by the plasmid pAMoPRSAFT6 are expressed each as a fused protein with the IgG binding region of protein A and therefore can be readily purified using IgG-Sepharose. Thus, sodium azide was added to each supernatant obtained in the above manner to a final concentration of 0.1%, 10 µl of IgG-Sepharose (Pharmacia) pretreated as described in the product manual was added and the mixture was stirred gently overnight at 4° C. The IgG-Sepharose was then recovered by centrifugation (160×g, 10 minutes), washed with three 1-ml portions of RPMI1640-ITPSGF medium and suspended in 10 µl of RPMI1640-ITPSGF medium. A 5-ml portion of each IgG-Sepharose suspension thus obtained was subjected to fucosyltransferase activity determination.

For activity determination, the reaction was carried out in 30 µl of an assay solution [0.1 M cacodylic acid-hydrochloric acid (pH 6.8), 25 mM manganese chloride, 10 mM L-fucose, 5 mM ATP, 0.1 mM substrate, above-mentioned IgG-Sepharose (5 µl), 1.5 mM GDP-fucose (with or without addition)] at 37° C. for 2 hours and then product identification was performed by high performance liquid chromatography (HPLC). The following substrates were used after fluorescence labelling with aminopyridine: Lacto-N-neotetraose (Galβ1-4GlcNAcβ1-3Galβ1-4Glc; hereinafter, "LNnT"), lacto-N-tetraose (Galβ1-3GlcNAcβ1-3Galβ1-4G1c; hereinafter, "LNT"), sialyllacto-N-tetraose a: hereinafter, "LSTa"), lacto-N-fucopentaose I (Fucα1-2Galβ1-3GlcNAcβ1-3Galβ1-4Glc: hereinafter, "LNFP-I"), lacto-N-fucopentaose II (Galβ1-3(Fucα1-4)GlcNAcβ1-3Galβ1-4Glc; hereinafter, "LNFP-II"), lacto-N-fucopentaose III (Galβ1-4(Fucα1-3)GlcNAcβ1-3Galβ1-4Glc; hereinafter, "LNFP-III") and lacto-N-fucopentaose V (Galβ1-3GlcNAcβ1-3Galβ1-4(Fucα1-3)Glc: hereinafter, "LNFP-V") (all available from Oxford Glycosystems). The substrates were fluorescence-labeled by the conventional method [Kondo et al.: Agricultural and Biological Chemistry, 54, 2169 (1990)]. Further, by using LNnT fluorescence-labeled with aminopyridine as a substrate and treating the same with the secretory α-2,3-sialyltransferase (WM17) prepared in section 2 above, sialyl-lacto-N-neotetraose (NeuAcα2-3Galβ1-4GlcNAcβ1-3Galβ1-4Glc; hereinafter, "sialyl-LNnT") fluorescence-labeled with aminopyridine was prepared for use as a substrate. Similarly, sialyllacto-N-fucopentaose V (NeuAcα2-3Galβ1-3GlcNAcβ1-3Galβ1-4(Fucα1-3)Glc; hereinafter, "sialyl-LNFP-V") fluorescence labeled with aminopyridine was prepared for use as a substrate by using LNFP-V fluorescence-labeled with aminopyridine as a substrate and treating the same with the secretory α-2,3-sialyltransferase (WM16) prepared in section 3 above. For each substrate, the reaction was carried out using the assay solution containing GDP-fucose (carbohydrate donor) and the assay solution free of GDP-fucose. The peak appearing only with the GDP-fucose-containing assay solution as analyzed by HPLC was regarded as the product peak. After completion of the reaction, the assay solution was treated at 100° C. for 5 minutes and subjected to centrifugation (10,000×g, 10 minutes), and a 10-µl portion of the supernatant obtained was subjected to HPLC. For HPLC, a TSK gel ODS-80TM column (4.6 mm×30 cm; Tosoh) was used and elution was carried out with 0.02 M ammonium acetate buffer (pH 4.0) at an elution temperature of 30° C. and a flow rate of 1 ml/minute. For product detection, a Shimadzu model RF-535T fluorescence HPLC monitor was used (excitation wavelength: 320 nm; emission wavelength: 400 nm). Agreement in elution time with the standard carbohydrate chain was used as an index for product identification. The following were used as standards: LNFP-I, LNFP-II, LNFP-III and LNFP-V, each fluorescence-labeled with aminopyridine, as well as sialyl-lacto-N-fucopentaose III (NeuAcα2-3Galβ1-4(Fucα1-3) GlcNAcβ1-3Galβ1-4-Glc; sialyl-LNFP-III) prepared by reacting sialyl-LNnT fluorescence-labeled with aminopyridine, used as a substrate, with the secretory Fuc-TVI enzyme.

For product quantitation, aminopyridylated lactose was used as a standard and fluorescene intensity comparison was made.

For IgG-Sepharose samples derived from culture supernatants of Namalwa cells harboring pAMoPRSAT21 introduced therein, α-1,3-fucosyltransferase activity was detected only when sialyl-LNnT was used as the substrate. Specifically, 3.2 picomoles of sialyl-LNFP-III was synthesized per hour using the quantity of secretory enzyme produced in 1 ml of medium, with sialyl-LNnT as the substrate. On the contrary, for IgG Sepharose samples derived from culture supernatants of Namalwa cells harboring pAMoPRSA introduced therein, no activity was detected with any substrate.

The above results indicate that α-1,3-fucosyltransferase (TH21) can be produced and secreted in the culture supernatant as a protein fused to the IgG binding region of *Staphylococcus aureus* protein A and that the secretion product can be readily recovered and purified using IgG-Sepharose.

EXAMPLE 4

Quantitation of α-1,3-fucosyltransferase (TH21) Transcription Product by PCR and Study of Expression Levels in Various Cells The α-1,3-fucosyltransferase (TH21) transcription product was quantitated by quantitative PCR in the conventional manner [Gilliland et al.: Proceedings of the National Academy of Sciences of the U.S.A., 87, 2725 (1990)]. The β-actin transcription product, which is considered to be expressed at approximately the same level in all cells, was simultaneously quantitated to correct differences in the quantity of mRNA among cells and differences in the efficiency of conversion, due to reverse transcriptase, from mRNA to single-stranded cDNA among samples. Thus, the quantity of α-1,3-fucosyltransferase (TH21) transcription product for each cell species or cell line was expressed as a relative value with the quantity of β-actin transcription product being taken as 100.

(1) Cloning of β-Actin cDNA

The β-actin cDNA was prepared by PCR using, as a template, single-stranded cDNA synthesized from total RNA of U-937 cells (human monocytic cell line) using reverse transcriptase. The total RNA of U-937 cells was prepared by the conventional method [Chirgwin et al.: Biochemistry, 18, 5294 (1977)]. Single-stranded cDNA synthesis from the total RNA was performed using the kit Superscript™ Preamplification System (BRL). The following two synthetic DNAs [Ac-N (40 mer; SEQ ID NO:16) and Ac-C (40 mer; SEQ ID NO:17)], that were used as primers for PCR, were synthesized using an Applied Biosystems model 380A DNA synthesizer.

```
Ac-N (40 mer)
5'-AAGTATAAGCTTCCATGGATGATGATATCGCCGCGCTCGT-3'

Ac-C (40 mer)
5'-ATTTAAGGTACCGAAGCATTTGCGGTGGACGATGGAGGGG-3'
```

Since Ac-N (40 mer) is constructed to give a HindIII site and Ac-C (40 mer) to give an Asp718 site, the DNA fragment amplified by PCR can be inserted, after cleavage with HindIII and Asp718, into pUC119 between the HindIII and Asp718 sites. The PCR was performed using Takara Shuzo's kit (GeneAmp™ DNA Amplification Reagent kit with AmpliTag™ Recombinant Taq DNA Polymerase). The reaction solution was prepared according to the manual attached to the kit. The reaction steps (94° C., 30 seconds; 65° C., 1 minute; and 72° C., 3 minutes) were performed in a total of 20 cycles using Perkin Elmer Cetus' DNA Thermal Cycler (distributed by Takara Shuzo) and then the reaction was further conducted at 72° C. for 7 minutes. The single-stranded cDNA (about 200 ng) synthesized from the total RNA of U-937 cells using reverse transcriptase was used as the template. After completion of the reaction, chloroform extraction and ethanol precipitation were performed and the precipitate was dissolved in 30 μl of Y-80 buffer and, after addition of 20 units of HindIII and 20 units of Asp718, the digestion reaction was carried out at 37° C. for 2 hours. The reaction mixture was subjected to agarose gel electrophoresis and a DNA fragment of about 1.2 kb was recovered.

Separately, 1 μg of pUC119 was dissolved in 30 μl of Y-100 buffer, 20 units of HindIII and 20 units of Asp718 were added and the digestion reaction was carried out at 37° C. for 2 hours. Then, agarose gel electrophoresis was performed and a DNA fragment of about 3.1 kb was recovered.

The HindIII-Asp718 fragment (1.2 kb; 0.05 μg) derived from the PCR-amplified DNA and the pUC119-derived HindIII Asp718 fragment (3.1 kb; 0.1 μg), obtained as described above, were dissolved in 30 μl of T4 ligase buffer, 175 units of T4 DNA ligase was added and the ligation reaction was carried out at 12° C. for 16 hours.

The reaction mixture was used to transform *Escherichia coli* HB101 by the method of Cohen et al. and ampicillin-resistant strains were obtained. Plasmids were isolated from these transformant strains by a known method. A plasmid was named pUC119-ACT and its structure was identified by digestion with restriction enzymes.

(2) Construction of Plasmid pUC119-ACTd Having Deletion Mutation within β-Actin cDNA pUC119-ACT (2 μg) constructed in (1) was dissolved in 30 μl of Y-50 buffer, 20 units of Eco01091 was added and the digestion reaction was carried out at 37° C. for 2 hours. After precipitation with ethanol, the precipitate was dissolved in 30 ml of DNA polymerase I buffer, 6 units of *Escherichia coli*-derived DNA polymerase I Klenow fragment was added and the reaction was carried out at 37° C. for 60 minutes to convert the 5' cohesive end resulting from Eco01091 digestion to a blunt end. The reaction was terminated by extraction with phenol and, after chloroform extraction and ethanol precipitation, the precipitate was dissolved in 30 μl of Y-80 buffer, 20 units of HindIII was added and the digestion reaction was carried out at 37° C. for 2 hours. The reaction mixture was subjected to agarose gel electrophoresis and a DNA fragment of about 0.3 kb was recovered.

Separately, 2 μg of pUC119-ACT was dissolved in 30 μl of Y-100 buffer, 20 units of BstEII was added and the digestion reaction was carried out at 60° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 5' cohesive end resulting from BstEII digestion to a blunt end. The reaction was terminated by extraction with phenol and, after chloroform extraction and ethanol precipitation, the precipitate was dissolved in 30 μl of Y-80 buffer, 20 units of HindIII was added and the digestion reaction was carried out at 37° C. for 2 hours. The reaction mixture was subjected to agarose gel electrophoresis and a DNA fragment of about 3.8 kb was recovered.

The pUC119-ACT-derived Eco01091 (blunt end)-HindIII fragment (0.3 kg; 0.1 μg) and pUC119-ACT-derived BstEII (blunt end)-HindIII fragment (3.8 kb; 0.2 μg) obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant by a known method. This plasmid was named pUC119-ACTd and its structure was identified by digestion with restriction enzymes.

(3) Construction of Plasmid pUC119-TH21d Having Deletion Mutation within α-1,3-fucosyltransferase cDNA (TH21)

pUC119-TH21 (2 µg), constructed in Example 2, section 3-(1), was dissolved in 30 µl of Y-0 buffer, 20 units of ApaI and 20 units of NaeI were added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 3' cohesive end resulting from ApaI digestion to a blunt end. The reaction was terminated by extraction with phenol. After chloroform extraction and ethanol precipitation, the precipitate was dissolved in 30 µl of Y-80 buffer, 20 units of HindIII was added and the digestion reaction was carried out at 37° C. for 2 hours. The reaction mixture was subjected to agarose gel electrophoresis and a DNA fragment of about 0.6 kb was recovered.

Separately, 2 µg of pUC119-TH21 was dissolved in 30 µl of a buffer comprising 10 mM Tris-HCl (pH 7.5), 6 mM MgCl$_2$, 200 mM NaCl and 6 mM 2-mercaptoethanol (said buffer hereinafter referred to as "Y-200 buffer"), 20 units of BstXI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 3' cohesive end resulting from BstXI digestion to a blunt end. The reaction was terminated by extraction with phenol and, after chloroform extraction and ethanol precipitation, the precipitate was dissolved in 30 µl of Y-80 buffer, 20 units of HindIII was added and the digestion reaction was carried out at 37° C. for 2 hours. The reaction mixture was subjected to agarose gel electrophoresis and a DNA fragment of about 4.1 kb was recovered.

The pUC119-TH21-derived ApaI (blunt end)-HindIII fragment (0.6 kg; 0.1 µg) and pUC119-TH21-derived BstXI (blunt end)-HindIII fragment (4.1 kg; 0.2 µg) obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant strain by a known method. This plasmid was named pUC119-TH21d and its structure was identified by digestion with restriction enzymes.

(4) Quantitation of α-1,3-fucosyltransferase (TH21) Transcription Product in Various Cells and Cell Lines by Quantitative PCR (a) Synthesis of Single-Stranded cDNAs (for Use as Templates in Quantitative PCR) from Various Cells and Cell Lines The following cell lines were used: KJM-1 cells, WM266-4 cells (ATCC CRL 1676), THP-1 cells (ATCC TIB 202), HL-60 cells (ATCC CCL 240), U-937 cells (ATCC CCL 1593), Colo205 cells (ATCC CCL 222), LS180 cells (ATCC CL 187), SW1116 cells (ATCC CCL 233), Jurkat cells, KATO III cells (ATCC HTB 103), Capan-1 cells (ATCC HTB 79), PC-3 cells (ATCC CRL 1435), SK-N-MC cells (ATCC HTB 10), PC-9 cells, HeLa cells (Japan Cancer Research Resources Bank CCL 2) and human umbilical vascular endothelial cells (HUVEC; ATCC CRL 1730).

Further, polymorphonuclear leukocytes and mononuclear leukocytes were respectively isolated from healthy adult peripheral blood using Nycomed Pharma's kit Polymorphprep™. The mononuclear leukocytes obtained were further separated into monocytes and lymphocytes by the conventional method [Gonawa et al: Journal of Immunology, 130, 706 (1983)].

For each cell species, the total RNA was prepared by the conventional method [Chirgwin et al.: Biochemistry, 18, 5294 (1977)]. Single-stranded cDNA synthesis from the total RNA was performed using BRL's kit (Superscript™ Preamplification System). Single-stranded cDNA was synthesized from 5 µg (in the case of cell lines) or 1 µg (in the case of hemocytes) of total RNA, and the cDNA was used as the template for PCR after 50-fold or 10-fold dilution with water, respectively.

(b) Preparation of Standard and Internal Control for Quantitative PCR pUC119-TH21 and pUC119TH21d were cleaved with restriction enzymes capable of excising each cDNA portion to convert the same to a linear DNA and the linear DNAs thus obtained were used as a standard and an internal control, respectively, for α-1,3-fucosyltransferase (TH21) transcription product quantitation. Thus, pUC119-TH21 and pUC119-TH21d (2 µg each) were dissolved in 40 µl of Y-80 buffer, 20 units of HindIII and 20 units of XbaI were added and the digestion reaction was carried out at 37° C. for 2 hours. A portion (5 µl) of each reaction mixture was subjected to agarose gel electrophoresis and, after confirmation of complete cleavage, the reaction mixture was stepwise diluted, for use, with water containing 1 µg/µl of yeast transfer RNA.

Separately, pUC119-ACT and pUC119-ACTd were cleaved with restriction enzymes suited for excising the cDNA portion to convert the same to a linear DNA and the linear DNAs thus obtained were used as a standard and an internal control, respectively, for β-actin transcription product quantitation. Thus, pUC119-ACT and pUC119-ACTd (2 µg each) were respectively dissolved in 40 µl of Y-80 buffer, 20 units of HindIII and 20 units of Asp718 were added and the digestion reaction was carried out at 37° C. for 2 hours. A portion (5 µl) of each reaction mixture was subjected to agarose gel electrophoresis and, after confirmation of complete cleavage, the reaction mixture was stepwise diluted, for use, with water containing 1 µg/µl of yeast transfer RNA.

(c) Quantitation of α-1,3-fucosyltransferase (TH21) Transcription Product by Quantitative PCR First, the PCR was carried out in the presence of 10 fg of the internal control (HindIII- and XbaI-cleaved pUC119-TH21d) prepared in (b), with the single-stranded cDNA prepared in (a) from each cell species or cell line being used as the template. The following two synthetic DNAs [T21-2 (23 mer; SEQ ID NO:18) and T21-4 (24 mer; SEQ ID NO:19)] were synthesized, for use as primers for PCR, using an Applied Biosystems model 380A DNA synthesizer.

```
T21-2 (23 mer)
5'-CACCTCCGAGGCATCTTCAACTG-3'

T21-4 (24 mer)
5'-CGTTGGTATCGGCTCTCATTCATG-3'
```

The PCR was carried out using Takara Shuzo's kit (GeneAmp™ DNA Amplification Reagent Kit with AmpliTaq™ Recombinant Taq DNA Polymerase). The reaction solution (40 µl) was prepared as described in the manual of the kit. On that occasion, dimethyl sulfoxide was added to a final concentration of 5%. The reaction solution (39 µl) containing all reagents except for Taq DNA polymerase was treated at 97° C. for 5 minutes using Perkin Elmer Cetus' DNA Thermal Cycler (distributed by Takara Shuzo) and then quenched in ice. To the reaction mixture was added 1 µl of 5-fold diluted Taq DNA polymerase and the reaction steps (94° C., 30 seconds; 65° C., 1 minute; and 72° C., 2 minutes) were conducted in a total of 30 cycles using Perkin Elmer Cetus' DNA Thermal Cycler. A portion (15 µl) of the reaction mixture was subjected to agarose gel electrophoresis and the pattern of amplified DNA fragments was recorded photographically. Then, the negative film was scanned by means of a Shimadzu model CS-900 densitometer for determining the amount of amplified DNA fragments. A calibration curve was prepared by carrying out the PCR in the same manner using the standard (HindIII- and XbaI-cleaved pUC119-TH21) prepared in (b) as the template in lieu of the single-stranded cDNAs derived from various cell species or cell lines. The DNA fragment derived from the α-1,3-fucosyltransferase (TH21) transcription product and from the standard is 497 bp in size, while the DNA fragment derived from the internal control is 336 bp in size. The amount (number of moles) of the α-1,3-fucosyltransferase (TH21) transcription product was calculated based on the quantitative proportions between both the DNA fragments.

For more precise quantitation of the transcription product, the same PCR was repeated with each sample using the internal standard in an amount close to the quantity of transcription product as determined in the above manner. The number of cycles of PCR was varied according to the amount of internal control.

In quantitating the β-actin transcription product as well, the PCR was performed in two steps. On this occasion, the HindIII- and Asp718-cleaved pUC119-ACTd prepared in (b) was used as the internal control and the HindIII- and Asp718-cleaved pUC119-ACT prepared in (b) as the standard. The following two synthetic DNAs [Ac-1 (24 mer; SEQ ID NO:20) and Ac-3 (24 mer; SEQ ID NO:21)] were synthesized, for use as primers for PCR, using an Applied Biosystems model 380A DNA synthesizer.

```
Ac-1 (24 mer)
5'-GATATCGCCGCGCTCGTCGTCGAC-3'

Ac-3 (24 mer)
5'-CAGGAAGGAAGGCTGGAAGAGTGC-3'
```

The first PCR was carried out in 17 cycles using 10 pg of the internal control. In the case of β-actin, dimethyl sulfoxide was not added to the PCR reaction mixture.

The amount of the α-1,3-fucosyltransferase (TH21) transcription product was finally determined as a relative value with the amount of β-actin transcription product taken as 100. The results thus obtained are shown in Table 1.

TABLE 1

| Cells | Amount of transcription product |
|---|---|
| THP-1 | 0.20 |
| HL-60 | 0.82 |
| U-937 | 0.59 |
| KJM-1 | <0.01 |
| Jurkat | <0.01 |
| WM266-4 | <0.01 |
| Colo205 | <0.01 |
| LS180 | 0.03 |
| SW1116 | <0.01 |
| KATOIII | <0.01 |
| Capan-1 | <0.01 |
| PC-3 | <0.01 |
| SK-N-MC | <0.01 |
| PC-9 | <0.01 |
| HeLa | <0.01 |
| HUVEC | <0.01 |
| Polymorphonuclear leukocytes | 0.77 |
| Monocytes | 0.06 |
| Lymphocytes | 0.08 |

As shown in Table 1, the α-1,3-fucosyltransferase (TH21) was found to have been expressed specifically in monocytic/granulocytic cell lines (THP-1 cells, HL-60 cells, U-937 cells) and peripheral leukocytes (in particular polymorphonuclear leukocytes) Based on the fact that the novel α-1,3-fucosyltransferase is expressed specifically in leukocyte cells and that it can synthesize the sialyl Lewis x carbohydrate chain in vitro as well as in vivo, it was proved that it is involved in the synthesis of the carbohydrate chain ligand of selectin in leukocytes.

The above results revealed that the α-1,3-fucosyltransferase (TH21) transcription product can be quantitated by quantitative PCR.

INDUSTRIAL APPLICABILITY

The present invention provides α-1,3-fucosyltransferase useful in the production of carbohydrate chains having useful physiological activity, for example sialyl Lewis x, and modifications thereof.

References cited above are incorporated herein in their entirety by reference.

The invention claimed is:

1. An isolated DNA which hybridizes with the DNA consisting of the nucleotide sequence defined in SEQ ID NO:1 under stringent conditions which comprises performing hybridization at 65° C. in the presence of 1.0M sodium chloride and then washing at 65° C. in a 0.1-fold concentrated SSC solution, and which encodes a protein having α-1,3-fucosyltransferase activity to synthesize sialyl Lewis x from sialyl-lacto-N-neotetraose.

2. A recombinant vector comprising, as an insert, the DNA of claim 1.

3. An isolated host cell transformed with the recombinant vector of claim 2.

4. An *Escherichia coil* strain transformed with the recombinant vector of claim 2.

5. A method of producing an α-1,3-fucosyltransferase comprising culturing the cell according to claim 3 under conditions such that said sequence is expressed and said α-1,3-fucosyltransferase is thereby produced.

6. A method of producing an α-1,3-fucosyltransferase comprising culturing the cell according to claim 4 under conditions such that said sequence is expressed and said α-1,3-fucosyltransferase is thereby produced.

7. A method of introducing the sialyl Lewis x structure onto a carbohydrate chain of a glycoprotein or glycolipid having a NeuAcα2, 3Galβ1, 4GlcNAc structure at a non-reducing end of said carbohydrate chain comprising culturing a cell producing said glycoprotein or glycolipid and transformed with a recombinant vector comprising, as an insert, a DNA of claim 1, under conditions such that said DNA is expressed and an α-1, 3-fucosyltransferase encoded by said DNA is thereby produced, and such that said α-1, 3-fucosyltransferase effects the introduction of said sialyl Lewis x structure into a carbohydrate chain of the glycoprotein or glycolipid present in said cell.

* * * * *